(12) United States Patent
Su

(10) Patent No.: US 12,371,670 B2
(45) Date of Patent: Jul. 29, 2025

(54) FAST AND ACCURATE THREE-PLASMID ONCOLYTIC ADENOVIRUS RECOMBINANT PACKAGING SYSTEM Ad5MixPlus AND APPLICATION THEREOF

(71) Applicant: VONCOLYTIC THERAPEUTICS CO., LTD., Xuzhou (CN)

(72) Inventor: Yinghan Su, Jiangsu (CN)

(73) Assignee: VONCOLYTIC THERAPEUTICS CO., LTD., Xuzhou (CN)

( * ) Notice: Subject to any disclaimer, the term of this patent is extended or adjusted under 35 U.S.C. 154(b) by 887 days.

(21) Appl. No.: 17/615,163

(22) PCT Filed: Jan. 2, 2020

(86) PCT No.: PCT/CN2020/070125
§ 371 (c)(1),
(2) Date: Nov. 30, 2021

(87) PCT Pub. No.: WO2020/258825
PCT Pub. Date: Dec. 30, 2020

(65) Prior Publication Data
US 2022/0235332 A1    Jul. 28, 2022

(30) Foreign Application Priority Data

Jun. 24, 2019    (CN) .......................... 201910549429.9

(51) Int. Cl.
*C12N 7/00* (2006.01)
*C12N 15/85* (2006.01)
*C12N 15/861* (2006.01)

(52) U.S. Cl.
CPC ............... *C12N 7/00* (2013.01); *C12N 15/85* (2013.01); *C12N 15/861* (2013.01);
(Continued)

(58) Field of Classification Search
None
See application file for complete search history.

(56) References Cited

U.S. PATENT DOCUMENTS

2007/0141706 A1*  6/2007  Li ............................ C12N 7/00
                                                          435/456
2011/0065100 A1*  3/2011  Aldred ................. C12Q 1/6886
                                                           506/14

FOREIGN PATENT DOCUMENTS

CN    101565718 A    10/2009
CN    102154213 A    8/2011
(Continued)

OTHER PUBLICATIONS

Wold WS, Toth K. Adenovirus vectors for gene therapy, vaccination and cancer gene therapy. Curr Gene Ther. Dec. 2013;13(6):421-33. doi: 10.2174/1566523213666131125095046. PMID: 24279313; PMCID: PMC4507798. (Year: 2013).*

(Continued)

*Primary Examiner* — Thomas J. Visone
*Assistant Examiner* — Katherine A. Willard
(74) *Attorney, Agent, or Firm* — Banner & Witcoff, Ltd.

(57) ABSTRACT

A fast and accurate three-plasmid oncolytic adenovirus recombinant packaging system Ad5MixPlus and an application thereof are provided. The system is composed of three adenovirus recombinant plasmids. The core technology of the system is that two sets of different site recombination sequences are skillfully loaded on a first 5-type adenovirus right arm backbone plasmid large vector, then two small shuttle plasmids respectively provide a right arm-modified Hexon/E3/Fiber sequence and an E1a expression cassette controlled by a left arm tumor-specific promoter, and the difficulties and obstacles to the modification of the adenovirus backbone large vector are overcome. After two rounds (Continued)

of site-specific recombination, the ideal oncolytic adenovirus is packaged accurately and quickly.

14 Claims, 8 Drawing Sheets

Specification includes a Sequence Listing.

(52) U.S. Cl.
CPC .............. *C12N 2710/10032* (2013.01); *C12N 2710/10052* (2013.01); *C12N 2800/107* (2013.01); *C12N 2830/008* (2013.01)

(56) References Cited

FOREIGN PATENT DOCUMENTS

| CN | 102844329 A | 12/2012 |
|---|---|---|
| CN | 106190992 A | 12/2016 |
| CN | 107418975 A | 12/2017 |
| CN | 109295096 A | 2/2019 |
| CN | 110272917 A | 9/2019 |

OTHER PUBLICATIONS

Hong-Yan Liu, Bing-Juan Han, Yu-Xu Zhong, Zhuo-Zhuang Lu. A three-plasmid system for construction of armed oncolytic adenovirus. Journal of Virological Methods. vol. 162, Issues 1-2. 2009. pp. 8-13. ISSN 0166-0934. https://doi.org/10.1016/j.jviromet.2009.07.011. (Year: 2009).*

Soriano. Plasmids 101—Gateway Cloning. 2017. https://blog.addgene.org/plasmids-101-gateway-cloning. Webpage accessed Jan. 30, 2025. (Year: 2017).*

Li, X., Mao, Q., Wang, D., & Xia, H. (2012). A novel Ad5/11 chimeric oncolytic adenovirus for improved glioma therapy. International Journal of Oncology, 41, 2159-2165. https://doi.org/10.3892/ijo.2012.1674 (Year: 2012).*

Roberts, D., Nanda, A., Havenga, M. et al. Hexon-chimaeric adenovirus serotype 5 vectors circumvent pre-existing anti-vector immunity. Nature 441, 239-243 (2006). https://doi.org/10.1038/nature04721 (Year: 2006).*

Wang et al. "A novel Golgi protein (GOLPH2)-regulated oncolytic adenovirus exhibits potent antitumor efficacy in hepatocellular carcinoma" Oncotarget, vol. 6, No. 15, Apr. 23, 2015. pp 13564-13578.

Apr. 3, 2020 (WO) International Search Report PCT/CN2020/070125.

* cited by examiner

```
                              SEQUENCE LISTING

<160> NUMBER OF SEQ ID NOS: 8

<210> SEQ ID NO 1
<211> LENGTH: 35558
<212> TYPE: DNA
<213> ORGANISM: Artificial
<220> FEATURE:
<223> OTHER INFORMATION: adenovirus right arm backbone plasmid
<220> FEATURE:
<221> NAME/KEY: misc_feature
<222> LOCATION: (721)..(721)
<223> OTHER INFORMATION: n is a, c, g, or t
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (1118)..(1118)
<223> OTHER INFORMATION: n is a, c, g, or t
<220> FEATURE:
<221> NAME/KEY: misc_feature
<222> LOCATION: (1197)..(1197)
<223> OTHER INFORMATION: n is a, c, g, or t
<220> FEATURE:
<221> NAME/KEY: misc_feature
<222> LOCATION: (2254)..(2254)
<223> OTHER INFORMATION: n is a, c, g, or t

<400> SEQUENCE: 1
ttattttgga ttgaagccaa tatgataatg aggggggtgga gtttgtgacg tggcgcgggg      60
cgtgggaacg gggcgggtga cgtagtagtg tggcggaagt gtgatgttgc aagtgtggcg     120
gaacacatgt aagcgacgga tgtggcaaaa gtgacgtttt tggtgtgcgc cggatccaca     180
ggacgggtgt ggtcgccatg atcgcgtagt cgatagtggc tccaagtagc gaagcgagca     240
ggactgggcg gcggccaaag cggtcggaca gtgctccgag aacgggtgcg catagaaatt     300
gcatcaacgc atatagcgct agcagcacgc catagtgact ggcgatgctg tcggaatgga     360
cgatatcccg caagaggccc ggcagtaccg gcataaccaa gcctatgcct acagcatcca     420
gggtgacggt gccgaggatg acgatgagcg cattgttaga tttcatacac ggtgcctgac     480
tgcgttagca atttaactgt gataaactac cgcattaaag cttatcgttc gaatttgggg     540
ggatcttcga tgctagacga tccagacatg ataagataca ttgatgagtt tggacaaacc     600
acaactagaa tgcagtgaaa aaaatgcttt atttgtgaaa tttgtgatgc tattgcttta     660
tttgtaacca ttataagctg caataaacaa gttgctcgaa gtcgacgatc cgaacaaacg     720
ncccaacacc cgtgcgtttt attctgtctt tttattgccg atccctcag aagaactcgt      780 caagaaggcg atagaaggcg atgcgctgcg aatcgggagc ggcgataccg taaagcacga     840
ggaagcggnc agcccattcg ccgccatgtt tttnagcaat atcacgggta gccaacgcta     900
tgtcctgata gcggtccgcc acacccagcc tcgacaattc caaccttacc caagagttcg     960
ccaaactcag acatcacttt agcaaaaccg cgccgtgctt cttcctcggt ggcattcatc    1020
acgaaatgtt cagcactacg catacttttg gacaggaaac gcaacggata ttgagtcaat    1080
atcaggcatt ctatcgctca gctttacagt gacaatgncg gctggcgact gaatattagt    1140
```

```
gcttacagac agcactacat attttccgtc gatgttgaaa tcctttctca tatgtcncca   1200
taaatatcaa ataattatag caatcattta cgcgttaatg gctaatcgcc atcttccagc   1260
aggcgcacca ttgcccctgt ttcactatcc aggttacgga tatagttcat gacaatattt   1320
acattggtcc agccaccagc ttgcatgatc tccggtattg aaactccagc gcgggccata   1380
tctcgcgcgg ctccgacacg ggcactgtgt ccagaccagg ccaggtatct ctgaccagag   1440
tcatccttag cgccgtaaat caatcgatga gttgcttcaa aaatcccttc cagggcgcga   1500
gttgatagct ggctggtggc agatggcgcg gcaacaccat tttttctgac ccggcaaaac   1560
aggtagttat tcggatcatc agctacacca gagacggaaa tccatcgctc gaccagtttta  1620 gttaccccca ggctaagtgc cttctctaca cctgcggtgc taaccagcgt tttcgttctg   1680
ccaatatgga ttaacattct cccaccgtca gtacgtgaga tatctttaac cctgatcctg   1740
gcaatttcgg ctatacgtaa cagggtgtta taagcaatcc ccagaaatgc cagattacgt   1800
atatcctggc agcgatcgct attttccatg agtgaacgaa cctggtcgaa atcagtgcgt   1860
tcgaacgcta gagcctgttt tgcacgttca ccggcatcaa cgttttcttt tcggatccgc   1920
cgcataacca gtgaaacagc attgctgtca cttggtcgtg gcagcccgga ccgacgatga   1980
agcatgttta gctggcccaa atgttgctgg atagttttta ctgccagacc gcgcgcctga   2040
agatatagaa gataatcgcg aacatcttca ggttctgcgg gaaaccattt ccggttattc   2100
aacttgcacc atgccgccca cgaccggcaa acggacagaa gcattttcca ggtatgctca   2160
gaaaacgcct ggcgatccct gaacatgtcc atcaggttct tgcgaacctc atcactcgtt   2220
gcatcgaccg gtaatgcagg caaatttttgg tgtncggtca gtaaattgga caccttcctc   2280
ttcttcttgg gcatggtcga gtctagactc gagggatcct cgactcgaag actgatcccc   2340
aggctggatc ggtcccggtg tcttctatgg aggtcaaaac agcgtggatg gcgtctccag   2400
gcgatctgac ggttcactaa acgagctctg cttatataga cctcccaccg tacacgccta   2460
ccgcccattt gcgtcaatgg ggcggagttg ttacgacatt ttggaaagtc ccgttgattt   2520
tggtgccaaa acaaactccc attgacgtca atggggtgga gacttggaaa tccccgtgag   2580
tcaaaccgct atccacgccc attgatgtac tgccaaaacc gcatcaccat ggtaatagcg   2640
atgactaata cgtagatgta ctgccaagta ggaaagtccc ataaggtcat gtactgggca   2700
taatgccagg gaattagatc cactagacga tgataagctg tcaaacatga gaattcttga   2760
agacgaaagg gcctcgtgat acgcctattt ttataggtta atgtcatgat aataatggtt   2820
tcttagacgt caggtggcac ttttcgggga aatgtgcgcg gaaccccttat tgtttatttt   2880 ttctaaatac attcaaatat gtatccgctc atgagacaat aaccctgata aatgcttcaa   2940
taatattgaa aaaggaagag tatgagtatt caacatttcc gtgtcgccct tattccctttt  3000 tttgcggcat tttgccttcc tgtttttgct cacccagaaa cgctggtgaa agtaaaagat   3060
gctgaagatc agttgggtgc acgagtgggt tacatcgaac tggatctcaa cagcggtaag   3120
atccttgaga gttttcgccc cgaagaacgt tttccaatga tgagcacttt taaagttctg   3180
ctatgtggcg cggtattatc ccgtgttgac gccgggcaag agcaactcgg tcgccgcata   3240
cactattctc agaatgactt ggttgagtac tcaccagtca cagaaaagca tcttacggat   3300
ggcatgacag taagagaatt atgcagtgct gccataacca tgagtgataa cactgcggcc   3360
aacttacttc tgacaacgat cggaggaccg aaggagctaa ccgcttttttt gcacaacatg  3420 ggggatcatg taactcgcct tgatcgttgg gaaccggagc tgaatgaagc cataccaaac   3480
gacgagcgtg acaccacgat gcctgcagca atggcaacaa cgttgcgcaa actattaact   3540
```

```
ggcgaactac ttactctagc ttcccggcaa caattaatag actggatgga ggcggataaa      3600
gttgcaggac cacttctgcg ctcggccctt ccggctggct ggtttattgc tgataaatct      3660
ggagccggtg agcgtgggtc tcgcggtatc attgcagcac tggggccaga tggtaagccc      3720
tcccgtatcg tagttatcta cacgacgggg agtcaggcaa ctatggatga acgaaataga      3780
cagatcgctg ataggtgc ctcactgatt aagcattggt aactgtcaga ccaagtttac       3840
tcatatatac tttagattga tttaaaactt cattttaat ttaaaaggat ctaggtgaag      3900
atcctttttg ataatctcat gaccaaaatc ccttaacgtg agttttcgtt ccactgagcg      3960
tcagaccccg tagaaaagat caaaggatct tcttgagatc ctttttttct gcgcgtaatc      4020
tgctgcttgc aaacaaaaaa accaccgcta ccagcggtgg tttgtttgcc ggatcaagag      4080
ctaccaactc tttttccgaa ggtaactggc ttcagcagag cgcagatacc aaatactgtc      4140
cttctagtgt agccgtagtt aggccaccac ttcaagaact ctgtagcacc gcctacatac      4200
ctcgctctgc taatcctgtt accagtggct gctgccagtg gcgataagtc gtgtcttacc      4260
gggttggact caagacgata gttaccggat aaggcgcagc ggtcgggctg aacggggggt      4320
tcgtgcacac agcccagctt ggagcgaacg acctacaccg aactgagata cctacagcgt      4380
gagcattgag aaagcgccac gcttcccgaa gggagaaagg cggacaggta tccggtaagc      4440
ggcagggtcg gaacaggaga gcgcacgagg gagcttccag ggggaaacgc ctggtatctt      4500
tatagtcctg tcgggtttcg ccacctctga cttgagcgtc gatttttgtg atgctcgtca      4560
ggggggcgga gcctatggaa aaacgccagc aacgcggcct ttttacggtt cctggccttt      4620
tgctggcctt ttgctcacat gttctttcct gcgttatccc ctgattctgt ggataaccgt      4680
attaccgcct ttgagtgagc tgataccgct cgccgcagcc gaacgaccga gcgcagcgag      4740
tcagtgagcg aggaagcgga agagcgcctg atgcggtatt ttctccttac gcatctgtgc      4800
ggtatttcac accgcatatg gtgcactctc agtacaatct gctctgatgc cgcatagtta      4860
agccagtaat cgaattcaag cttgtcgact cgaagatcca ataacttcgt atagcataca      4920
ttatacgaag ttataagtac tgaattcgga tctgggcgtg gttaagggtg ggaaagaata      4980
tataaggtgg gggtcttatg tagttttgta tctgttttgc agcagccgcc gccgccatga      5040
gcaccaactc gtttgatgga agcattgtga gctcatattt gacaacgcgc atgcccccat      5100
gggccggggt gcgtcagaat gtgatgggct ccagcattga tggtcgcccc gtcctgcccg      5160
caaactctac taccttgacc tacgagaccg tgtctggaac gccgttggag actgcagcct      5220
ccgccgccgc ttcagccgct gcagccaccg cccgcggat tgtgactgac tttgctttcc       5280
tgagcccgct tgcaagcagt gcagcttccc gttcatccgc ccgcgatgac aagttgacgg      5340
ctcttttggc acaattggat tctttgaccc gggaacttaa tgtcgtttct cagcagctgt      5400
tggatctgcg ccagcaggtt tctgccctga aggcttcctc ccctcccaat gcggtttaaa      5460
acataaataa aaaaccagac tctgtttgga tttggatcaa gcaagtgtct tgctgtcttt      5520
atttaggggt tttgcgcgcg cggtaggccc gggaccagcg gtctcggtcg ttgagggtcc      5580
tgtgtatttt ttccaggacg tggtaaaggt gactctggat gttcagatac atgggcataa      5640
gcccgtctct ggggtggagg tagcaccact gcagagcttc atgctgcggg gtggtgttgt      5700
agatgatcca gtcgtagcag gagcgctggg cgtggtgcct aaaaatgtct tcagtagca       5760 agctgattgc caggggcagg cccttggtgt aagtgtttac aaagcggtta agctgggatg      5820
ggtgcatacg tggggatatg agatgcatct tggactgtat ttttaggttg gctatgttcc      5880
```

```
cagccatatc cctccgggga ttcatgttgt gcagaaccac cagcacagtg tatccggtgc    5940
acttgggaaa tttgtcatgt agcttagaag gaaatgcgtg gaagaacttg gagacgccct    6000
tgtgacctcc aagattttcc atgcattcgt ccataatgat ggcaatgggc ccacgggcgg    6060
cggcctgggc gaagatattt ctgggatcac taacgtcata gttgtgttcc aggatgagat    6120
cgtcataggc cattttaca aagcgcgggc ggagggtgcc agactgcggt ataatggttc    6180
catccggccc aggggcgtag ttaccctcac agatttgcat ttcccacgct ttgagttcag    6240 atgggggat catgtctacc tgcggggcga tgaagaaaac ggtttccggg gtaggggaga    6300
tcagctggga agaaagcagg ttcctgagca gctgcgactt accgcagccg gtgggcccgt    6360
aaatcacacc tattaccggg tgcaactggt agttaagaga gctgcagctg ccgtcatccc    6420
tgagcagggg ggccacttcg ttaagcatgt ccctgactcg catgttttcc ctgaccaaat    6480
ccgccagaag gcgctcgccg cccagcgata gcagttcttg caaggaagca aagttttca    6540 acggtttgag accgtccgcc gtaggcatgc ttttgagcgt ttgaccaagc agttccaggc    6600
ggtcccacag ctcggtcacc tgctctacgg catctcgatc cagcatatct cctcgtttcg    6660
cgggttgggg cggctttcgc tgtacggcag tagtcggtgc tcgtccagac gggccagggt    6720
catgtctttc cacgggcgca gggtcctcgt cagcgtagtc tgggtcacgg tgaaggggtg    6780
cgctccgggc tgcgcgctgg ccagggtgcg cttgaggctg gtcctgctgg tgctgaagcg    6840
ctgccggtct tcgccctgcg cgtcggccag gtagcatttg accatggtgt catagtccag    6900
cccctccgcg gcgtggccct ggcgcgcag cttgcccttg gaggaggcgc cgcacgaggg    6960
gcagtgcaga cttttgaggg cgtagagctt gggcgcgaga aataccgatt ccggggagta    7020
ggcatccgcg ccgcaggccc cgcagacggt ctcgcattcc acgagccagg tgagctctgg    7080
ccgttcgggg tcaaaaacca ggtttccccc atgcttttg atgcgtttct tacctctggt    7140
ttccatgagc cggtgtccac gctcggtgac gaaaaggctg tccgtgtccc cgtatacaga    7200
cttgagaggc ctgtcctcga gcggtgttcc gcggtcctcc tcgtatagaa actcggacca    7260
ctctgagaca aaggctcgcg tccaggccag cacgaaggag gctaagtggg aggggtagcg    7320
gtcgttgtcc actaggggt ccactcgctc caggtgtga agacacatgt cgccctcttc    7380
ggcatcaagg aaggtgattg gtttgtaggt gtaggccacg tgaccgggtg ttcctgaagg    7440
ggggctataa aaggggtgg gggcgcgttc gtcctcactc tcttccgcat cgctgtctgc    7500
gagggccagc tgttggggtg agtactccct ctgaaaagcg ggcatgactt ctgcgctaag    7560
attgtcagtt tccaaaaacg aggaggattt gatattcacc tggcccgcgg tgatgccttt    7620
gagggtggcc gcatccatct ggtcagaaaa gacaatcttt ttgttgtcaa gcttggtggc    7680
aaacgacccg tagagggcgt tggacagcaa cttggcgatg gagcgcaggg tttggttttt    7740
gtcgcgatcg gcgcgctcct tggccgcgat gtttagctgc acgtattcgc gcgcaacgca    7800
ccgccattcg ggaaagacgg tggtgcgctc gtcgggcacc aggtgcacgc gccaaccgcg    7860
gttgtgcagg gtgacaaggt caacgctggt ggctacctct ccgcgtaggc gctcgttggt    7920
ccagcagagg cggccgccct tgcgcgagca gaatggcggt aggggggtcta gctgcgtctc    7980 gtccgggggg tctgcgtcca cggtaaagac cccgggcagc aggcgcgcgt cgaagtagtc    8040
tatcttgcat ccttgcaagt ctagcgcctg ctgccatgcg cgggcggcaa gcgcgcgctc    8100
gtatgggttg agtgggggac ccatggcat gggtgggtg agcgcggagg cgtacatgcc    8160
gcaaatgtcg taaacgtaga ggggctctct gagtattcca agatatgtag ggtagcatct    8220
tccaccgcgg atgctggcgc gcacgtaatc gtatagttcg tgcgagggag cgaggaggtc    8280
```

```
gggaccgagg ttgctacggg cgggctgctc tgctcggaag actatctgcc tgaagatggc    8340
atgtgagttg gatgatatgg ttggacgctg gaagacgttg aagctggcgt ctgtgagacc    8400
taccgcgtca cgcacgaagg aggcgtagga gtcgcgcagc ttgttgacca gctcggcggt    8460
gacctgcacg tctagggcgc agtagtccag ggtttccttg atgatgtcat acttatcctg    8520 tcccttttt ttccacagct cgcggttgag gacaaactct tcgcggtctt tccagtactc    8580
ttggatcgga aacccgtcgg cctccgaacg gtaagagcct agcatgtaga actggttgac    8640
ggcctggtag gcgcagcatc ccttttctac gggtagcgcg tatgcctgcg cggccttccg    8700
gagcgaggtg tgggtgagcg caaaggtgtc cctgaccatg actttgaggt actggtattt    8760
gaagtcagtg tcgtcgcatc cgccctgctc ccagagcaaa aagtccgtgc gcttttgga    8820 acgcggattt ggcagggcga aggtgacatc gttgaagagt atctttcccg cgcgaggcat    8880
aaagttgcgt gtgatgcgga agggtcccgg cacctcggaa cggttgttaa ttacctgggc    8940
ggcgagcacg atctcgtcaa agccgttgat gttgtggccc acaatgtaaa gttccaagaa    9000
gcgcgggatg cccttgatgg aaggcaattt tttaagttcc tcgtaggtga gctcttcagg    9060
ggagctgagc ccgtgctctg aaagggccca gtctgcaaga tgagggttgg aagcgacgaa    9120
tgagctccac aggtcacggg ccattagcat ttgcaggtgg tcgcgaaagg tcctaaactg    9180
gcgacctatg gccattttt ctggggtgat gcagtagaag gtaagcgggt cttgttccca    9240
gcggtcccat ccaaggttcg cggctaggtc tcgcgcggca gtcactagag gctcatctcc    9300
gccgaacttc atgaccagca tgaagggcac gagctgcttc ccaaaggccc ccatccaagt    9360
ataggtctct acatcgtagg tgacaaagag acgctcggtg cgaggatgcg agccgatcgg    9420
gaagaactgg atctcccgcc accaattgga ggagtggcta ttgatgtggt gaaagtagaa    9480
gtccctgcga cgggccgaac actcgtgctg gcttttgtaa aaacgtgcgc agtactggca    9540
gcggtgcacg ggctgtacat cctgcacgag gttgacctga cgaccgcgca caaggaagca    9600
gagtgggaat ttgagcccct cgcctggcgg gtttggctgg tggtcttcta cttcggctgc    9660
ttgtccttga ccgtctggct gctcgagggg agttacggtg gatcggacca ccacgccgcg    9720
cgagcccaaa gtccagatgt ccgcgcgcgg cggtcggagc ttgatgacaa catcgcgcag    9780
atgggagctg tccatggtct ggagctcccg cggcgtcagg tcaggcggga gctcctgcag    9840
gtttacctcg catagacggg tcagggcgcg ggctagatcc aggtgatacc taatttccag    9900
gggctggttg gtggcggcgt cgatggcttg caagaggccg catccccgcg gcgcgactac    9960
ggtaccgcgc ggcgggcggt gggccgcggg ggtgtccttg gatgatgcat ctaaaagcgg   10020
tgacgcgggc gagcccccgg aggtaggggg ggctccggac ccgccgggag aggggggcagg   10080 ggcacgtcgg cgccgcgcgc gggcaggagc tggtgctgcg cgcgtaggtt gctggcgaac   10140
gcgacgacgc ggcggttgat ctcctgaatc tggcgcctct gcgtgaagac gacgggcccg   10200
gtgagcttga gcctgaaaga gagttcgaca gaatcaattt cggtgtcgtt gacggcggcc   10260
tggcgcaaaa tctcctgcac gtctcctgag ttgtcttgat aggcgatctc ggccatgaac   10320
tgctcgatct cttcctcctg gagatctccg cgtccggctc gctccacggt ggcggcgagg   10380
tcgttggaaa tgcgggccat gagctgcgag aaggcgttga ggcctccctc gttccagacg   10440
cggctgtaga ccacgccccc ttcggcatcg cgggcgcgca tgaccacctg cgcgagattg   10500
agctccacgt gccgggcgaa gacggcgtag tttcgcaggc gctgaaagag gtagttgagg   10560
gtggtggcgg tgtgttctgc cacgaagaag tacataaccc agcgtcgcaa cgtggattcg   10620
```

-continued

```
ttgatatccc ccaaggcctc aaggcgctcc atggcctcgt agaagtccac ggcgaagttg   10680
aaaaactggg agttgcgcgc cgacacggtt aactcctcct ccagaagacg gatgagctcg   10740
gcgacagtgt cgcgcacctc gcgctcaaag gctacagggg cctcttcttc ttcttcaatc   10800
tcctcttcca taagggcctc cccttcttct tcttctggcg gcggtggggg agggggggaca   10860 cggcggcgac gacggcgcac cgggaggcgg tcgacaaagc gctcgatcat ctccccgcgg   10920
cgacggcgca tggtctcggt gacgcgcggg ccgttctcgc gggggcgcag ttggaagacg   10980
ccgcccgtca tgtcccggtt atgggttggc ggggggctgc catgcggcag ggatacggcg   11040
ctaacgatgc atctcaacaa ttgttgtgta ggtactccgc cgccgaggga cctgagcgag   11100
tccgcatcga ccggatcgga aaacctctcg agaaaggcgt ctaaccagtc acagtcgcaa   11160
ggtaggctga gcaccgtggc gggcggcagc gggcggcggt cggggttgtt tctggcggag   11220
gtgctgctga tgatgtaatt aaagtaggcg gtcttgagac ggcggatggt cgacagaagc   11280
accatgtcct tgggtccggc ctgctgaatg cgcaggcggt cggccatgcc ccaggcttcg   11340
ttttgacatc ggcgcaggtc tttgtagtag tcttgcatga gcctttctac cggcacttct   11400
tcttctcctt cctcttgtcc tgcatctctt gcatctatcg ctgcggcggc ggcggagttt   11460
ggccgtaggt ggcgccctct tcctcccatg cgtgtgaccc cgaagcccct catcggctga   11520
agcagggcta ggtcggcgac aacgcgctcg gctaatatgg cctgctgcac ctgcgtgagg   11580
gtagactgga agtcatccat gtccacaaag cggtggtatg cgcccgtgtt gatggtgtaa   11640
gtgcagttgg ccataacgga ccagttaacg gtctggtgac ccggctgcga gagctcggtg   11700
tacctgagac gcgagtaagc cctcgagtca aatacgtagt cgttgcaagt ccgcaccagg   11760
tactggtatc ccaccaaaaa gtgcggcggc ggctggcggt agaggggcca gcgtagggtg   11820
gccggggctc cggggggcgag atcttccaac ataaggcgat gatatccgta gatgtacctg   11880
gacatccagg tgatgccggc ggcggtggtg gaggcgcgcg gaaagtcgcg gacgcggttc   11940
cagatgttgc gcagcggcaa aaagtgctcc atggtcggga cgctctggcc ggtcaggcgc   12000
gcgcaatcgt tgacgctcta ccgtgcaaaa ggagagcctg taagcgggca ctcttccgtg   12060
gtctggtgga taaattcgca agggtatcat ggccgacgac cggggttcga gccccgtatc   12120
cggccgtccg ccgtgatcca tgcggttacc gcccgcgtgt cgaacccagg tgtgcgacgt   12180
cagacaacgg gggagtgctc cttttggctt cctccaggc gcggcggctg ctgcgctagc   12240 tttttttggcc actggccgcg cgcagcgtaa gcggttaggc tggaaagcga aagcattaag   12300
tggctcgctc cctgtagccg gagggttatt ttccaagggt tgagtcgcgg gaccccggt   12360 tcgagtctcg gaccggccgg actgcggcga acgggggttt gcctccccgt catgcaagac   12420
cccgcttgca aattcctccg gaaacaggga cgagcccctt ttttgctttt cccagatgca   12480
tccggtgctg cggcagatgc gccccctcc tcagcagcgg caagagcaag agcagcggca   12540
gacatgcagg gcaccctccc ctcctcctac cgcgtcagga ggggcgacat ccgcggttga   12600
cgcggcagca gatggtgatt acgaacccc gcggcgccgg gccggcact acctggactt   12660 ggaggagggc gagggcctgg cgcggctagg agcgccctct cctgagcggt acccaagggt   12720
gcagctgaag cgtgatacgc gtgaggcgta cgtgccgcgg cagaacctgt ttcgcgaccg   12780
cgagggagag gagcccgagg agatgcggga tcgaaagttc cacgcagggc gcgagctgcg   12840
gcatggcctg aatcgcgagc ggttgctgcg cgaggaggac tttgagcccg acgcgcgaac   12900
cgggattagt cccgcgcgcg cacacgtggc ggccgccgac ctggtaaccg catacgagca   12960
gacggtgaac caggagatta actttcaaaa aagctttaac aaccacgtgc gtacgcttgt   13020
```

```
ggcgcgcgag gaggtggcta taggactgat gcatctgtgg gactttgtaa gcgcgctgga    13080
gcaaaaccca aatagcaagc cgctcatggc gcagctgttc cttatagtgc agcacagcag    13140
ggacaacgag gcattcaggg atgcgctgct aaacatagta gagcccgagg gccgctggct    13200
gctcgatttg ataaacatcc tgcagagcat agtggtgcag gagcgcagct tgagcctggc    13260
tgacaaggtg gccgccatca actattccat gcttagcctg ggcaagtttt acgcccgcaa    13320
gatataccat accccttacg ttcccataga caaggaggta aagatcgagg ggttctacat    13380
gcgcatggcg ctgaaggtgc ttaccttgag cgacgacctg ggcgtttatc gcaacgagcg    13440
catccacaag gccgtgagcg tgagccggcg gcgcgagctc agcgaccgcg agctgatgca    13500
cagcctgcaa agggccctgg ctggcacggg cagcggcgat agagaggccg agtcctactt    13560
tgacgcgggc gctgacctgc gctgggcccc aagccgacgc gccctggagg cagctggggc    13620
cggacctggg ctggcggtgg cacccgcgcg cgctggcaac gtcggcggcg tggaggaata    13680
tgacgaggac gatgagtacg agccagagga cggcgagtac taagcggtga tgtttctgat    13740
cagatgatgc aagacgcaac ggacccggcg gtgcgggcgg cgctgcagag ccagccgtcc    13800
ggccttaact ccacggacga ctggcgccag gtcatggacc gcatcatgtc gctgactgcg    13860
cgcaatcctg acgcgttccg gcagcagccg caggccaacc ggctctccgc aattctggaa    13920
gcggtggtcc cggcgcgcgc aaaccccacg cacgagaagg tgctggcgat cgtaaacgcg    13980
ctggccgaaa acagggccat ccggcccgac gaggccggcc tggtctacga cgcgctgctt    14040
cagcgcgtgg ctcgttacaa cagcggcaac gtgcagacca acctggaccg gctggtgggg    14100
gatgtgcgcg aggccgtggc gcagcgtgag cgcgcgcagc agcagggcaa cctgggctcc    14160
atggttgcac taaacgcctt cctgagtaca cagcccgcca acgtgccgcg gggacaggag    14220
gactacacca actttgtgag cgcactgcgg ctaatggtga ctgagacacc gcaaagtgag    14280
gtgtaccagt ctgggccaga ctattttttc cagaccagta gacaaggcct gcagaccgta    14340
aacctgagcc aggcttttcaa aaacttgcag gggctgtggg gggtgcgggc tcccacaggc    14400
gaccgcgcga ccgtgtctag cttgctgacg cccaactcgc gcctgttgct gctgctaata    14460
gcgcccttca cggacagtgg cagcgtgtcc cgggacacat acctaggtca cttgctgaca    14520
ctgtaccgcg aggccatagg tcaggcgcat gtggacgagc atactttcca ggagattaca    14580
agtgtcagcc gcgcgctggg gcaggaggac acgggcagcc tggaggcaac cctaaactac    14640
ctgctgacca accggcggca gaagatcccc tcgttgcaca gtttaaacag cgaggaggag    14700
cgcattttgc gctacgtgca gcagagcgtg agccttaacc tgatgcgcga cggggtaacg    14760
cccagcgtgg cgctggacat gaccgcgcgc aacatggaac cgggcatgta tgcctcaaac    14820
cggccgttta tcaaccgcct aatggactac ttgcatcgcg cggccgccgt gaaccccgag    14880
tatttcacca atgccatctt gaacccgcac tggctaccgc ccctggtttt ctacaccggg    14940
ggattcgagg tgcccgaggg taacgatgga ttcctctggg acgacataga cgacagcgtg    15000 ttttcccgc aaccgcagac cctgctagag ttgcaacagc gcgagcaggc agaggcggcg    15060
ctgcgaaagg aaagcttccg caggccaagc agcttgtccg atctaggcgc tgcggccccg    15120
cggtcagatg ctagtagccc atttccaagc ttgataggt ctcttaccag cactcgcacc    15180
acccgcccgc gcctgctggg cgaggaggag tacctaaaca actcgctgct gcagccgcag    15240
cgcgaaaaaa acctgcctcc ggcatttccc aacaacggga tagagagcct agtggacaag    15300
atgagtagat ggaagacgta cgcgcaggag cacagggacg tgccaggccc cgcgcccgcc    15360
```

```
acccgtcgtc aaaggcacga ccgtcagcgg ggtctggtgt gggaggacga tgactcggca    15420
gacgacagca gcgtcctgga tttgggaggg agtggcaacc cgtttgcgca ccttcgcccc    15480
aggctgggga gaatgtttta aaaaaaaaaa agcatgatgc aaaataaaaa actcaccaag    15540
gccatggcac cgagcgttgg ttttcttgta ttcccttag tatgcggcgc gcggcgatgt     15600
atgaggaagg tcctcctccc tcctacgaga gtgtggtgag cgcggcgcca gtggcggcgg    15660
cgctgggttc tcccttcgat gctcccctgg acccgccgtt tgtgcctccg cggtacctgc    15720
ggcctaccgg ggggagaaac agcatccgtt actctgagtt ggcacccta ttcgacacca     15780 cccgtgtgta cctggtggac aacaagtcaa cggatgtggc atccctgaac taccagaacg    15840
accacagcaa ctttctgacc acggtcattc aaaacaatga ctacagcccg ggggaggcaa    15900
gcacacagac catcaatctt gacgaccggt cgcactgggg cggcgacctg aaaaccatcc    15960
tgcataccaa catgccaaat gtgaacgagt tcatgtttac caataagttt aaggcgcggg    16020
tgatggtgtc gcgcttgcct actaaggaca atcaggtgga gctgaaatac gagtgggtgg    16080
agttcacgct gcccgagggc aactactccg agaccatgac catagacctt atgaacaacg    16140
cgatcgtgga gcactacttg aaagtgggca gacagaacgg ggttctggaa agcgacatcg    16200
gggtaaagtt tgacacccgc aacttcagac tggggtttga ccccgtcact ggtcttgtca    16260
tgcctggggt atatacaaac gaagccttcc atccagacat cattttgctg ccaggatgcg    16320
gggtggactt cacccacagc cgcctgagca acttgttggg catccgcaag cggcaaccct    16380
tccaggaggg ctttaggatc acctacgatg atctggaggg tggtaacatt cccgcactgt    16440
tggatgtgga cgcctaccag gcgagcttga aagatgacac cgaacagggc gggggtggcg    16500
caggcggcag caacagcagt ggcagcggcg cggaagagaa ctccaacgcg gcagccgcgg    16560
caatgcagcc ggtggaggac atgaacgatc atgccattcg cggcgacacc tttgccacac    16620
gggctgagga gaagcgcgct gaggccgaag cagcggccga agctgccgcc cccgctgcgc    16680
aacccgaggt cgagaagcct cagaagaaac cggtgatcaa accctgaca gaggacagca    16740 agaaacgcag ttacaaccta ataagcaatg acagcaccct cacccagtac cgcagctggt    16800
accttgcata caactacggc gaccctcaga ccggaatccg ctcatggacc ctgctttgca    16860
ctcctgacgt aacctgcggc tcggagcagg tctactggtc gttgccagac atgatgcaag    16920
accccgtgac cttccgctcc acgcgccaga tcagcaactt tccggtggtg ggcgccgagc    16980
tgttgcccgt gcactccaag agcttctaca acgaccaggc cgtctactcc caactcatcc    17040
gccagtttac ctctctgacc cacgtgttca atcgcttctcc cgagaaccag attttggcgc    17100
gcccgccagc ccccaccatc accaccgtca gtgaaaacgt tcctgctctc acagatcacg    17160
ggacgctacc gctgcgcaac agcatcggag gagtccagcg agtgaccatt actgacgcca    17220
gacgccgcac ctgcccctac gtttacaagg ccctgggcat agtctcgccg cgcgtcctat    17280
cgagccgcac tttttgagca agcatgtcca tccttatatc gcccagcaat aacacaggct    17340
ggggcctgcg cttcccaagc aagatgtttg gcggggccaa gaagcgctcc gaccaacacc    17400
cagtgcgcgt gcgcgggcac taccgcgcgc cctggggcgc gcacaaacgc ggccgcactg    17460
ggcgcaccac cgtcgatgac gccatcgacg cggtggtgga ggaggcgcgc aactacgcg     17520 ccacgccgcc accagtgtcc acagtggacg cggccattca daccgtggtg gcggagccc     17580 ggcgctatgc taaaatgaag agacggcgga ggcgcgtagc acgtcgccac cgccgccgac    17640
ccggcactgc cgcccaacgc gcggcggcgg ccctgcttaa ccgcgcacgt cgcaccggcc    17700
gacgggcggc catgcgggcc gctcgaaggc tggccgcggg tattgtcact gtgccccca    17760
```

```
ggtccaggcg acgagcggcc gccgcagcag ccgcggccat tagtgctatg actcagggtc   17820 gcagggcaa cgtgtattgg gtgcgcgact cggttagcgg cctgcgcgtg cccgtgcgca   17880 cccgccccc gcgcaactag attgcaagaa aaaactactt agactcgtac tgttgtatgt   17940
atccagcggc ggcggcgcgc aacgaagcta tgtccaagcg caaaatcaaa gaagagatgc   18000
tccaggtcat cgcgccggag atctatggcc ccccgaagaa ggaagagcag gattacaagc   18060
cccgaaagct aaagcgggtc aaaaagaaaa agaaagatga tgatgatgaa cttgacgacg   18120
aggtggaact gctgcacgct accgcgccca ggcgacgggt acagtggaaa ggtcgacgcg   18180
taaaacgtgt tttgcgaccc ggcaccaccg tagtctttac gcccggtgag cgctccaccc   18240
gcacctacaa gcgcgtgtat gatgaggtgt acggcgacga ggacctgctt gagcaggcca   18300
acgagcgcct cggggagttt gcctacgaaa gcggcataa ggacatgctg gcgttgccgc    18360
tggacgaggg caacccaaca cctagcctaa agcccgtaac actgcagcag gtgctgcccg   18420
cgcttgcacc gtccgaagaa aagcgcggcc taaagcgcga gtctggtgac ttggcaccca   18480
ccgtgcagct gatggtaccc aagcgccagc gactggaaga tgtcttggaa aaaatgaccg   18540
tggaacctgg gctggagccc gaggtccgcg tgcggccaat caagcaggtg gcgccgggac   18600
tgggcgtgca gaccgtggac gttcagatac ccactaccag tagcaccagt attgccaccg   18660
ccacagaggg catggagaca caaacgtccc cggttgcctc agcggtggcg gatgccgcgg   18720
tgcaggcggt cgctgcggcc gcgtccaaga cctctacgga ggtgcaaacg gacccgtgga   18780
tgtttcgcgt ttcagccccc cggcgcccgc gcggttcgag gaagtacggc gccgccagcg   18840
cgctactgcc cgaatatgcc ctacatcctt ccattgcgcc taccccggc tatcgtggct    18900 acacctaccg ccccagaaga cgagcaacta cccgacgccg aaccaccact ggaacccgcc   18960
gccgccgtcg ccgtcgccag cccgtgctgg ccccgatttc cgtgcgcagg gtggctcgcg   19020
aaggaggcag gaccctggtg ctgccaacag cgcgctacca ccccagcatc gtttaaaagc   19080
cggtctttgt ggttcttgca gatatggccc tcacctgccg cctccgtttc ccggtgccgg   19140
gattccgagg aagaatgcac cgtaggaggg gcatggccgg ccacggcctg acgggcggca   19200
tgcgtcgtgc gcaccaccgg cggcggcgcg cgtcgcaccg tcgcatgcgc ggcggtatcc   19260 tgccctcct tattccactg atcgccgcgg cgattggcgc cgtgcccgga attgcatccg    19320
tggccttgca ggcgcagaga cactgattaa aaacaagttg catgtggaaa atcaaaata    19380 aaaagtctgg actctcacgc tcgcttggtc ctgtaactat tttgtagaat ggaagacatc   19440
aactttgcgt ctctggcccc gcgacacggc tcgcgcccgt tcatgggaaa ctggcaagat   19500
atcggcacca gcaatatgag cggtggcgcc ttcagctggg gctcgctgtg gagcggcatt   19560
aaaaatttcg gttccaccgt taagaactat ggcagcaagg cctggaacag cagcacaggc   19620
cagatgctga gggataagtt gaaagagcaa aatttccaac aaaaggtggt agatggcctg   19680
gcctctggca ttagcgggt ggtggacctg gccaaccagg cagtgcaaaa taagattaac   19740
agtaagcttg atccccgccc tcccgtagag gagcctccac cggccgtgga gacagtgtct   19800 ccagagggc gtggcgaaaa gcgtccgcgc cccgacaggg aagaaactct ggtgacgcaa    19860
atagacgagc ctccctcgta cgaggaggca ctaaagcaag gcctgccac cacccgtccc   19920 atcgcgccca tggctaccgg agtgctgggc cagcacacac ccgtaacgct ggacctgcct   19980 cccccgccg acacccagca gaaacctgtg ctgccaggcc cgaccgccgt tgttgtaacc   20040
cgtcctagcc gcgcgtccct gcgccgcgcc gccagcggtc cgcgatcgtt gcggcccgta   20100
```

-continued

```
gccagtggca actggcaaag cacactgaac agcatcgtgg gtctgggggt gcaatccctg   20160
aagcgccgac gatgcttctg aatagctaac gtgtcgtatg tgtgtcatgt atgcgtccat   20220
gtcgccgcca gaggagctgc tgacaagttt gtacaaaaaa gctgaacgag aaacgtaaaa   20280
tgatataaat atcaatatat taaattagat tttgcataaa aaacagacta cataatactg   20340
taaaacacaa catatccagt cactatgccg ccgcgcgccc gctttccaag atggctaccc   20400
cttcgatgat gccgcagtgg tcttacatgc acatctcggg ccaggacgcc tcggagtacc   20460
tgagccccgg gctggtgcag tttgcccgcg ccaccgagac gtacttcagc ctgaataaca   20520
agtttagaaa ccccacggtg gcgcctacgc acgacgtgac cacagaccgg tcccagcgtt   20580
tgacgctgcg gttcatccct gtggaccgtg aggatactgc gtactcgtac aaggcgcggt   20640
tcaccctagc tgtgggtgat aaccgtgtgc tggacatggc ttccacgtac tttgacatcc   20700
gcggcgtgct ggacaggggc cctacttta  agccctactc tggcactgcc tacaacgccc   20760
tggctcccaa gggtgcccca aatccttgcg aatgggatga agctgctact gctcttgaaa   20820
taaacctaga agaagaggac gatgacaacg aagacgaagt agacgagcaa gctgagcagc   20880
aaaaaactca cgtatttggg caggcgcctt attctggtat aaatattaca aaggagggta   20940
ttcaaatagg tgtcgaaggt caaacaccta atatgccga taaaacatt  caacctgaac   21000
ctcaaatagg agaatctcag tggtacgaaa ctgaaattaa tcatgcagct gggagagtcc   21060
ttaaaaagac taccccaatg aaaccatgtt acgttcata  tgcaaaaccc acaaatgaaa   21120
atggagggca aggcattctt gtaaagcaac aaaatggaaa gctagaaagt caagtggaaa   21180
tgcaattttt ctcaactact gaggcgaccg caggcaatgg tgataacttg actcctaaag   21240
tggtattgta cagtgaagat gtagatatag aaccccaga  cactcatatt tcttacatgc   21300
ccactattaa ggaaggtaac tcacgagaac taatgggcca acaatctatg cccaacaggc   21360
ctaattacat tgcttttagg gacaatttta ttggtctaat gtattacaac agcacgggta   21420
atatgggtgt tctggcgggc caagcatcgc agttgaatgc tgttgtagat ttgcaagaca   21480
gaaacacaga gctttcatac cagcttttgc ttgattccat tggtgataga accaggtact   21540
tttctatgtg gaatcaggct gttgacagct atgatccaga tgttagaatt attgaaaatc   21600
atggaactga agatgaactt ccaaattact gctttccact gggaggtgtg attaatacag   21660
agactcttac caaggtaaaa cctaaaacag gtcaggaaaa tggatgggaa aaagatgcta   21720
cagaattttc agataaaaat gaaataagag ttggaaataa ttttgccatg gaaatcaatc   21780
taaatgccaa cctgtggaga aatttcctgt actccaacat agcgctgtat ttgcccgaca   21840
agctaaagta cagtccttcc aacgtaaaaa tttctgataa cccaaacacc tacgactaca   21900
tgaacaagcg agtggtggct cccgggttag tggactgcta cattaacctt ggagcacgct   21960
ggtcccttga ctatatggac aacgtcaacc catttaacca ccaccgcaat gctggcctgc   22020
gctaccgctc aatgttgctg ggcaatggtc gctatgtgcc cttccacatc caggtgcctc   22080
agaagttctt tgccattaaa aacctccttc tcctgccggg ctcatacacc tacgagtgga   22140
acttcaggaa ggatgttaac atggttctgc agagctccct aggaaatgac ctaagggttg   22200
acggagccag cattaagttt gatagcattt gcctttacgc caccttcttc cccatggccc   22260
acaacaccgc ctccacgctt gaggccatgc ttagaaacga caccaacgac cagtcctta   22320
acgactatct ctccgccgcc aacatgctct accctatacc cgccaacgct accaacgtgc   22380
ccatatccat ccccgcccgc aactgggcgg ctttccgcgg ctgggccttc acgcgcctta   22440
agactaagga aaccccatca ctgggctcgg gctacgaccc ttattacacc tactctggct   22500
```

```
ctataccctc cctagatgga acctttttacc tcaaccacac cttttaagaag gtggccatta   22560 cctttgactc ttctgtcagc tggcctggca atgaccgcct gcttacccccc aacgagtttg   22620 aaattaagcg ctcagttgac ggggagggtt acaacgttgc ccagtgtaac atgaccaaag   22680
actggttcct ggtacaaatg ctagctaact acaacattgg ctaccagggc ttctatatcc   22740
cagagagcta caaggaccgc atgtactcct tctttagaaa cttccagccc atgagccgtc   22800
aggtggtgga tgatactaaa tacaaggact accaacaggt gggcatccta caccaacaca   22860
acaactctgg atttgttggc taccttgccc ccaccatgcg cgaaggacag gcctaccctg   22920
ctaacttccc ctatccgctt ataggcaaga ccgcagttga cagcattacc cagaaaaagt   22980
ttctttgcga tcgcaccctt tggcgcatcc cattctccag taactttatg tccatgggcg   23040
cactcacaga cctgggccaa aaccttctct acgccaactc cgcccacgcg ctagacatga   23100
cttttgaggt ggatcccatg gacgagccca cccttcttta tgttttgttt gaagtctttg   23160
acgtggtccg tgtgcaccgg ccgcaccgcg cgtcatcga aaccgtgtac ctgcgcacgc   23220
ccttctcggc cggcaacgcc acaacataaa gaagcaagca acatcaacaa cagctgccgc   23280
catgggctcc agtgagcagg aactgaaagc cattgtcaaa gatcttggtt gtgggccata   23340
ttttttgggc acctatgaca agcgctttcc aggctttgtt tctccacaca agctcgcctg   23400
cgccatagtc aatacggccg gtcgcgagac tggggcgta cactggatgg cctttgcctg   23460
gaacccgcac tcaaaaacat gctacctctt tgagcccttt ggcttttctg accagcgact   23520
caagcaggtt taccagtttg agtacgagtc actcctgcgc cgtagcgcca ttgcttcttc   23580
ccccgaccgc tgtataacgc tggaaaagtc cacccaaagc gtacagggc ccaactcggc   23640 cgcctgtgga ctattctgct gcatgtttct ccacgccttt gccaactggc cccaaactcc   23700
catggatcac aaccccacca tgaacctttat taccggggta cccaactcca tgctcaacag   23760
tccccaggta cagcccaccc tgcgtcgcaa ccaggaacag ctctacagct tcctggagcg   23820
ccactcgccc tacttccgca gccacagtgc gcagattagg agcgccactt cttttttgtca   23880 cttgaaaaac atgtaaaaat aatgtactag agacactttc aataaaggca aatgctttta   23940
tttgtacact ctcgggtgat tatttacccc caccctttgcc gtctgcgccg tttaaaaatc   24000 aaagggggttc tgccgcgcat cgctatgcgc cactggcagg gacacgttgc gatactggtg   24060
tttagtgctc cacttaaact caggcacaac catccgcggc agctcggtga agttttcact   24120
ccacaggctg cgcaccatca ccaacgcgtt tagcaggtcg ggcgccgata tcttgaagtc   24180
gcagttgggg cctccgccct gcgcgcgcga gttgcgatac acagggttgc agcactggaa   24240
cactatcagc gccgggtggt gcacgctggc cagcacgctc ttgtcggaga tcagatccgc   24300
gtccaggtcc tccgcgttgc tcagggcgaa cggagtcaac tttggtagct gccttcccaa   24360
aaagggcgcg tgcccaggct ttgagttgca ctcgcaccgt agtggcatca aaggtgacc   24420 gtgcccggtc tgggcgttag gatacagcgc ctgcataaaa gccttgatct gcttaaaagc   24480
cacctgagcc tttgcgcctt cagagaagaa catgccgcaa gacttgccgg aaaactgatt   24540
ggccggacag gccgcgtcgt gcacgcagca ccttgcgtcg gtgttggaga tctgcaccac   24600
atttcggccc caccggttct tcacgatctt ggccttgcta gactgctcct tcagcgcgcg   24660
ctgcccgttt tcgctcgtca catccatttc aatcacgtgc tccttattta tcataatgct   24720
tccgtgtaga cacttaagct cgccttcgat ctcagcgcag cggtgcagcc acaacgcgca   24780
gcccgtgggc tcgtgatgct tgtaggtcac ctctgcaaac gactgcaggt acgcctgcag   24840
```

```
gaatcgcccc atcatcgtca caaaggtctt gttgctggtg aaggtcagct gcaacccgcg   24900
gtgctcctcg ttcagccagg tcttgcatac ggccgccaga gcttccactt ggtcaggcag   24960
tagtttgaag ttcgccttta gatcgttatc cacgtggtac ttgtccatca gcgcgcgcgc   25020
agcctccatg cccttctccc acgcagacac gatcggcaca ctcagcgggt tcatcaccgt   25080
aatttcactt tccgcttcgc tgggctcttc ctcttcctct tgcgtccgca taccacgcgc   25140
cactgggtcg tcttcattca gccgccgcac tgtgcgctta cctcctttgc catgcttgat   25200
tagcaccggt gggttgctga aacccaccat ttgtagcgcc acatcttctc tttcttcctc   25260
gctgtccacg attacctctg gtgatggcgg gcgctcgggc ttgggagaag gcgcttctt    25320
tttcttcttg ggcgcaatgg ccaaatccgc cgccgaggtc gatggccgcg ggctgggtgt   25380
gcgcggcacc agcgcgtctt gtgatgagtc ttcctcgtcc tcggactcga tacgccgcct   25440
catccgcttt tttgggggcg cccggggagg cggcggcgac ggggacgggg acgacacgtc   25500
ctccatggtt gggggacgtc gcgccgcacc gcgtccgcgc tcggggggtgg tttcgcgctg   25560
ctcctcttcc cgactggcca tttccttctc ctataggcag aaaaagatca tggagtcagt   25620
cgagaagaag gacagcctaa ccgcccccctc tgagttcgcc accaccgcct ccaccgatgc   25680
cgccaacgcg cctaccacct tccccgtcga ggcaccccg cttgaggagg aggaagtgat    25740
tatcgagcag gacccaggtt ttgtaagcga agacgacgag gaccgctcag taccaacaga   25800
ggataaaaag caagaccagg acaacgcaga ggcaaacgag gaacaagtcg ggcgggggga   25860
cgaaaggcat ggcgactacc tagatgtggg agacgacgtg ctgttgaagc atctgcagcg   25920
ccagtgcgcc attatctgcg acgcgttgca agagcgcagc gatgtgcccc tcgccatagc   25980
ggatgtcagc cttgcctacg aacgccacct attctcaccg cgcgtacccc ccaaacgcca   26040
agaaaacggc acatgcgagc ccaacccgcg cctcaacttc tacccccgtat ttgccgtgcc   26100
agaggtgctt gccacctatc acatcttttt ccaaaactgc aagataccccc tatcctgccg   26160
tgccaaccga agccgagcgg acaagcagct ggccttgcgg cagggcgctg tcatacctga   26220
tatcgcctcg ctcaacgaag tgccaaaaat ctttgagggt cttggacgcg acgagaagcg   26280
cgcggcaaac gctctgcaac aggaaaacag cgaaaatgaa agtcactctg gagtgttggt   26340
ggaactcgag ggtgacaacg cgcgcctagc cgtactaaaa cgcagcatcg aggtcaccca   26400
ctttgcctac ccggcactta acctacccccc caaggtcatg agcacagtca tgagtgagct   26460
gatcgtgcgc cgtgcgcagc ccctggagag ggatgcaaat ttgcaagaac aaacagagga   26520
gggcctaccc gcagttggcg acgagcagct agcgcgctgg cttcaaacgc gcgagcctgc   26580
cgacttggag gagcgacgca aactaatgat ggccgcagtg ctcgttaccg tggagcttga   26640
gtgcatgcag cggttctttg ctgacccgga gatgcagcgc aagctagagg aaacattgca   26700
ctacacctttt cgacagggct acgtacgcca ggcctgcaag atctccaacg tggagctctg   26760
caacctggtc tcctaccttg aattttgca cgaaaccgc cttgggcaaa acgtgcttca     26820
ttccacgctc aagggcgagg cgcgccgcga ctacgtccgc gactgcgttt acttatttct   26880
atgctacacc tggcagacgg ccatgggcgt ttggcagcag tgcttggagg agtgcaacct   26940
caaggagctg cagaaactgc taaagcaaaa cttgaaggac ctatgacgg ccttcaacga    27000
gcgctccgtg gccgcgcacc tggcggacat catttttcccc gaacgcctgc ttaaaaccct   27060
gcaacagggt ctgccagact tcaccagtca aagcatgttg cagaacttta ggaactttat   27120
cctagagcgc tcaggaatct tgcccgcgac ctgctgtgca cttcctagcg actttgtgcc   27180
cattaagtac cgcgaatgcc ctccgccgct ttggggccac tgctaccttc tgcagctagc   27240
```

```
caactacctt gcctaccact ctgacataat ggaagacgtg agcggtgacg gtctactgga   27300
gtgtcactgt cgctgcaacc tatgcacccc gcaccgctcc ctggtttgca attcgcagct   27360
gcttaacgaa agtcaaatta tcggtacctt tgagctgcag ggtccctcgc ctgacgaaaa   27420
gtccgcggct ccggggttga aactcactcc ggggctgtgg acgtcggctt accttcgcaa   27480
atttgtacct gaggactacc acgcccacga gattaggttc tacgaagacc aatcccgccc   27540
gccaaatgcg gagcttaccg cctgcgtcat tacccagggc cacattcttg gccaattgca   27600
agccatcaac aaagcccgcc aagagtttct gctacgaaag ggacgggggg tttacttgga   27660
cccccagtcc ggcgaggagc tcaacccaat ccccccgccg ccgcagccct atcagcagca   27720
gccgcgggcc cttgcttccc aggatggcac ccaaaaagaa gctgcagctg ccgccgccac   27780
ccacggacga ggaggaatac tgggacagtc aggcaggaga ggttttggac gaggaggagg   27840
aggacatgat ggaagactgg gagagcctag acgaggaagc ttccgaggtc aagaggtgt    27900 cagacgaaac accgtcaccc tcggtcgcat tcccctcgcc ggcgcccag aaatcggcaa    27960 ccggttccag catggctaca acctccgctc ctcaggcgcc gccggcactg cccgttcgcc   28020
gacccaaccg tagatgggac accactggaa ccagggccgg taagtccaag cagccgccgc   28080
cgttagccca agagcaacaa cagcgccaag gctaccgctc atggcgcggg cacaagaacg   28140
ccatagttgc ttgcttgcaa gactgtgggg gcaacatctc cttcgcccgc cgctttcttc   28200
tctaccatca cggcgtggcc ttcccccgta acatcctgca ttactaccgt catctctaca   28260
gcccatactg caccggcggc agcggcagcg gcagcaacag cagcggccac acagaagcaa   28320
aggcgaccgg atagcaagac tctgacaaag cccaagaaat ccacagcggc ggcagcagca   28380
ggaggaggag cgctgcgtct ggcgcccaac gaacccgtat cgaccgcga gcttagaaac    28440 aggattttc ccactctgta tgctatattt caacagagca ggggccaaga acaagagctg     28500
aaaataaaaa acaggtctct gcgatccctc acccgcagct gcctgtatca caaaagcgaa   28560
gatcagcttc ggcgcacgct ggaagacgcg gaggctctct tcagtaaata ctgcgcgctg   28620
actcttaagg actagtttcg cgcccttct caaatttaag cgcgaaaact acgtcatctc    28680
cagcggccac acccggcgcc agcacctgtc gtcagccca ttatgagcaa ggaaattccc     28740
acgccctaca tgtggagtta ccagccacaa atgggacttg cggctggagc tgcccaagac   28800
tactcaaccc gaataaacta catgagcgcg ggaccccaca tgatatcccg ggtcaacgga   28860
atccgcgccc accgaaaccg aattctcttg gaacaggcgg ctattaccac cacacctcgt   28920 aataaccta atccccgtag ttggcccgct gccctggtgt accaggaaag tcccgctccc     28980
accactgtgg tacttcccag agacgcccag gccgaagttc agatgactaa ctcaggggcg   29040
cagcttgcgg gcggctttcg tcacaggtgt cggtcgcccg ggcagggtat aactcacctg   29100
acaatcagag ggcgaggtat tcagctcaac gacgagtcgg tgagctcctc gcttggtctc   29160
cgtccggacg ggacatttca gatcggcggc gccggccgtc cttcattcac gcctcgtcag   29220
gcaatcctaa ctctgcagac ctcgtcctct gagccgcgct ctggaggcat ggaactctg    29280 caatttattg aggagtttgt gccatcggtc tactttaacc ccttctcggg acctcccggc   29340
cactatccgg atcaatttat tcctaacttt gacgcggtaa aggactcggc ggacggctac   29400
gactgaatgt taagtggaga ggcagagcaa ctgcgcctga acacctggt ccactgtcgc    29460 cgccacaagt gctttgcccg cgactccggt gagttttgct actttgaatt gcccgaggat   29520
catatcgagg gcccggcgca cggcgtccgg cttaccgccc agggagagct tgcccgtagc   29580
```

```
ctgattcggg agtttaccca gcgcccctg  ctagttgagc gggacagggg accctgtgtt  29640
ctcactgtga tttgcaactg tcctaacctt ggattacatc aagatcctct agttaattaa  29700
gaatatatac tgatatgtat acccgaagta tgtcaaaaag aggtgtgcta tgaagcagcg  29760
tattacagtg acagttgaca gcgacagcta tcagttgctc aaggcatata tgatgtcaat  29820
atctccggtc tggtaagcac aaccatgcag aatgaagccc gtcgtctgcg tgccgaacgc  29880
tggaaagcgg aaaatcagga agggatggct gaggtcgccc ggtttattga aatgaacggc  29940
tcttttgctg acgagaacag ggactggtga aatgcagttt aaggtttaca cctataaaag  30000
agagagccgt tatcgtctgt tgtggatgt  acagagtgat attattgaca cgcccgggcg  30060
acggatggta atcccctgg  ccagtgcacg tctgctgtca gataaagtct cccgtgaact  30120
ttacccggtg gtgcatatcg gggatgaaag ctggcgcatg atgaccaccg atatggccag  30180
tgtgccggtc tccgttatcg gggaagaagt ggctgatctc agccaccgcg aaaatgacat  30240
caaaaacgcc attaacctga tgttctgggg aatataaatg tcaggctccc ttatacacag  30300
ccagtctaga gtacccgggg atcttattcc ctttaactaa taaaaaaaaa taataaagca  30360
tcacttactt aaaatcagtt agcaaatttc tgtccagttt attcagcagc acctccttgc  30420
cctcctccca gctctggtat tgcagcttcc tcctggctgc aaactttctc cacaatctaa  30480
atggaatgtc agtttcctcc tgttcctgtc catccgcacc cactatcttc atgttgttgc  30540
agatgaagcg cgcaagaccg tctgaagata ccttcaaccc cgtgtatcca tgtgacacgg  30600
aaaccggtcc tccaactgtg cctttttctta ctcctccctt tgtatccccc aatgggtttc  30660
aagagagtcc ccctggggta ctctctttgc gcctatccga acctctagtt acctccaatg  30720
gcatgcttgc gctcaaaatg ggcaacggcc tctctctgga cgaggccggc aaccttacct  30780
cccaaaatgt aaccactgtg agcccactc  tcaaaaaaac caagtcaaac ataaacctgg  30840
aaatatctgc acccctcaca gttacctcag aagccctaac tgtggctgcc gccgcacctc  30900
taatggtcgc gggcaacaca ctcaccatgc aatcacaggc cccgctaacc gtgcacgact  30960
ccaaacttag cattgccacc caaggacccc tcacagtgtc agaaggaaag ctagccctgc  31020
aaacatcagg ccccctcacc accaccgata gcagtaccct tactatcact gcctcacccc  31080
ctctaactac tgccactggt agcttgggca ttgacttgaa agagcccatt tatacacaaa  31140
atggaaaact aggactaaag tacggggctc ctttgcatgt aacagacgac ctaaacactt  31200
tgaccgtagc aactggtcca ggtgtgacta ttaataatac ttccttgcaa actaaagtta  31260
ctggagcctt gggttttgat tcacaaggca atatgcaact taatgtagca ggaggactaa  31320
ggattgattc tcaaaacaga cgccttatac ttgatgttag ttatccgttt gatgctcaaa  31380
accaactaaa tctaagacta ggacagggcc ctctttttat aaactcagcc cacaacttgg  31440
atattaacta caacaaaggc ctttacttgt ttacagcttc aaacaattcc aaaaagcttg  31500
aggttaacct aagcactgcc aagggggttga tgtttgacgc tacagccata gccattaatg  31560
caggagatgg gcttgaattt ggttcaccta atgcaccaaa cacaaatccc ctcaaaacaa  31620
aaattggcca tggcctagaa tttgattcaa acaaggctat ggttcctaaa ctaggaactg  31680
gccttagttt tgacagcaca ggtgccatta cagtaggaaa caaaaataat gataagctaa  31740
ctttgtggac cacaccagct ccatctccta actgtagact aaatgcagag aaagatgcta  31800
aactcacttt ggtcttaaca aaatgtggca gtcaaatact tgctacagtt tcagttttgg  31860
ctgttaaagg cagtttggct ccaatatctg gaacagttca aagtgctcat cttattataa  31920
gatttgacga aaatggagtg ctactaaaca attccttcct ggacccagaa tattggaact  31980
```

```
ttagaaatgg agatcttact gaaggcacag cctatacaaa cgctgttgga tttatgccta   32040
acctatcagc ttatccaaaa tctcacggta aaactgccaa aagtaacatt gtcagtcaag   32100
tttacttaaa cggagacaaa actaaacctg taacactaac cattacacta aacggtacac   32160
aggaaacagg agacacaact ccaagtgcat actctatgtc attttcatgg gactggtctg   32220
gccacaacta cattaatgaa atatttgcca catcctctta cactttttca tacattgccc   32280
aagaataaag aatcgtttgt gttatgtttc aacgtgttta tttttcaatt gcagaaaatt   32340
tcaagtcatt tttcattcag tagtatagcc ccaccaccat agtgactgga tatgttgtgt   32400
tttacagtat tatgtagtct gttttttatg caaaatctaa tttaatatat tgatatttat   32460
atcattttac gtttctcgtt cagctttctt gtacaaagtg gtcatagctt atacagatca   32520 ccgtaccta atcaaactca cagaaccta gtattcaacc tgccacctcc ctcccaacac   32580
acagagtaca cagtcctttc tccccggctg gccttaaaaa gcatcatatc atgggtaaca   32640
gacatattct taggtgttat attccacacg gtttcctgtc gagccaaacg ctcatcagtg   32700
atattaataa actccccggg cagctcactt aagttcatgt cgctgtccag ctgctgagcc   32760
acaggctgct gtccaacttg cggttgctta acgggcggcg aaggagaagt ccacgcctac   32820 atggggtag agtcataatc gtgcatcagg atagggcggt ggtgctgcag cagcgcgcga   32880
ataaactgct gccgccgccg ctccgtcctg caggaataca acatggcagt ggtctcctca   32940
gcgatgattc gcaccgcccg cagcataagg cgccttgtcc tccgggcaca gcagcgcacc   33000
ctgatctcac ttaaatcagc acagtaactg cagcacagca ccacaatatt gttcaaaatc   33060
ccacagtgca aggcgctgta tccaaagctc atggcgggga ccacagaacc cacgtggcca   33120
tcataccaca agcgcaggta gattaagtgg cgacccctca taaacacgct ggacataaac   33180
attacctctt ttggcatgtt gtaattcacc acctcccggt accatataaa cctctgatta   33240
aacatggcgc catccaccac catcctaaac cagctggcca aaacctgccc gccggctata   33300
cactgcaggg aaccgggact ggaacaatga cagtggagag cccaggactc gtaaccatgg   33360
atcatcatgc tcgtcatgat atcaatgttg gcacaacaca ggcacacgtg catacacttc   33420
ctcaggatta caagctcctc ccgcgttaga accatatccc agggaacaac ccattcctga   33480
atcagcgtaa atcccacact gcagggaaga cctcgcacgt aactcacgtt gtgcattgtc   33540
aaagtgttac attcgggcag cagcggatga tcctccagta tggtagcgcg ggtttctgtc   33600
tcaaaaggag gtagacgatc cctactgtac ggagtgcgcc gagacaaccg agatcgtgtt   33660
ggtcgtagtg tcatgccaaa tggaacgccg gactagtca tatttcctga agcaaaacca   33720
ggtgcgggcg tgacaaacag atctgcgtct ccggtctcgc cgcttagatc gctctgtgta   33780
gtagttgtag tatatccact ctctcaaagc atccaggcgc ccctggctt cgggttctat   33840 gtaaactcct tcatgcgccg ctgccctgat aacatccacc accgcagaat aagccacacc   33900
cagccaacct acacattcgt tctgcgagtc acacacggga ggagcgggaa gagctggaag   33960
aaccatgttt ttttttttat tccaaaagat tatccaaaac ctcaaaatga agatctatta   34020
agtgaacgcg ctcccctccg gtggcgtggt caaactctac agccaaagaa cagataatgg   34080
catttgtaag atgttgcaca atggcttcca aaaggcaaac ggccctcacg tccaagtgga   34140
cgtaaaggct aaacccttca gggtgaatct cctctataaa cattccagca ccttcaacca   34200
tgcccaaata attctcatct cgccaccttc tcaatatatc tctaagcaaa tcccgaatat   34260
taagtccggc cattgtaaaa atctgctcca gagcgccctc caccttcagc ctcaagcagc   34320
```

```
gaatcatgat tgcaaaaatt caggttcctc acagacctgt ataagattca aaagcggaac    34380
attaacaaaa ataccgcgat cccgtaggtc ccttcgcagg gccagctgaa cataatcgtg    34440
caggtctgca cggaccagcg cggccacttc cccgccagga accttgacaa agaacccac     34500 actgattatg acacgcatac tcggagctat gctaaccagc gtagccccga tgtaagcttt    34560
gttgcatggg cggcgatata aaatgcaagg tgctgctcaa aaaatcaggc aaagcctcgc    34620
gcaaaaaaga aagcacatcg tagtcatgct catgcagata aaggcaggta agctccggaa    34680
ccaccacaga aaaagacacc attttttctct caaacatgtc tgcgggtttc tgcataaaca   34740
caaaataaaa taacaaaaaa acatttaaac attagaagcc tgtcttacaa caggaaaaac    34800
aacccttata agcataagac ggactacggc catgccggcg tgaccgtaaa aaaactggtc    34860
accgtgatta aaaagcacca ccgacagctc ctcggtcatg tccggagtca taatgtaaga    34920
ctcggtaaac acatcaggtt gattcatcgg tcagtgctaa aaagcgaccg aaatagcccg    34980
ggggaataca tacccgcagg cgtagagaca acattacagc ccccatagga ggtataacaa    35040
aattaatagg agagaaaaac acataaacac ctgaaaaacc ctcctgccta ggcaaaatag    35100
caccctcccg ctccagaaca acatacagcg cttcacagcg gcagcctaac agtcagcctt    35160
accagtaaaa aagaaaacct attaaaaaaa caccactcga cacggcacca gctcaatcag    35220
tcacagtgta aaaagggcc aagtgcagag cgagtatata taggactaaa aaatgacgta     35280
acggttaaag tccacaaaaa acacccgaaa accgcacgc gaacctacgc ccagaaacga     35340
aagccaaaaa acccacaact tcctcaaatc gtcacttccg ttttcccacg ttacgtaact    35400 tcccattta agaaaactac aattcccaac acatacaagt tactccgccc taaaacctac     35460
gtcacccgcc ccgttcccac gccccgcgcc acgtcacaaa ctccacccc tcattatcat    35520 attggcttca atccaaaata aggtatatta ttgatgat                           35558

<210> SEQ ID NO 2
<211> LENGTH: 13611
<212> TYPE: DNA
<213> ORGANISM: Artificial
<220> FEATURE:
<223> OTHER INFORMATION: adenovirus right arm shuttle plasmid

<400> SEQUENCE: 2
ctttcctgcg ttatccctg attctgtgga taaccgtatt accgctagca tggatctcgg      60
ggacgtctaa ctactaagcg agagtaggga actgccaggc atcaaataaa acgaaaggct    120
cagtcggaag actgggcctt tcgttttatc tgttgtttgt cggtgaacgc tctcctgagt    180
aggacaaatc cgccgggagc ggatttgaac gttgtgaagc aacggcccgg agggtggcgg   240
gcaggacgcc cgccataaac tgccaggcat caaactaagc agaaggccat cctgacggat    300 ggccttttg cgtttctaca aactcttcct gttagttagt tacttaagct cgggccccaa    360
ataatgattt tattttgact gatagtgacc tgttcgttgc aacaaattga taagcaatgc    420
ttttttataa tgccaactttt gtacaaaaaa gcaggcttcg aaggagatag aaccaattct    480
ctaaggaaat acttaaccat ggctctagac cgccgcgcgg ccgctttcca agatggctac    540
cccttcgatg atgccgcagt ggtcttacat gcacatctcg ggccaggacg cctcggagta    600
cctgagcccc gggctggtgc agtttgcccg cgccaccgag acgtacttca gcctgaataa    660
caagtttaga aaccccacgg tggcgcctac gcacgacgtg accacagacc ggtcccagcg    720
tttgacgctg cggttcatcc ctgtggaccg tgaggatact cgtactcgt acaaggcgcg    780 gttcacccta gctgtgggtg ataaccgtgt gctggacatg gcttccacgt actttgacat    840
```

```
ccgcggcgtg ctggacaggg gccctacttt taagccctac tctggcactg cctacaacgc    900
cctggctccc aagggtgccc caaatccttg cgaatgggaa gagaaaaaga atggaggagg    960
aagcgatgct aatcaaatgc aaactcacgt atttgggcag gcgccttatt ctggtataaa   1020
tattacaaag gagggtattc aaataggtat tgatgcaacc aaagaggaag ataatgaaa    1080
ggaaatatat gccgataaaa catttcaacc tgaacctcaa ataggagaat ctcagtggca   1140
ggatagtgat aattactatg gagggagagt ccttaaaaag actacccaa tgaaaccatg   1200
ttacggttca tatgcaaaac ccacaaatga aaatggaggg caagctaaat tcaaaacacc   1260
tgaaaaagaa ggtgaagaac ccaaagaaag tcaagtggaa atgcaatttt tcgatattcc   1320
cagtactggc acaggtggta atggaacaaa tgttaatttc aaacctaaag tggtattgta   1380
cagtgaagat gtagatatag aaaccccaga cactcatatt tcttacatgc ccggcaagga   1440
agatgcaagt tcacgagaac taatgggcca acaatctatg cccaacaggc ctaattacat   1500
tgcttttagg gacaatttta ttggtctaat gtattacaac agcacgggta atatgggtgt   1560
tctggcgggc caagcatcgc agttgaatgc tgttgtagat ttgcaagaca gaaacacaga   1620
gctttcatac cagcttttgc ttgattccat tggtgataga accaggtact tttctatgtg   1680
gaatcaggct gttgacagct atgatccaga tgttagaatt attgaaaatc atggaactga   1740
agatgaactt ccaaattact gctttccact ggatggcgct ggaactaacg cagtgtacca   1800
aggtgtaaaa gttaaaacta ctaacaatac agaatgggaa aaagacactg cagtatctga   1860
acacaatcag ataagagttg gaaataattt tgccatggaa atcaatctaa atgccaacct   1920
gtggagaaat ttcctgtact ccaacatagc gctgtatttg cccgacaagc taaagtacag   1980
tccttccaac gtaaaaattt ctgataaccc aaacacctac gactacatga acaagcgagt   2040
ggtggctccc gggttagtgg actgctacat taaccttgga gcacgctggt cccttgacta   2100
tatggacaac gtcaacccat ttaaccacca ccgcaatgct ggcctgcgct accgctcaat   2160
gttgctgggc aatggtcgct atgtgccctt ccacatccag gtgcctcaga agttctttgc   2220
cattaaaaac ctccttctcc tgccgggctc atacacctac gagtggaact tcaggaagga   2280
tgttaacatg gttctgcaga gctccctagg aaatgaccta agggttgacg gagccagcat   2340
taagtttgat agcatttgcc tttacgccac cttcttcccc atgggcccaca acaccgcctc   2400
cacgcttgag gccatgctta gaaacgacac caacgaccag tcctttaacg actatctctc   2460
cgccgccaac atgctctacc ctatacccgc caacgctacc aacgtgccca tatccatccc   2520
ctcccgcaac tgggcggctt ccgcggctg ggccttcacg cgcttaaga ctaaggaaac   2580
cccatcactg ggctcgggct acgaccctta ttacacctac tctggctcta taccctacct   2640
agatggaacc ttttacctca accacacctt taagaaggtg ccattacct ttgactcttc   2700
tgtcagctgg cctggcaatg accgcctgct taccccccaac gagtttgaaa ttaagcgctc   2760
agttgacggg gagggttaca cgttgccca gtgtaacatg accaaagact ggttcctggt   2820
acaaatgcta gctaactaca acattggcta ccagggcttc tatatcccag agagctacaa   2880
ggaccgcatg tactccttct ttagaaactt ccagcccatg agccgtcagg tggtggatga   2940
tactaaatac aaggactacc aacaggtggg catcctacac caacacaaca actctggatt   3000
tgttggctac cttgcccca ccatgcgcga aggacaggcc taccctgcta acttccccta   3060
tccgcttata ggcaagaccg cagttgacag cattacccag aaaagtttc tttgcgatcg   3120
cacccctttgg cgcatcccat tctccagtaa ctttatgtcc atgggcgcac tcacagacct   3180
```

```
gggccaaaac cttctctacg ccaactccgc ccacgcgcta gacatgactt ttgaggtgga    3240
tcccatggac gagcccaccc ttctttatgt tttgtttgaa gtctttgacg tggtccgtgt    3300
gcaccggccg caccgcggcg tcatcgaaac cgtgtacctg cgcacgccct tctcggccgg    3360
caacgccaca acataaagaa gcaagcaaca tcaacaacag ctgccgccat gggctccagt    3420
gagcaggaac tgaaagccat tgtcaaagac cttggttgtg ggccatattt tttgggcacc    3480
tatgacaagc gctttccagg cttttgtttct ccacacaagc tcgcctgcgc catagtcaat    3540
```

```
gggggcgccc ggggaggcgg cggcgacggg gacgggacg  acacgtcctc catggttggg   5640
ggacgtcgcg ccgcaccgcg tccgcgctcg ggggtggttt cgcgctgctc ctcttcccga   5700
ctggccattt ccttctccta taggcagaaa aagatcatgg agtcagtcga gaagaaggac   5760
agcctaaccg ccccctctga gttcgccacc accgcctcca ccgatgccgc caacgcgcct   5820
accaccttcc ccgtcgaggc accccgctt gaggaggagg aagtgattat cgagcaggac   5880
ccaggttttg taagcgaaga cgacgaggac cgctcagtac caacagagga taaaagcaa   5940 gaccaggaca acgcagaggc aaacgaggaa caagtcgggc gggggacga aaggcatggc    6000 gactacctag atgtgggaga cgacgtgctg ttgaagcatc tgcagcgcca gtgcgccatt   6060
atctgcgacg cgttgcaaga gcgcagcgat gtgcccctcg ccatagcgga tgtcagcctt   6120
gcctacgaac gccacctatt ctcaccgcgc gtaccccca aacgccaaga aaacggcaca    6180
tgcgagccca cccgcgcct caacttctac cccgtatttg ccgtgccaga ggtgcttgcc    6240
acctatcaca tcttttttcca aaactgcaag ataccctat cctgccgtgc caaccgcagc    6300
cgagcggaca agcagctggc cttgcggcag ggcgctgtca tacctgatat cgcctcgctc   6360
aacgaagtgc caaaaatctt tgagggtctt ggacgcgacg agaagcgcgc ggcaaacgct   6420
ctgcaacagg aaaacagcga aaatgaaagt cactctggag tgttggtgga actcgagggt   6480
gacaacgcgc gcctagccgt actaaaacgc agcatcgagg tcacccactt tgcctacccg   6540
gcacttaacc tacccccaa ggtcatgagc acagtcatga gtgagctgat cgtgcgccgt    6600
gcgcagcccc tggagaggga tgcaaatttg caagaacaaa cagaggaggg cctacccgca   6660
gttggcgacg agcagctagc gcgctggctt caaacgcgcg agcctgccga cttggaggag   6720
cgacgcaaac taatgatggc cgcagtgctc gttaccgtgg agcttgagtg catgcagcgg   6780
ttctttgctg acccggagat gcagcgcaag ctagaggaaa cattgcacta cacctttcga   6840
cagggctacg tacgccaggc ctgcaagatc tccaacgtgg agctctgcaa cctggtctcc   6900
taccttggaa ttttgcacga aaaccgcctt gggcaaaacg tgcttcattc cacgctcaag   6960
ggcgaggcgc ccgcgacta cgtccgcgac tgcgtttact tatttctatg ctacacctgg   7020
cagacggcca tgggcgtttg gcagcagtgc ttggaggagt gcaacctcaa ggagctgcag   7080
aaactgctaa agcaaaactt gaaggaccta tggacggcct tcaacgagcg ctccgtggcc   7140
gcgcacctgg cggacatcat tttccccgaa cgcctgctta aaaccctgca acagggtctg   7200
ccagacttca ccagtcaaag catgttgcag aactttagga actttatcct agagcgctca   7260
ggaatcttgc ccgccacctg ctgtgcactt cctagcgact ttgtgcccat taagtaccgc   7320
gaatgccctc cgccgctttg gggccactgc taccttctgc agctagccaa ctaccttgcc   7380
taccactctg acataatgga agacgtgagc ggtgacggtc tactgagtg tcactgtcgc    7440 tgcaacctat gcaccccgca ccgctccctg gtttgcaatt cgcagctgct taacgaaagt   7500
caaattatcg gtacctttga gctgcagggt ccctcgcctg acgaaaagtc cgcggctccg   7560
gggttgaaac tcactccggg gctgtggacg tcggcttacc ttcgcaaaatt tgtacctgag   7620 gactaccacg cccacgagat taggttctac gaagaccaat cccgcccgcc aaatgcggag   7680
cttaccgcct gcgtcattac ccagggccac attcttggcc aattgcaagc catcaacaaa   7740
gcccgccaag agtttctgct acgaaaggga cggggggttt acttggaccc ccagtccggc   7800
gaggagctca acccaatccc cccgccgccg cagccctatc agcagcagcc gcgggccctt   7860
gcttcccagg atggcaccca aaaagaagct gcagctgccg ccgccaccca cggacgagga   7920
```

-continued

| | | | |
|---|---|---|---|
| ggaatactgg gacagtcagg cagaggaggt tttggacgag gaggaggagg acatgatgga | | | 7980 |
| agactgggag agcctagacg aggaagcttc cgaggtcgaa gaggtgtcag acgaaacacc | | | 8040 |
| gtcaccctcg gtcgcattcc cctcgccggc gccccagaaa tcggcaaccg gttccagcat | | | 8100 |
| ggctacaacc tccgctcctc aggcgccgcc ggcactgccc gttcgccgac ccaaccgtag | | | 8160 |
| atgggacacc actggaacca gggccggtaa gtccaagcag ccgccgccgt tagcccaaga | | | 8220 |
| gcaacaacag cgccaaggct accgctcatg gcgcgggcac aagaacgcca tagttgcttg | | | 8280 |
| cttgcaagac tgtgggggca acatctcctt cgcccgccgc tttcttctct accatcacgg | | | 8340 |
| cgtggccttc ccccgtaaca tcctgcatta ctaccgtcat ctctacagcc catactgcac | | | 8400 |
| cggcggcagc ggcagcggca gcaacagcag cggccacaca gaagcaaagg cgaccggata | | | 8460 |
| gcaagactct gacaaagccc aagaaatcca cagcggcggc agcagcagga ggaggagcgc | | | 8520 |
| tgcgtctggc gcccaacgaa cccgtatcga cccgcgagct tagaaacagg attttttccca | | | 8580 |
| ctctgtatgc tatatttcaa cagagcaggg gccaagaaca agagctgaaa ataaaaaaca | | | 8640 |
| ggtctctgcg atccctcacc cgcagctgcc tgtatcacaa aagcgaagat cagcttcggc | | | 8700 |
| gcacgctgga agacgcggag gctctcttca gtaaatactg cgcgctgact cttaaggact | | | 8760 |
| agtttcgcgc cctttctcaa atttaagcgc gaaaactacg tcatctccag cggccacacc | | | 8820 |
| cggcgccagc acctgtcgtc agcgccatta tgagcaagga aattcccacg ccctacatgt | | | 8880 |
| ggagttacca gccacaaatg ggacttgcgg ctggagctgc ccaagactac tcaacccgaa | | | 8940 |
| taaactacat gagcgcggga ccccacatga tatcccgggt caacggaatc cgcgcccacc | | | 9000 |
| gaaaccgaat tctcttggaa caggcggcta ttaccaccac acctcgtaat aaccttaatc | | | 9060 |
| cccgtagttg gcccgctgcc ctggtgtacc aggaaagtcc cgctcccacc actgtggtac | | | 9120 |
| ttcccagaga cgcccaggcc gaagttcaga tgactaactc aggggcgcag cttgcgggcg | | | 9180 |
| gctttcgtca cagggtgcgg tcgcccgggc agggtataac tcacctgaca atcagagggc | | | 9240 |
| gaggtattca gctcaacgac gagtcggtga gctcctcgct tggtctccgt ccggacggga | | | 9300 |
| catttcagat cggcggcgcc ggccgtcctt cattcacgcc tcgtcaggca atcctaactc | | | 9360 |
| tgcagacctc gtcctctgag ccgcgctctg gaggcattgg aactctgcaa tttattgagg | | | 9420 |
| agtttgtgcc atcggtctac tttaaccccct tctcgggacc tcccggccac tatccggatc | | | 9480 |
| aatttattcc taactttgac gcggtaaagg actcggcgga cggctacgac tgaatgttaa | | | 9540 |
| gtggagaggc agagcaactg cgcctgaaac acctggtcca ctgtcgccgc cacaagtgct | | | 9600 |
| ttgcccgcga ctccggtgag ttttgctact ttgaattgcc cgaggatcat atcgagggcc | | | 9660 |
| cggcgcacgg cgtccggctt accgcccagg gagagcttgc ccgtagcctg attcgggagt | | | 9720 |
| ttacccagcg cccctgcta gttgagcggg acagggacc ctgtgttctc actgtgattt | | | 9780 |
| gcaactgtcc taaccttgga ttacatcaag atcctctagt taattaagat atctgagtca | | | 9840 |
| ttagggactt tccaatgggt tttgcccagt acataaggtc aatagggtg aatcaacagg | | | 9900 |
| aaagtcccat tggagccaag tacactgagt caataggac tttccattgg gttttgccca | | | 9960 |
| gtacaaaagg tcatagggg gtgagtcaat gggttttcc cattattggc acgtacataa | | | 10020 |
| ggtcaatagg ggtgagtcat ggggtttttc cagccattta attaaaacgc catgtacttt | | | 10080 |
| cccaccattg acgtcaatgg gctattgaaa ctaatgcaac gtgaccttta acggtacttt | | | 10140 |
| tcccatagct gattaatggg aaagtaccgt tctcgagcca atacacgtca atgggaagtg | | | 10200 |
| aaagggcagc caaaacgtaa caccgccccg gttttccccct ggaaattcca tattggcact | | | 10260 |
| cattctattg gctgagctgc gttctacgtg ggtataagag gcgcgaccag cgtcggtacc | | | 10320 |

```
gtcgcagtct tcggtctgac caccgtagaa cgcagatcga attactagtc agggaattcg   10380
gtaccgctag ccatggacgc gttaaccggt gatatcgata gatctcatat ggatccagct   10440
tgtcgacttc gagcaacttg tttattgcag cttataatgg ttacaaataa agcaatagca   10500
tcacaaattt cacaaataaa gcattttttt cactgcattc tagttgtggt ttgtccaaac   10560
tcatcaatgt atcttatcat gtctggatcg tctagcatcg aagatcctag caaatttctg   10620 tccagttttat tcagcagcac ctccttgccc tcctcccagc tctggtattg cagcttcctc   10680
ctggctgcaa actttctcca caatctaaat ggaatgtcag tttcctcctg ttcctgtcca   10740
tccgcaccca ctatcttcat gttgtgcacc atgaagcgcg caagaccgtc tgaagatacc   10800
ttcaaccccg tgtatccata tgacacggaa accggtcctc caactgtgcc ttttcttact   10860 cctcccttg tatcccccaa tgggtttcaa gagagtcccc ctggagttct actttaaaa    10920 tgtttaaccc cactaacaac cacaggcgga tctctacagc taaaagtggg aggggactt    10980 acagtggatg acaccaacgg ttttttgaaa gaaaacataa gtgccaccac accactcgtt   11040
aagactggtc actctatagg tttaccacta ggagccggat tgggaacgaa tgaaaataaa   11100
ctttgtatca aattaggaca aggacttaca ttcaattcaa acaacatttg cattgatgac   11160
aatattaaca ccttatggac aggagtcaac cccaccgaag ccaactgtca atcatgaac    11220 tccagtgaat ctaatgattg caaattaatt ctaacactag ttaaaactgg agcactagtc   11280
actgcatttg tttatgttat aggagtatct aacaatttta atatgctaac tacacacaga   11340
aatataaatt ttactgcaga gctgttttc gattctaact ggtaatttaa ctaactagac   11400
tctcatcccc tcaaaactcc acttaatcat aaatcaggac aaaacatggc tactggtgcc   11460
attactaatg ctaaaggttt catgcccagc acgactgcct atcctttcaa tgataattct   11520
agagaaaaag aaaactacat ttacggaact tgttactaca cagctagtga tcgcactgct   11580
tttcccattg acatatctgt catgcttaac cgaagagcaa taaatgacga gacatcatat   11640
tgtattcgta taacttggtc ctggaacaca ggagatgccc cagaggtgca aacctctgct   11700
acaaccctag tcacctcccc atttacctt tactacatca gagaagacga ctaaagaatc   11760
gtttgtgtta tgtttcaacg tgtttatttt tcaattgcag aaaatttcaa gtcatttttc   11820
attcagtagt atactctaga cccagctttc ttgtacaaag ttggcattat aagaaagcat   11880
tgcttatcaa tttgttgcaa cgaacaggtc actatcagtc aaaataaaat cattatttgc   11940
catccagctg cagctctggc ccgtgtctca aaatctctga tgttacattg cacaagataa   12000
aaatatatca tcatgaacaa taaaactgtc tgcttacata acagtaata caaggggtgt    12060 tatgagccat attcaacggg aaacgtcgag gccgcgatta aattccaaca tggatgctga   12120
tttatatggg tataaatggg ctcgcgataa tgtcgggcaa tcaggtgcga caatctatcg   12180
cttgtatggg aagcccgatg cgccagagtt gtttctgaaa catggcaaag gtagcgttgc   12240
caatgatgtt acagatgaga tggtcagact aaactggctg acggaattta tgcctcttcc   12300
gaccatcaag cattttatcc gtactcctga tgatgcatgg ttactcacca ctgcgatccc   12360
cggaaaaaca gcattccagg tattagaaga atatcctgat tcaggtgaaa atattgttga   12420
tgcgctggca gtgttcctgc gccggttgca ttcgattcct gtttgtaatt gtccttttaa   12480
cagcgatcgc gtatttcgtc tcgctcaggc gcaatcacga atgaataacg gtttggttga   12540
tgcgagtgat tttgatgacg agcgtaatgg ctggcctgtt gaacaagtct ggaaagaaat   12600
gcataaactt ttgccattct caccggattc agtcgtcact catggtgatt tctcacttga   12660
```

| | | |
|---|---|---|
| taaccttatt tttgacgagg ggaaattaat aggttgtatt gatgttggac gagtcggaat | 12720 |
| cgcagaccga taccaggatc ttgccatcct atggaactgc ctcggtgagt tttctccttc | 12780 |
| attacagaaa cggcttttc aaaaatatgg tattgataat cctgatatga ataaattgca | 12840 |
| gtttcatttg atgctcgatg agttttcta atcagaattg gttaattggt tgtaacatta | 12900 |
| ttcagattgg gccccgttcc actgagcgtc agaccccgta gaaaagatca aggatcttc | 12960 |
| ttgagatcct ttttttctgc gcgtaatctg ctgcttgcaa acaaaaaaac caccgctacc | 13020 |
| agcggtggtt tgtttgccgg atcaagagct accaactctt tttccgaagg taactggctt | 13080 |
| cagcagagcg cagataccaa atactgttct tctagtgtag ccgtagttag gccaccactt | 13140 |
| caagaactct gtagcaccgc ctacatacct cgctctgcta atcctgttac cagtggctgc | 13200 |
| tgccagtggc gataagtcgt gtcttaccgg gttggactca agacgatagt taccggataa | 13260 |
| ggcgcagcgg tcgggctgaa cggggggttc gtgcacacag cccagcttgg agcgaacgac | 13320 |
| ctacaccgaa ctgagatacc tacagcgtga gctatgagaa agcgccacgc ttcccgaagg | 13380 |
| gagaaaggcg gacaggtatc cggtaagcgg cagggtcgga acaggagagc gcacgaggga | 13440 |
| gcttccaggg ggaaacgcct ggtatcttta tagtcctgtc gggtttcgcc acctctgact | 13500 |
| tgagcgtcga ttttgtgat gctcgtcagg ggggcggagc ctatggaaaa acgccagcaa | 13560 |
| cgcggccttt ttacggttcc tggccttttg ctggcctttt gctcacatgt t | 13611 |

<210> SEQ ID NO 3
<211> LENGTH: 5311
<212> TYPE: DNA
<213> ORGANISM: Artificial
<220> FEATURE:
<223> OTHER INFORMATION: adenovirus left arm shuttle plasmid
<220> FEATURE:
<221> NAME/KEY: misc_feature
<222> LOCATION: (454)..(454)
<223> OTHER INFORMATION: n is a, c, g, or t

<400> SEQUENCE: 3

| | | |
|---|---|---|
| ttcatcaata atatacctta ttttggattg aagccaatat gataatgagg gggtggagtt | 60 |
| tgtgacgtgg cgcggggcgt gggaacgggg cgggtgacgt agtagtgtgg cggaagtgtg | 120 |
| atgttgcaag tgtggcggaa cacatgtaag cgacggatgt ggcaaaagtg acgttttgg | 180 |
| tgtgcgccgg tgtacacagg aagtgacaat tttcgcgcgg ttttaggcgg atgttgtagt | 240 |
| aaatttgggc gtaaccgagt aagatttggc cattttcgcg ggaaaactga ataagaggaa | 300 |
| gtgaaatctg aataattttg tgttactcat agcgcgtaat atttgtctag gccgcgggg | 360 |
| actttgaccg tttacgtgga gactcgccca ggtgttttc tcaggtgttt tccgcgttcc | 420 |
| gggtcaaagt tggcgtttta ttattatagt cagntctaga gatatactta ataggctgca | 480 |
| ggacttactg ttggtgggac gccctgcttt gcgaagggaa aggaggagtt tgccctgagc | 540 |
| acaggccccc accctccact gggctttccc cagctccctt gtcttcttat cacggtagtg | 600 |
| gcccagtccc tggcccctga ctccagaagg tggccctcct ggaaacccag gtcgtgcagt | 660 |
| caacgatgta ctcgccggga cagcgatgtc tgctgcactc catccctccc ctgttcattt | 720 |
| gtccttcatg cccgtctgga gtagatgctt tttgcagagg tggcaccctg taaagctctc | 780 |
| ctgtctgact ttttttttt tttagactg agttttgctc ttgttgccta ggctggagtg | 840 |
| caatggcaca atctcagctc actgcaccct ctgcctccg ggttcaagcg attctcctgc | 900 |
| ctcagcctcc cgagtagttg ggattacagg catgcaccac cacgcccagc taattttgt | 960 |
| attttagta gagacaaggt ttcaccgtga tggccaggct ggtcttgaac tccaggactc | 1020 |

```
aagtgatgct cctgcctagg cctctcaaag tgttgggatt acaggcgtga gccactgcac    1080
ccggcctgca cgcgttcttt gaaagcagtc gagggggcgc taggtgtggg cagggacgag    1140
ctggcgcggc gtcgctgggt gcaccgcgac cacgggcaga gccacgcggc gggaggacta    1200
caactcccgg cacaccccgc gccgccccgc ctctactccc agaaggccgc gggggtggcg    1260
ccgcctaaga gggcgtgcgc tcccgacatg ccccgcggcg cgccattaac cgccagattt    1320
gaatcgcggc gaggatccac tagtgattta aatctcgaga attcggtacc gctagccatg    1380
gacgcgttaa ccggtgatat cgatagatct caccatgaga catattatct gccacggagg    1440
tgttattacc gaagaaatgg ccgccagtct tttggaccag ctgatcgaag aggtactggc    1500
tgataatctt ccacctccta gccattttga accacctacc cttcacgaac tgtatgattt    1560
agacgtgacg gcccccgaag atcccaacga ggaggcggtt tcgcagattt ttcccgactc    1620
tgtaatgttg gcggtgcagg aagggattga cttactcact tttccgccgg cgcccggttc    1680
tccggagccg cctcaccttt ccggcagcc cgagcagccg gagcagagag ccttgggtcc    1740
ggtttctatg ccaaaccttg taccggaggt gatcgatctt acctgccacg aggctggctt    1800
tccacccagt gacgacgagg atgaagaggg tgaggagttt gtgttagatt atgtggagca    1860
ccccgggcac ggttgcaggt cttgtcatta tcaccggagg aatacgggg acccagatat     1920 tatgtgttcg ctttgctata tgaggacctg tggcatgttt gtctacagta agtgaaaatt    1980
atgggcagtg ggtgatagag tggtgggttt ggtgtggtaa ttttttttt aattttaca     2040 gttttgtggt ttaaagaatt ttgtattgtg attttttaa aaggtcctgt gtctgaacct     2100
gagcctgagc ccgagccaga accggagcct gcaagaccta cccgccgtcc taaaatggcg    2160
cctgctatcc tgagacgccc gacatcacct gtgtctagag aatgcaatag tagtacggat    2220
agctgtgact ccggtccttc taacacacct cctgagatac acccggtggt cccgctgtgc    2280
cccattaaac cagttgccgt gagagttggt gggcgtcgcc aggctgtgga atgtatcgag    2340
gacttgctta acgagcctgg gcaacctttg gacttgagct gtaaacgccc caggccataa    2400
gtcgacgcgg ccgcaagctt ctagagttcg agcaacttgt ttattgcagc ttataatggt    2460
tacaaataaa gcaatagcat cacaaatttc acaaataaag catttttttc actgcattct    2520
agttgtggtt tgtccaaact catcaatgta tcttatcatg tctggatcgt ctagcatcga    2580
agatccaata acttcgtata gcatacatta tacgaagtta taagtagctt ggcgtaatca    2640
tggtcatagc tgtttcctgt gtgaaattgt tatccgctca caattccaca acatacga     2700 gccgaagca taaagtgtaa agcctggggt gcctaatgag tgagctaact cacattaatt    2760
gcgttgcgct cactgcccgc tttccagtcg ggaaacctgt cgtgccagct gcattaatga    2820
atcggccaac gcgcggggag aggcggtttg cgtattgggc gctcttccgc ttcctcgctc    2880
actgactcgc tgcgctcggt cgttcggctg cggcgagcgg tatcagctca ctcaaaggcg    2940
gtaatacggt tatccacaga atcagggat aacgcaggaa agaacatgtg agcaaaaggc    3000
cagcaaaagg ccaggaaccg taaaaaggcc gcgttgctgg cgttttccca taggctccgc    3060 cccctgacg agcatcacaa aaatcgacgc tcaagtcaga ggtggcgaaa cccgacagga    3120
ctataaagat accaggcgtt tcccctgga agctccctcg tgcgctctcc tgttccgacc    3180
ctgccgctta ccggatacct gtccgccttt ctcccttcgg gaagcgtggc gctttctcaa    3240
tgctcacgct gtaggtatct cagttcggtg taggtcgttc gctccaagct gggctgtgtg    3300
cacgaacccc ccgttcagcc cgaccgctgc gccttatccg gtaactatcg tcttgagtcc    3360
```

```
aacccggtaa gacacgactt atcgccactg gcagcagcca ctggtaacag gattagcaga    3420
gcgaggtatg taggcggtgc tacagagttc ttgaagtggt ggcctaacta cggctacact    3480
agaaggacag tatttggtat ctgcgctctg ctgaagccag ttaccttcgg aaaaagagtt    3540
ggtagctctt gatccggcaa acaaaccacc gctggtagcg gtggttttt tgtttgcaag     3600
cagcagatta cgcgcagaaa aaaggatct caagaagatc ctttgatctt ttctacgggg     3660
tctgacgctc agtggaacga aaactcacgt taagggattt tggtcatgag attatcaaaa    3720
aggatcttca cctagatcct tttaaattaa aaatgaagtt ttaaatcaat ctaaagtata    3780
tatgagtaaa cttggtctga cagttaccaa tgcttaatca gtgaggcacc tatctcagcg    3840
atctgtctat ttcgttcatc catagttgcc tgactccccg tcgtgtagat aactacgata    3900
cgggagggct taccatctgg ccccagtgct gcaatgatac cgcgagaccc acgctcaccg    3960
gctccagatt tatcagcaat aaaccagcca gccggaaggg ccgagcgcag aagtggtcct    4020
gcaactttat ccgcctccat ccagtctatt aattgttgcc gggaagctag agtaagtagt    4080
tcgccagtta atagtttgcg caacgttgtt gccattgcta caggcatcgt ggtgtcacgc    4140
tcgtcgtttg gtatggcttc attcagctcc ggttcccaac gatcaaggcg agttacatga    4200
tcccccatgt tgtgcaaaaa agcggttagc tccttcggtc ctccgatcgt tgtcagaagt    4260
aagttggccg cagtgttatc actcatggtt atggcagcac tgcataattc tcttactgtc    4320
atgccatccg taagatgctt ttctgtgact ggtgagtact caaccaagtc attctgagaa    4380
tagtgtatgc ggcgaccgag ttgctcttgc ccggcgtcaa cacgggataa taccgcgcca    4440
catagcagaa ctttaaaagt gctcatcatt ggaaaacgtt cttcggggcg aaaactctca    4500
aggatcttac cgctgttgag atccagttcg atgtaaccca ctcgtgcacc caactgatct    4560
tcagcatctt ttactttcac cagcgtttct gggtgagcaa aaacaggaag caaaatgcc     4620
gcaaaaagg gaataagggc gacacggaaa tgttgaatac tcatactctt ccttttcaa      4680
tattattgaa gcatttatca gggttattgt ctcatgagcg gatacatatt tgaatgtatt    4740
tagaaaaata acaaataggg gttccgcgc acatttcccc gaaaagtgcc acctgacgtc     4800
taagaaacca ttattatcat gacattaacc tataaaaata ggcgtatcac tctaggcaaa    4860
atagcaccct cccgctccag aacaacatac agcgcttcac agcggcagcc taacagtcag    4920
ccttaccagt aaaaagaaa acctattaaa aaaacaccac tcgacacggc accagctcaa     4980
tcagtcacag tgtaaaaaag ggccaagtgc agagcgagta tatataggac taaaaaatga    5040
cgtaacggtt aaagtccaca aaaaacaccc agaaaaccgc acgcgaacct acgcccagaa    5100
acgaaagcca aaaaacccac aacttcctca atcgtcact tccgttttcc cacgttacgt     5160
aacttcccat tttaagaaaa ctacaattcc caacacatac aagttactcc gcccttaaaac   5220
ctacgtcacc cgccccgttc ccacgccccg cgccacgtca caaactccac cccctcatta    5280
tcatattggc ttcaatccaa aataaggtat a                                  5311

<210> SEQ ID NO 4
<211> LENGTH: 32417
<212> TYPE: DNA
<213> ORGANISM: Artificial
<220> FEATURE:
<223> OTHER INFORMATION: oncolytic adenovirus
<220> FEATURE:
<221> NAME/KEY: misc_feature
<222> LOCATION: (454)..(454)
<223> OTHER INFORMATION: n is a, c, g, or t

<400> SEQUENCE: 4
```

```
ttcatcaata atatacctta tttttggattg aagccaatat gataatgagg gggtggagtt      60
tgtgacgtgg cgcggggcgt gggaacgggg cgggtgacgt agtagtgtgg cggaagtgtg     120
atgttgcaag tgtggcggaa cacatgtaag cgacggatgt ggcaaaagtg acgttttttgg    180 tgtgcgccgt tgtacacagg aagtgacaat tttcgcgcgg ttttaggcgg atgttgtagt     240
aaatttgggc gtaaccgagt aagatttggc cattttcgcg ggaaaactga ataagaggaa     300
gtgaaatctg aataattttg tgttactcat agcgcgtaat atttgtctag gccgcgggg     360 actttgaccg tttacgtgga gactcgccca ggtgttttc tcaggtgttt tccgcgttcc     420
gggtcaaagt tggcgtttta ttattatagt cagntctaga gatatactta ataggctgca    480
ggacttactg ttggtgggac gccctgcttt gcgaagggaa aggaggagtt tgccctgagc    540 acaggcccccc accctccact gggctttccc cagctccctt gtcttcttat cacggtagtg   600
gcccagtccc tggcccctga ctccagaagg tggccctcct ggaaacccag gtcgtgcagt    660
caacgatgta ctcgccggga cagcgatgtc tgctgcactc catccctccc ctgttcattt    720
gtccttcatg cccgtctgga gtagatgctt tttgcagagg tggcacccctg taaagctctc   780 ctgtctgact tttttttttt ttttagactg agttttgctc ttgttgccta ggctggagtg    840
caatggcaca atctcagctc actgcaccct ctgcctcccg ggttcaagcg attctcctgc    900
ctcagcctcc cgagtagttg ggattacagg catgcaccac cacgcccagc taattttgt     960 attttagta gagacaaggt ttcaccgtga tggccaggct ggtcttgaac tccaggactc    1020
aagtgatgct cctgcctagg cctctcaaag tgttgggatt acaggcgtga gccactgcac   1080
ccggcctgca cgcgttcttt gaaagcagtc gagggggcgc taggtgtggg cagggacgag   1140
ctggcgcggc gtcgctgggt gcaccgcgac cacgggcaga gccacgcggc gggaggacta   1200
caactcccgg cacaccccgc gccgccccgc ctctactccc agaaggccgc gggggtgga    1260 ccgcctaaga gggcgtgcgc tcccgacatg ccccgcggcg cgccattaac cgccagattt   1320
gaatcgcggc gaggatccac tagtgattta aatctcgaga attcggtacc gctagccatg   1380
gacgcgttaa ccgtgatat cgatagatct caccatgaga catattatct gccacggagg    1440
tgttattacc gaagaaatgg ccgccagtct tttggaccag ctgatcgaag aggtactggc   1500
tgataatctt ccacctccta gccatttga accacctacc cttcacgaac tgtatgattt     1560
agacgtgacg gcccccgaag atcccaacga ggaggcggtt tcgcagattt ttcccgactc   1620
tgtaatgttg gcggtgcagg aagggattga cttactcact tttccgccgg cgcccggttc   1680
tccggagccg cctcaccttt cccggcagcc cgagcagccg gagcagagag ccttgggtcc   1740
ggtttctatg ccaaaccttg taccggaggt gatcgatctt acctgccacg aggctggctt   1800
tccacccagt gacgacgagg atgaagaggg tgaggagttt gtgttagatt atgtggagca   1860
ccccgggcac ggttgcaggt cttgtcatta tcaccggagg aatacggggg acccagatat   1920
tatgtgttcg ctttgctata tgaggacctg tggcatgttt gtctacagta agtgaaaatt   1980
atgggcagtg ggtgatagag tggtgggttt ggtgtggtaa ttttttttt aatttttaca   2040 gttttgtggt ttaaagaatt ttgtattgtg attttttta aaggtcctgt gtctgaacct    2100
gagcctgagc ccgagccaga accggagcct gcaagaccta cccgccgtcc taaaatggcg   2160
cctgctatcc tgagacgccc gacatcacct gtgtctagag aatgcaatag tagtacggat   2220
agctgtgact ccggtccttc taacacacct cctgagatac acccggtggt cccgctgtgc   2280
cccattaaac cagttgccgt gagagttggt gggcgtcgcc aggctgtgga atgtatcgag   2340
```

```
gacttgctta acgagcctgg gcaacctttg gacttgagct gtaaacgccc caggccataa    2400
gtcgacgcgg ccgcaagctt ctagagttcg agcaacttgt ttattgcagc ttataatggt    2460
tacaaataaa gcaatagcat cacaaatttc acaaataaag cattttttc actgcattct     2520 agttgtggtt tgtccaaact catcaatgta tcttatcatg tctggatcgt ctagcatcga    2580
agatccaata acttcgtata gcatacatta tacgaagtta taagtactga attcggatct    2640
gggcgtggtt aagggtggga aagaatatat aaggtggggg tcttatgtag ttttgtatct    2700
gttttgcagc agccgccgcc gccatgagca ccaactcgtt tgatggaagc attgtgagct    2760
catatttgac aacgcgcatg cccccatggg ccggggtgcg tcagaatgtg atgggctcca    2820
gcattgatgg tcgccccgtc ctgcccgcaa actctactac cttgacctac gagaccgtgt    2880
ctggaacgcc gttggagact gcagcctccg ccgccgcttc agccgctgca gccaccgccc    2940
gcgggattgt gactgacttt gctttcctga gcccgcttgc aagcagtgca gcttcccgtt    3000
catccgcccg cgatgacaag ttgacggctc ttttggcaca attggattct ttgcccgggg    3060
aacttaatgt cgtttctcag cagctgttgg atctgcgcca gcaggtttct gccctgaagg    3120
cttcctcccc tcccaatgcg gtttaaaaca taaataaaaa accagactct gtttggattt    3180
ggatcaagca agtgtcttgc tgtctttatt taggggtttt gcgcgcgcgg taggcccggg    3240
accagcggtc tcggtcgttg agggtcctgt gtattttttc caggacgtgg taaaggtgac    3300
tctggatgtt cagatacatg ggcataagcc cgtctctggg gtgaggtag caccactgca    3360 gagcttcatg ctgcggggtg tgttgtaga tgatccagtc gtagcaggag cgctgggcgt    3420
ggtgcctaaa aatgtctttc agtagcaagc tgattgccag gggcaggccc ttggtgtaag    3480
tgtttacaaa gcggttaagc tgggatgggt gcatacgtgg ggatatgaga tgcatcttgg    3540
actgtatttt taggttggct atgttcccag ccatatccct ccggggattc atgttgtgca    3600
gaaccaccag cacagtgtat ccggtgcact tgggaaattt gtcatgtagc ttagaaggaa    3660
atgcgtggaa gaacttggag acgcccttgt gacctccaag atttttccatg cattcgtcca    3720 taatgatggc aatgggccca cgggcggcgg cctgggcgaa gatatttctg ggatcactaa    3780
cgtcatagtt gtgttccagg atgagatcgt cataggccat ttttacaaag cgcgggcgga    3840
gggtgccaga ctgcggtata atggttccat ccggcccagg ggcgtagtta ccctcacaga    3900
tttgcatttc ccacgctttg agttcagatg ggggatcat gtctacctgc ggggcgatga    3960
agaaaacggt ttccggggta ggggagatca gctgggaaga aagcaggttc ctgagcagct    4020
gcgacttacc gcagccggtg ggcccgtaaa tcacacctat taccgggtgc aactggtagt    4080
taagagagct gcagctgccg tcatccctga gcagggggc cacttcgtta agcatgtccc    4140
tgactcgcat gttttccctg accaaatccg ccagaaggcg ctcgccgccc agcgatagca    4200
gttcttgcaa ggaagcaaag ttttttcaacg gtttgagacc gtccgccgta ggcatgcttt    4260
tgagcgtttg accaagcagt tccaggcggt cccacagctc ggtcacctgc tctacggcat    4320
ctcgatccag catatctcct cgtttcgcgg gttgggcgc ctttcgctgt acggcagtag     4380
tcggtgctcg tccagacggg ccagggtcat gtctttccac gggcgcaggg tcctcgtcag    4440
cgtagtctgg gtcacggtga aggggtcgcg tccgggctgc gcgctggcca gggtgcgctt    4500
gaggctggtc ctgctggtgc tgaagcgctg ccggtcttcg ccctgcgcgt cggccaggta    4560
gcatttgacc atggtgtcat agtccagccc ctccgcggcg tggcccttgg cgcgcagctt    4620
gcccttggag gaggcgccgc acgaggggca gtgcagactt tgagggcgt agagcttggg    4680 cgcgagaaat accgattccg gggagtaggc atccgcgccg caggccccgc agacggtctc    4740
```

-continued

```
gcattccacg agccaggtga gctctggccg ttcggggtca aaaaccaggt ttcccccatg   4800
cttttttgatg cgtttcttac ctctggtttc catgagccgg tgtccacgct cggtgacgaa   4860
aaggctgtcc gtgtccccgt atacagactt gagaggcctg tcctcgagcg tgttccgcg    4920
gtcctcctcg tatagaaact cggaccactc tgagacaaag gctcgcgtcc aggccagcac   4980
gaaggaggct aagtgggagg ggtagcggtc gttgtccact aggggtcca ctcgctccag    5040
ggtgtgaaga cacatgtcgc cctcttcggc atcaaggaag gtgattggtt tgtaggtgta   5100
ggccacgtga ccgggtgttc ctgaagggg gctataaaag ggggtgggg cgcgttcgtc    5160
ctcactctct tccgcatcgc tgtctgcgag gccagctgt tggggtgagt actccctctg    5220
aaaagcgggc atgacttctg cgctaagatt gtcagtttcc aaaaacgagg aggatttgat   5280
attcacctgg cccgcggtga tgcctttgag ggtggccgca tccatctggt cagaaaagac   5340
aatctttttg ttgtcaagct tggtggcaaa cgacccgtag agggcgttgg acagcaactt   5400
ggcgatggag cgcagggttt ggttttttgtc gcgatcggcg cgctccttgg ccgcgatgtt   5460
tagctgcacg tattcgcgcg caacgcaccg ccattcggga aagacggtgg tgcgctcgtc   5520
gggcaccagg tgcacgcgcc aaccgcggtt gtgcagggtg acaaggtcaa cgctggtggc   5580
tacctctccg cgtaggcgct cgttggtcca gcagaggcgg ccgcccttgc gcgagcagaa   5640
tggcggtagg gggtctagct gcgtctcgtc cggggggtct gcgtccacgg taaagacccc   5700
gggcagcagg cgcgcgtcga agtagtctat cttgcatcct tgcaagtcta gcgcctgctg   5760
ccatgcgcgg gcggcaagcg cgcgctcgta tgggttgagt gggggacccc atggcatggg   5820
gtgggtgagc gcggaggcgt acatgccgca aatgtcgtaa acgtagaggg gctctctgag   5880
tattccaaga tatgtagggt agcatcttcc accgcggatg ctggcgcgca cgtaatcgta   5940
tagttcgtgc gagggagcga ggaggtcggg accgaggttc tacgggcgg gctgctctgc    6000
tcggaagact atctgcctga agatggcatg tgagttggat gatatggttg gacgctggaa   6060
gacgttgaag ctggcgtctg tgagacctac cgcgtcacgc acgaaggagg cgtaggagtc   6120
gcgcagcttg ttgaccagct cggcggtgac ctgcacgtct agggcgcagt agtccagggt   6180
ttccttgatg atgtcatact tatcctgtcc cttttttttc cacagctcgc ggttgaggac   6240
aaactcttcg cggtctttcc agtactcttg gatcggaaac ccgtcggcct ccgaacggta   6300
agagcctagc atgtagaact ggttgacggc ctggtaggcg cagcatccct tttctacggg   6360
tagcgcgtat gcctgcgcgg ccttccggag cgaggtgtgg gtgagcgcaa aggtgtccct   6420
gaccatgact ttgaggtact ggtatttgaa gtcagtgtcg tcgcatccgc cctgctccca   6480
gagcaaaaag tccgtgcgct ttttggaacg cggatttggc agggcgaagg tgacatcgtt   6540
gaagagtatc tttcccgcgc gaggcataaa gttgcgtgtg atgcggaagg gtcccggcac   6600
ctcggaacgg ttgttaatta cctgggcggc gagcacgatc tcgtcaaagc cgttgatgtt   6660
gtggcccaca atgtaaagtt ccaagaagcg cgggatgccc ttgatggaag gcaatttttt   6720
aagttcctcg taggtgagct cttcagggga gctgagcccg tgctctgaaa gggcccagtc   6780
tgcaagatga gggttggaag cgacgaatga gctccacagg tcacgggcca ttagcatttg   6840
caggtggtcg cgaaaggtcc taaactggcg acctatggcc attttttctg gggtgatgca   6900
gtagaaggta agcgggtctt gttcccagcg gtcccatcca aggttcgcgg ctaggtctcg   6960
cgcggcagtc actagaggct catctccgcc gaacttcatg accagcatga agggcacgag   7020
ctgcttccca aaggccccca tccaagtata ggtctctaca tcgtaggtga caaagagacg   7080
```

```
ctcggtgcga ggatgcgagc cgatcgggaa gaactggatc tcccgccacc aattggagga   7140
gtggctattg atgtggtgaa agtagaagtc cctgcgacgg gccgaacact cgtgctggct   7200
tttgtaaaaa cgtgcgcagt actggcagcg gtgcacgggc tgtacatcct gcacgaggtt   7260
gacctgacga ccgcgcacaa ggaagcagag tgggaatttg agccctcgc ctggcgggtt   7320
tggctggtgg tcttctactt cggctgcttg tccttgaccg tctggctgct cgaggggagt   7380
tacggtggat cggaccacca cgccgcgcga gcccaaagtc cagatgtccg cgcgcggcgg   7440
tcggagcttg atgacaacat cgcgcagatg ggagctgtcc atggtctgga gctcccgcgg   7500
cgtcaggtca ggcgggagct cctgcaggtt tacctcgcat agacgggtca gggcgcgggc   7560
tagatccagg tgatacctaa tttccagggg ctggttggtg gcggcgtcga tggcttgcaa   7620
gaggccgcat ccccgcggcg cgactacggt accgcgcggc gggcggtggg ccgcgggggt   7680
gtccttggat gatgcatcta aaagcggtga cgcgggcgag cccccggagg tagggggggc   7740
tccggacccg ccgggagagg gggcagggge acgtcggcgc cgcgcgcggg caggagctgg   7800
tgctgcgcgc gtaggttgct ggcgaacgcg acgacgcggc ggttgatctc ctgaatctgg   7860
cgcctctgcg tgaagacgac gggcccggtg agcttgagcc tgaaagagag ttcgacagaa   7920
tcaatttcgg tgtcgttgac ggcggcctgg cgcaaaatct cctgcacgtc tcctgagttg   7980
tcttgatagg cgatctcggc catgaactgc tcgatctctt cctcctggag atctccgcgt   8040
ccggctcgct ccacgtggc ggcgaggtcg ttggaaatgc gggccatgag ctgcgagaag   8100
gcgttgaggc ctccctcgtt ccagacgcgg ctgtagacca cgccccttc ggcatcgcgg   8160
gcgcgcatga ccacctgcgc gagattgagc tccacgtgcc gggcgaagac ggcgtagttt   8220
cgcaggcgct gaaagaggta gttgagggtg gtggcggtgt gttctgccac gaagaagtac   8280
ataacccagc gtcgcaacgt ggattcgttg atatccccca aggcctcaag cgctccatg   8340
gcctcgtaga agtccacggc gaagttgaaa aactgggagt tgcgcgccga cacggttaac   8400
tcctcctcca gaagacggat gagctcggcg acagtgtcgc gcacctcgcg ctcaaaggct   8460
acaggggcct cttcttcttc ttcaatctcc tcttccataa gggcctcccc ttcttcttct   8520
tctggcggcg gtggggagg ggggacacgg cggcgacgac ggcgcaccgg gaggcggtcg   8580
acaaagcgct cgatcatctc cccgcggcga cggcgcatgg tctcggtgac ggcgcggccg   8640
ttctcgcggg ggcgcagttg gaagacgccg cccgtcatgt cccggttatg ggttggcggg   8700
gggctgccat gcggcaggga tacggcgcta acgatgcatc tcaacaattg ttgtgtaggt   8760
actccgccgc cgagggacct gagcgagtcc gcatcgaccg gatcggaaaa cctctcgaga   8820
aaggcgtcta accagtcaca gtcgcaaggt aggctgagca ccgtggcggg cggcagcggg   8880
cggcggtcgg ggttgtttct ggcggaggtg ctgctgatga tgtaattaaa gtaggcggtc   8940
ttgagacggc ggatggtcga cagaagcacc atgtccttgg gtccggcctg ctgaatgcgc   9000
aggcggtcgg ccatgcccca ggcttcgttt tgacatcggc gcaggtcttt gtagtagtct   9060
tgcatgagcc tttctaccgg cacttcttct tctccttcct cttgtcctgc atctcttgca   9120
tctatcgctg cggcggcggc ggagtttggc cgtaggtggc gccctcttcc tcccatgcgt   9180
gtgaccccga agcccctcat cggctgaagc agggctaggt cggcgacaac gcgctcggct   9240
aatatggcct gctgcacctg cgtgagggta gactggaagt catccatgtc cacaaagcgg   9300
tggtatcgcg ccgtcgttgat ggtgtaagtc cagttggcca taacggacca gttaacggtc   9360
tggtgacccg gctgcgagag ctcggtgtac ctgagacgcg agtaagccct cgagtcaaat   9420
acgtagtcgt tgcaagtccg caccaggtac tggtatccca ccaaaaagtg cggcggcggc   9480
```

```
tggcggtaga ggggccagcg tagggtggcc ggggctccgg gggcgagatc ttccaacata   9540
aggcgatgat atccgtagat gtacctggac atccaggtga tgccggcggc ggtggtggag   9600
gcgcgcggaa agtcgcggac gcggttccag atgttgcgca gcggcaaaaa gtgctccatg   9660
gtcgggacgc tctggccggt caggcgcgcg caatcgttga cgctctaccg tgcaaaagga   9720
gagcctgtaa gcgggcactc ttccgtggtc tggtggataa attcgcaagg gtatcatggc   9780
ggacgaccgg ggttcgagcc ccgtatccgg ccgtccgccg tgatccatgc ggttaccgcc   9840
cgcgtgtcga acccaggtgt gcgacgtcag acaacggggg agtgctcctt ttggcttcct   9900
tccaggcgcg gcggctgctg cgctagcttt tttggccact ggccgcgcgc agcgtaagcg   9960
gttaggctgg aaagcgaaag cattaagtgg ctcgctccct gtagccggag ggttattttc  10020
caagggttga gtcgcgggac ccccggttcg agtctcggac cggccggact gcggcgaacg  10080
ggggtttgcc tccccgtcat gcaagacccc gcttgcaaat tcctccggaa acagggacga  10140
gccccttttt tgcttttccc agatgcatcc ggtgctgcgg cagatgcgcc cccctcctca  10200
gcagcggcaa gagcaagagc agcggcagac atgcagggca ccctcccctc ctcctaccgc  10260
gtcaggaggg gcgacatccg cggttgacgc ggcagcagat ggtgattacg aaccccgcg   10320
gcgccgggcc cggcactacc tggacttgga ggagggcgag ggcctggcgc ggctaggagc  10380
gccctctcct gagcggtacc caaggggtgca gctgaagcgt gatacgcgtg aggcgtacgt  10440
gccgcggcag aacctgtttc gcgaccgcga gggagaggag cccgaggaga tgcgggatcg  10500
aaagttccac gcagggcgcg agctgcggca tggcctgaat cgcgagcggt tgctgcgcga  10560
ggaggacttt gagcccgacg cgcgaaccgg gattagtccc gcgcgcgcac acgtggcggc  10620
cgccgacctg gtaaccgcat acgagcagac ggtgaaccag gagattaact ttcaaaaaag  10680
ctttaacaac cacgtgcgta cgcttgtggc gcgcgaggag gtggctatag gactgatgca  10740
tctgtgggac tttgtaagcg cgctggagca aaacccaaat agcaagccgc tcatggcgca  10800
gctgttcctt atagtgcagc acagcaggga caacgaggca ttcagggatg cgctgctaaa  10860
catagtagag cccgagggcc gctggctgct cgatttgata aacatcctgc agagcatagt  10920
ggtgcaggag cgcagcttga gcctggctga caaggtggcc gccatcaact attccatgct  10980
tagcctgggc aagttttacg cccgcaagat ataccatacc ccttacgttc ccatagacaa  11040
ggaggtaaag atcgaggggt tctacatgcg catggcgctg aaggtgctta ccttgagcga  11100
cgacctgggc gtttatcgca acgagcgcat ccacaaggcc gtgagcgtga gccggcggcg  11160
cgagctcagc gaccgcgagc tgatgcacag cctgcaaagg gccctggctg cacgggcag   11220
cggcgataga gaggccgagt cctactttga cgcgggcgct gacctgcgct gggccccaag  11280
ccgacgcgcc ctggaggcag ctggggccgg acctgggctg gcggtggcac ccgcgcgcgc  11340
tggcaacgtc ggcggcgtgg aggaatatga cgaggacgat gagtacgagc cagaggacgg  11400
cgagtactaa gcggtgatgt ttctgatcag atgatgcaag acgcaacgga cccggcggtg  11460
cgggcggcgc tgcagagcca gccgtccggc cttaactcca cggacgactg gccgcaggtc  11520
atggaccgca tcatgtcgct gactgcgcgc aatcctgacg cgttccggca gcagccgcag  11580
gccaaccggc tctccgcaat tctggaagcg gtggtcccgg cgcgcgcaaa ccccacgcac  11640
gagaaggtgc tggcgatcgt aaacgcgctg ccgaaaaaca gggccatccg gccgacgag   11700
gccgcctgg tctacgacgc gctgcttcag cgcgtggctc gttacaacag cggcaacgtg   11760
cagaccaacc tggaccggct ggtgggggat gtgcgcgagg ccgtggcgca gcgtgagcgc  11820
```

```
gcgcagcagc agggcaacct gggctccatg gttgcactaa acgccttcct gagtacacag    11880
cccgccaacg tgccgcgggg acaggaggac tacaccaact ttgtgagcgc actgcggcta    11940
atggtgactg agacaccgca aagtgaggtg taccagtctg ggccagacta ttttttccag    12000
accagtagac aaggcctgca gaccgtaaac ctgagccagg ctttcaaaaa cttgcagggg    12060
ctgtgggggg tgcgggctcc cacaggcgac cgcgcgaccg tgtctagctt gctgacgccc    12120
aactcgcgcc tgttgctgct gctaatagcg cccttcacgg acagtggcag cgtgtcccgg    12180
gacacatacc taggtcactt gctgacactg taccgcgagg ccataggtca ggcgcatgtg    12240
gacgagcata ctttccagga gattacaagt gtcagccgcg cgctggggca ggaggacacg    12300
ggcagcctgg aggcaaccct aaactacctg ctgaccaacc ggcggcagaa gatcccctcg    12360
ttgcacagtt taaacagcga ggaggagcgc attttgcgct acgtgcagca gagcgtgagc    12420
cttaacctga tgcgcgacgg ggtaacgccc agcgtggcgc tggacatgac cgcgcgcaac    12480
atggaaccgg gcatgtatgc ctcaaaccgg ccgtttatca accgcctaat ggactacttg    12540
catcgcgcgg ccgccgtgaa ccccgagtat ttcaccaatg ccatcttgaa cccgcactgg    12600
ctaccgcccc ctggttttcta caccggggga ttcgaggtgc ccgagggtaa cgatggattc    12660 ctctgggacac acatagacga cagcgtgttt tccccgcaac cgcagaccct gctagagttg    12720
caacagcgcg agcaggcaga ggcggcgctg cgaaaggaaa gcttccgcag gccaagcagc    12780
ttgtccgatc taggcgctgc ggccccgcgg tcagatgcta gtagcccatt ccaagcttg    12840 atagggtctc ttaccagcac tcgcaccacc cgcccgcgcc tgctgggcga ggaggagtac    12900
ctaaacaact cgctgctgca gccgcagcgc gaaaaaaacc tgcctccggc atttcccaac    12960
aacgggatag agagcctagt ggacaagatg agtagatgga agacgtacgc gcaggagcac    13020
agggacgtgc caggcccgcg cccgcccacc cgtcgtcaaa ggcacgaccg tcagcggggt    13080
ctggtgtggg aggacgatga ctcggcagac gacagcagcg tcctggattt gggagggagt    13140
ggcaacccgt ttgcgcacct tcgccccagg ctggggagaa tgttttaaaa aaaaaaaagc    13200
atgatgcaaa ataaaaaact caccaaggcc atggcaccga cgttggtttt cttgtattc    13260 ccccttagtat gcggcgcgcg cgatgtatg aggaaggtcc tcctcctcc tacgagagtg    13320 tggtgagcgc ggcgccagtg gcggcggcgc tgggttctcc cttcgatgct ccctggacc    13380 cgccgtttgt gcctccgcgg tacctgcggc ctaccggggg gagaaacagc atccgttact    13440
ctgagttggc accctattc gacaccaccc gtgtgtacct ggtggacaac aagtcaacgg    13500
atgtggcatc cctgaactac cagaacgacc acagcaactt tctgaccacg gtcattcaaa    13560
acaatgacta cagcccgggg gaggcaagca cacagaccat caatcttgac gaccggtcgc    13620
actggggcgg cgacctgaaa accatcctgc ataccaacat gccaaatgtg aacgagttca    13680
tgtttaccaa taagtttaag gcgcgggtga tggtgtcgcg cttgcctact aaggacaatc    13740
aggtggagct gaaatacgag tgggtggagt tcacgctgcc cgaggcaac tactccgaga    13800 ccatgaccat agaccttatg aacaacgcga tcgtggagca ctacttgaaa gtgggcagac    13860
agaacggggt tctggaaagc gacatcgggg taaagtttga caccgcaac ttcagactgg    13920 ggttgaccc cgtcactggt cttgtcatgc ctggggtata tacaaacgaa gccttccatc    13980
cagacatcat tttgctgcca ggatgcgggg tggacttcac ccacagccgc ctgagcaact    14040
tgttgggcat ccgcaagcgg caacccttcc aggagggctt taggatcacc tacgatgatc    14100 tggaggggtgg taacattccc gcactgttgg atgtggacgc ctaccaggcg agcttgaaag    14160
atgacaccga acagggcggg ggtggcgcag gcggcagcaa cagcagtggc agcggcgcgg    14220
```

```
aagagaactc caacgcggca gccgcggcaa tgcagccggt ggaggacatg aacgatcatg   14280
ccattcgcgg cgacaccttt gccacacggg ctgaggagaa gcgcgctgag gccgaagcag   14340
cggccgaagc tgccgccccc gctgcgcaac ccgaggtcga aagcctcag aagaaaccgg    14400 tgatcaaacc cctgacagag gacagcaaga aacgcagtta caacctaata agcaatgaca   14460
gcaccttcac ccagtaccgc agctggtacc ttgcatacaa ctacggcgac cctcagaccg   14520
gaatccgctc atggaccctg ctttgcactc ctgacgtaac ctgcggctcg gagcaggtct   14580
actggtcgtt gccagacatg atgcaagacc ccgtgacctt ccgctccacg cgccagatca   14640 gcaacttttcc ggtggtgggc gccgagctgt tgcccgtgca ctccaagagc ttctacaacg  14700
accaggccgt ctactcccaa ctcatccgcc agtttacctc tctgacccac gtgttcaatc   14760
gctttcccga gaaccagatt ttggcgcgcc cgccagcccc caccatcacc accgtcagtg   14820
aaaacgttcc tgctctcaca gatcacggga cgctaccgct gcgcaacagc atcggaggag   14880
tccagcgagt gaccattact gacgccgac gccgcacctg cccctacgtt tacaaggccc    14940
tgggcatagt ctcgccgcgc gtcctatcga gccgcacttt tgagcaagc atgtccatcc    15000 ttatatcgcc cagcaataac acaggctggg gcctgcgctt cccaagcaag atgtttggcg   15060 ggccaagaa gcgctccgac caacacccag tgcgcgtgcg cgggcactac cgcgcgccct   15120
ggggcgcgca caaacgcggc cgcactgggc gcaccaccgt cgatgacgcc atcgacgcgg   15180
tggtggagga ggcgcgcaac tacacgccca cgccgccacc agtgtccaca gtggacgcgg   15240
ccattcagac cgtggtgcgc ggagcccggc gctatgctaa aatgaagaga cggcggaggc   15300
gcgtagcacg tcgccaccgc cgccgacccg gcactgccgc ccaacgcgcg cggcggcccc   15360
tgcttaaccg cgcacgtcgc accggccgac gggcggccat gcgggccgct cgaaggctgg   15420
ccgcgggtat tgtcactgtg cccccaggt ccaggcgacg agcggccgcc gcagcagccg    15480
cggccattag tgctatgact cagggtcgca ggggcaacgt gtattgggtg cgcgactcgg   15540
ttagcggcct gcgcgtgccc gtgcgcaccc gcccccgcg caactagatt gcaagaaaaa    15600
actacttaga ctcgtactgt tgtatgtatc cagcggcggc ggcgcgcaac gaagctatgt   15660
ccaagcgcaa aatcaaagaa gagatgctcc aggtcatcgc gccggagatc tatggccccc   15720
cgaagaagga agagcaggat tacaagcccc gaaagctaaa gcgggtcaaa agaaaaaga   15780 aagatgatga tgatgaactt gacgacgagg tggaactgct gcacgctacc gcgcccaggc   15840
gacgggtaca gtggaaaggt cgacgcgtaa aacgtgtttt gcgacccggc accaccgtag   15900
tctttacgcc cggtgagcgc tccacccgca cctacaagcg cgtgtatgat gaggtgtacg   15960
gcgacgagga cctgcttgag caggccaacg agcgcctcgg ggagtttgcc tacggaaagc   16020
ggcataagga catgctggcg ttgccgctgg acgagggcaa cccaacacct agcctaaagc   16080
ccgtaacact gcagcaggtg ctgccccgcgc ttgcaccgtc cgaagaaaag cgcggcctaa   16140
agcgcgagtc tggtgacttg gcacccaccg tgcagctgat ggtacccaag cgccagcgac   16200
tggaagatgt cttggaaaaa atgaccgtgg aacctgggct ggagcccgag gtccgcgtgc   16260
ggccaatcaa gcaggtggcg ccgggactgg gcgtgcagac cgtggacgtt cagatacccca  16320 ctaccagtag caccagtatt gccaccgcca cagagggcat ggagacacaa acgtccccgg   16380
ttgcctcagc ggtggcggat gccgcggtgc aggcggtcgc tgcggccgcg tccaagacct   16440
ctacggaggt gcaaacggac ccgtggatgt ttcgcgtttc agcccccggg cgcccgcgcg   16500
gttcgaggaa gtacggcgcc gccagcgcgc tactgccccga atatgcccta catccttcca   16560
```

```
ttgcgcctac ccccggctat cgtggctaca cctaccgccc cagaagacga gcaactaccc   16620
gacgccgaac caccactgga acccgccgcc gccgtcgccg tcgccagccc gtgctggccc   16680
cgatttccgt gcgcagggtg gctcgcgaag gaggcaggac cctggtgctg ccaacagcgc   16740
gctaccaccc cagcatcgtt taaaagccgg tctttgtggt tcttgcagat atggccctca   16800
cctgccgcct ccgtttcccg gtgccgggat tccgaggaag aatgcaccgt aggaggggca   16860
tggccggcca cggcctgacg ggcggcatgc gtcgtgcgca ccaccggcgg cggcgcgcgt   16920
cgcaccgtcg catgcgcggc ggtatcctgc ccctccttat tccactgatc gccgcggcga   16980
ttggcgccgt gcccggaatt gcatccgtgg ccttgcaggc gcagagacac tgattaaaaa   17040
caagttgcat gtggaaaaat caaaataaaa agtctggact ctcacgctcg cttggtcctg   17100
taactatttt gtagaatgga agacatcaac tttgcgtctc tggccccgcg cacggctcg    17160 cgcccgttca tgggaaactg gcaagatatc ggcaccagca atatgagcgg tggcgccttc   17220
agctggggct cgctgtggag cggcattaaa aatttcggtt ccaccgttaa gaactatggc   17280
agcaaggcct ggaacagcag cacaggccag atgctgaggg ataagttgaa agagcaaaat   17340
ttccaacaaa aggtggtaga tggcctggcc tctggcatta gcggggtggt ggacctggcc   17400
aaccaggcag tgcaaaataa gattaacagt aagcttgatc cccgccctcc cgtagaggag   17460
cctccaccgg ccgtggagac agtgtctcca gagggcgtg gcgaaaagcg tccgcgcccc    17520
gacagggaag aaactctggt gacgcaaata gacgagcctc cctcgtacga ggaggcacta   17580
aagcaaggcc tgcccaccac ccgtcccatc gcgcccatgg ctaccggagt gctgggccag   17640
cacacacccg taacgctgga cctgcctccc ccgccgaca cccagcagaa acctgtgctg    17700
ccaggcccga ccgccgttgt tgtaacccgt cctagccgcg cgtccctgcg ccgcgccgcc   17760
agcggtccgc gatcgttgcg gcccgtagcc agtggcaact ggcaaagcac actgaacagc   17820
atcgtgggtc tgggggtgca atccctgaag cgccgacgat gcttctgaat agctaacgtg   17880
tcgtatgtgt gtcatgtatg cgtccatgtc gccgccagag gagctgctga caagtttgta   17940 caaaaagca ggcttcgaag gagatagaac caattctcta aggaaatact taaccatggc    18000
tctagaccgc cgcgcggccg cttttccaaga tggctacccc ttcgatgatg ccgcagtggt  18060
cttacatgca catctcgggc caggacgcct cggagtacct gagccccggg ctggtgcagt   18120
ttgcccgcgc caccgagacg tacttcagcc tgaataacaa gtttagaaac cccacggtgg   18180
cgcctacgca cgacgtgacc acagaccggt cccagcgttt gacgctgcgg ttcatccctg   18240
tggaccgtga ggatactgcg tactcgtaca aggcgcggtt caccctagct gtgggtgata   18300
accgtgtgct ggacatggct tccacgtact ttgacatccg cggcgtgctg acaggggcc    18360 ctacttttaa gccctactct ggcactgcct acaacgccct ggctcccaag ggtgccccaa   18420
atccttgcga atgggaagag aaaaagaatg gaggaggaag cgatgctaat caaatgcaaa   18480
ctcacgtatt tgggcaggcg ccttattctg gtataaatat tacaaaggag ggtattcaaa   18540
taggtattga tgcaaccaaa gaggaagata atggaaagga aatatatgcc gataaaacat   18600
ttcaacctga acctcaaata ggagaatctc agtggcagga tagtgataat tactatggag   18660
ggagagtcct taaaaagact accccaatga aaccatgtta cggttcatat gcaaaaccca   18720
caaatgaaaa tggagggcaa gctaaattca aaacacctga aaagaaggt gaagaaccca   18780 aagaaagtca agtggaaatg caattttcg atattcccag tactggcaca ggtggtaatg    18840
gaacaaatgt taatttcaaa cctaaagtgg tattgtacag tgaagatgta gatatagaaa   18900
ccccagacac tcatatttct tacatgcccg gcaaggaaga tgcaagttca cgagaactaa   18960
```

```
tgggccaaca atctatgccc aacaggccta attacattgc ttttagggac aattttattg   19020
gtctaatgta ttacaacagc acgggtaata tgggtgttct ggcgggccaa gcatcgcagt   19080
tgaatgctgt tgtagatttg caagacagaa acacagagct ttcataccag cttttgcttg   19140
attccattgg tgatagaacc aggtactttt ctatgtggaa tcaggctgtt gacagctatg   19200
atccagatgt tagaattatt gaaaatcatg gaactgaaga tgaacttcca aattactgct   19260
ttccactgga tggcgctgga actaacgcag tgtaccaagg tgtaaaagtt aaaactacta   19320
acaatacaga atgggaaaaa gacactgcag tatctgaaca caatcagata agagttggaa   19380
ataattttgc catggaaatc aatctaaatg ccaacctgtg gagaaatttc ctgtactcca   19440
acatagcgct gtatttgccc gacaagctaa agtacagtcc ttccaacgta aaaatttctg   19500
ataacccaaa cacctacgac tacatgaaca agcgagtggg ggctcccggg ttagtggact   19560
gctacattaa ccttggagca cgctggtccc ttgactatat ggacaacgtc aacccattta   19620
accaccaccg caatgctggc ctgcgctacc gctcaatgtt gctgggcaat ggtcgctatg   19680
tgcccttcca catccaggtg cctcagaagt tctttgccat taaaaacctc cttctcctgc   19740
cgggctcata cacctacgag tggaacttca ggaaggatgt taacatggtt ctgcagagct   19800
ccctaggaaa tgacctaagg gttgacggag ccagcattaa gtttgatagc atttgccttt   19860
acgccacctt cttccccatg gcccacaaca ccgcctccac gcttgaggcc atgcttagaa   19920
acgacaccaa cgaccagtcc tttaacgact atctctccgc cgccaacatg ctctacccta   19980
tacccgccaa cgctaccaac gtgcccatat ccatcccctc ccgcaactgg gcggctttcc   20040
gcggctgggc cttcacgcgc cttaagacta aggaaacccc atcactgggc tcgggctacg   20100
acccttatta cacctactct ggctctatac cctacctaga tggaaccttt tacctcaacc   20160
acacctttaa gaaggtggcc attacctttg actcttctgt cagctggcct ggcaatgacc   20220
gcctgcttac ccccaacgag tttgaaatta agcgctcagt tgacggggag ggttacaacg   20280
ttgcccagtg taacatgacc aaagactggt tcctggtaca aatgctagct aactacaaca   20340
ttggctacca gggcttctat atcccagaga gctacaagga ccgcatgtac tccttcttta   20400
gaaacttcca gcccatgagc cgtcaggtgg tggatgatac taaatacaag gactaccaac   20460
aggtgggcat cctacaccaa cacaacaact ctggatttgt tggctacctt gcccccacca   20520
tgcgcgaagg acaggcctac cctgctaact tcccctatcc gсттатадgс aagaccgcag   20580
ttgacagcat tacccagaaa aagtttcttt gcgatcgcac cctttgdcgc atcccattct   20640
ccagtaactt tatgtccatg ggcgcactca cagacctggg ccaaaacctt ctctacgcca   20700
actccgccca cgcgctagac atgacttttg aggtggatcc catggacgag cccacccttc   20760
tttatgtttt gtttgaagtc tttgacgtgg tccgtgtgca ccggccgcac cgcggcgtca   20820
tcgaaaccgt gtacctgcgc acgcccttct cggccggcaa cgccacaaca taaagaagca   20880
agcaacatca caacagctg ccgccatggg ctccagtgag caggaactga agccattgt   20940
caaagacctt ggttgtgggc catatttttt gggcacctat gacaagcgct ttccaggctt   21000
tgtttctcca cacaagctcg cctgcgccat agtcaatacg gccggtcgcg agactggggg   21060
cgtacactgg atggccттттg cctggaaccc gcactcaaaa acatgctacc tctttgagcc   21120
ctttggcttt tctgaccagc gactcaagca ggtttaccag tttgagtacg agtcactcct   21180
gcgccgtagc gccattgctt cttcccccga ccgctgtata acgctggaaa agtccaccca   21240
aagcgtacag gggcccaact cggccgcctg tggactattc tgctgcatgt ttctccacgc   21300
```

-continued

| | | | | |
|---|---|---|---|---|
| ctttgccaac | tggccccaaa | ctcccatgga | tcacaacccc | accatgaacc ttattaccgg 21360 |
| ggtacccaac | tccatgctca | acagtcccca | ggtacagccc | accctgcgtc gcaaccagga 21420 |
| acagctctac | agcttcctgg | agcgccactc | gccctacttc | cgcagccaca gtgcgcagat 21480 |
| taggagcgcc | acttcttttt | gtcacttgaa | aaacatgtaa | aaataatgta ctagagacac 21540 |
| tttcaataaa | ggcaaatgct | tttatttgta | cactctcggg | tgattattta cccccacccct 21600 |
| tgccgtctgc | gccgtttaaa | aatcaaaggg | gttctgccgc | gcatcgctat gcgccactgg 21660 |
| cagggacacg | ttgcgatact | ggtgtttagt | gctccactta | aactcaggca caaccatccg 21720 |
| cggcagctcg | gtgaagtttt | cactccacag | gctgcgcacc | atcaccaacg cgtttagcag 21780 |
| gtcgggcgcc | gatatcttga | agtcgcagtt | ggggcctccg | ccctgcgcgc gcgagttgcg 21840 |
| atacacaggg | ttgcagcact | ggaacactat | cagcgccggg | tggtgcacgc tggccagcac 21900 |
| gctcttgtcg | gagatcagat | ccgcgtccag | gtcctccgcg | ttgctcaggg cgaacggagt 21960 |
| caactttggt | agctgccttc | ccaaaaaggg | cgcgtgccca | ggctttgagt tgcactcgca 22020 |
| ccgtagtggc | atcaaaaggt | gaccgtgccc | ggtctgggcg | ttaggataca gcgcctgcat 22080 |
| aaaagccttg | atctgcttaa | aagccacctg | agcctttgcg | ccttcagaga gaacatgcc 22140 |
| gcaagacttg | ccggaaaact | gattggccgg | acaggccgcg | tcgtgcacgc agcaccttgc 22200 |
| gtcggtgttg | gaaatctgca | ccacatttcg | gccccaccgg | ttcttcacga tcttggcctt 22260 |
| gctagactgc | tccttcagcg | cgcgctgccc | gttttcgctc | gtcacatcca tttcaatcac 22320 |
| gtgctcctta | tttatcataa | tgcttccgtg | tagacactta | agctcgcctt cgatctcagc 22380 |
| gcagcggtgc | agccacaacg | cgcagcccgt | gggctcgtga | tgcttgtagg tcacctctgc 22440 |
| aaacgactgc | aggtacgcct | gcaggaatcg | ccccatcatc | gtcacaaagg tcttgttgct 22500 |
| ggtgaaggtc | agctgcaacc | cgcggtgctc | ctcgttcagc | caggtcttgc atacggccgc 22560 |
| cagagcttcc | acttggtcag | gcagtagttt | gaagttcgcc | tttagatcgt tatccacgtg 22620 |
| gtacttgtcc | atcagcgcgc | gcgcagcctc | catgcccttc | tcccacgcag acacgatcgg 22680 |
| cacactcagc | gggttcatca | ccgtaatttc | actttccgct | tcgctgggct cttcctcttc 22740 |
| ctcttgcgtc | cgcataccac | gcgccactgg | gtcgtcttca | ttcagccgcc gcactgtgcg 22800 |
| cttacctcct | ttgccatgct | tgattagcac | cggtgggttg | ctgaaaccca ccatttgtag 22860 |
| cgccacatct | tctctttctt | cctcgctgtc | cacgattacc | tctggtgatg gcgggcgctc 22920 |
| gggcttggga | gaagggcgct | tcttttcttt | cttgggcgca | atggccaaat ccgccgccga 22980 |
| ggtcgatggc | cgcgggctgg | gtgtgcgcgg | caccagcgcg | tcttgtgatg agtcttcctc 23040 |
| gtcctcggac | tcgatacgcc | gcctcatccg | cttttttggg | ggcgcccggg gaggcggcgg 23100 |
| cgacggggac | ggggacgaca | cgtcctccat | ggttggggga | cgtcgcgccg caccgcgtcc 23160 |
| gcgctcgggg | gtggtttcgc | gctgctcctc | ttcccgactg | gccatttcct tctcctatag 23220 |
| gcagaaaaag | atcatggagt | cagtcgagaa | gaaggacagc | ctaaccgccc cctctgagtt 23280 |
| cgccaccacc | gcctccaccg | atgccgccaa | cgcgcctacc | accttccccg tcgaggcacc 23340 |
| cccgcttgag | gaggaggaag | tgattatcga | gcaggaccca | ggttttgtaa gcgaagacga 23400 |
| cgaggaccgc | tcagtaccaa | cagaggataa | aaagcaagac | caggacaacg cagaggcaaa 23460 |
| cgaggaacaa | gtcgggcggg | gggacgaaag | gcatggcgac | tacctagatg tgggagacga 23520 |
| cgtgctgttg | aagcatctgc | agcgccagtc | cgccattatc | tgcgacgcgt tgcaagagcg 23580 |
| cagcgatgtg | cccctcgcca | tagcggatgt | cagccttgcc | tacgaacgcc acctattctc 23640 |
| accgcgcgta | ccccccaaac | gccaagaaaa | cggcacatgc | gagcccaacc cgcgcctcaa 23700 |

```
cttctacccc gtatttgccg tgccagaggt gcttgccacc tatcacatct ttttccaaaa   23760
ctgcaagata cccctatcct gccgtgccaa ccgcagccga gcggacaagc agctggcctt   23820
gcggcagggc gctgtcatac ctgatatcgc ctcgctcaac gaagtgccaa aaatctttga   23880
gggtcttgga cgcgacgaga agcgcgcggc aaacgctctg caacaggaaa acagcgaaaa   23940
tgaaagtcac tctggagtgt tggtggaact cgagggtgac aacgcgcgcc tagccgtact   24000
aaaacgcagc atcgaggtca cccactttgc ctacccggca cttaacctac cccccaaggt   24060
catgagcaca gtcatgagtg agctgatcgt gcgccgtgcg cagcccctgg agagggatgc   24120
aaatttgcaa gaacaaacag aggagggcct acccgcagtt ggcgacgagc agctagcgcg   24180
ctggcttcaa acgcgcgagc ctgccgactt ggaggagcga cgcaaactaa tgatggccgc   24240
agtgctcgtt accgtggagc ttgagtgcat gcagcggttc tttgctgacc cggagatgca   24300
gcgcaagcta gaggaaacat tgcactacac ctttcgacag ggctacgtac gccaggcctg   24360
caagatctcc aacgtggagc tctgcaacct ggtctcctac cttggaattt tgcacgaaaa   24420
ccgccttggg caaaacgtgc ttcattccac gctcaagggc gaggcgcgcc gcgactacgt   24480
ccgcgactgc gtttacttat ttctatgcta cacctggcag acggccatgg gcgtttggca   24540
gcagtgcttg gaggagtgca acctcaagga gctgcagaaa ctgctaaagc aaaacttgaa   24600
ggacctatgg acggccttca acgagcgctc cgtggccgcg cacctggcgg acatcatttt   24660
ccccgaacgc ctgcttaaaa ccctgcaaca gggtctgcca gacttcacca gtcaaagcat   24720
gttgcagaac tttaggaact ttatcctaga gcgctcagga atcttgcccg ccacctgctg   24780
tgcacttcct agcgactttg tgcccattaa gtaccgcgaa tgccctccgc cgctttgggg   24840
ccactgctac cttctgcagc tagccaacta ccttgcctac cactctgaca taatggaaga   24900
cgtgagcggt gacggtctac tggagtgtca ctgtcgctgc aacctatgca cccgcaccg   24960 ctccctggtt tgcaattcgc agctgcttaa cgaaagtcaa attatcggta cctttgagct   25020
gcagggtccc tcgcctgacg aaaagtccgc ggctccgggg ttgaaactca ctccggggct   25080
gtggacgtcg gcttaccttc gcaaatttgt acctgaggac taccacgccc acgagattag   25140
gttctacgaa gaccaatccc gcccgccaaa tgcggagctt accgcctgcg tcattaccca   25200
gggccacatt cttggccaat gcaagccat caacaaagcc cgccaagagt ttctgctacg   25260
aaagggacgg ggggtttact tggacccccca gtccggcgag gagctcaacc caatcccccc   25320
gccgccgcag ccctatcagc agcagccgcg ggccccttgct tcccaggatg cacccaaaa   25380 agaagctgca gctgccgccg ccacccacgg acgaggagga atactgggac agtcaggcag   25440
aggaggtttt ggacgaggag gaggaggaca tgatggaaga ctgggagagc ctagacgagg   25500
aagcttccga ggtcgaagag gtgtcagacg aaacaccgtc accctcggtc gcattcccct   25560
cgccggcgcc ccagaaatcg gcaaccggtt ccagcatggc tacaacctcc gctcctcagg   25620
cgccgccggc actgcccgtt cgccgaccca ccgtagatg ggacaccact ggaaccaggg   25680
ccggtaagtc caagcagccg ccgccgttag cccaagagca acaacagcgc caaggctacc   25740
gctcatggcg cgggcacaag aacgccatag ttgcttgctt gcaagactgt ggggcaaca   25800 tctccttcgc ccgccgcttt cttctctacc atcacgcgt ggccttcccc cgtaacatcc   25860
tgcattacta ccgtcatctc tacagcccat actgcaccgg cggcagcggc agcggcagca   25920
acagcagcgg ccacacagaa gcaaaggcga ccggatagca agactctgac aaagcccaag   25980
aaatccacag cggcggcagc agcaggagga ggagcgctgc gtctggcgcc caacgaaccc   26040
```

```
gtatcgaccc gcgagcttag aaacaggatt tttcccactc tgtatgctat atttcaacag   26100
agcaggggcc aagaacaaga gctgaaaata aaaaacaggt ctctgcgatc cctcacccgc   26160
agctgcctgt atcacaaaag cgaagatcag cttcggcgca cgctggaaga cgcggaggct   26220
ctcttcagta aatactgcgc gctgactctt aaggactagt ttcgcgccct ttctcaaatt   26280
taagcgcgaa aactacgtca tctccagcgg ccacacccgg cgccagcacc tgtcgtcagc   26340
gccattatga gcaaggaaat tcccacgccc tacatgtgga gttaccagcc acaaatggga   26400
cttgcggctg gagctgccca agactactca acccgaataa actacatgag cgcgggaccc   26460
cacatgatat cccgggtcaa cggaatccgc gcccaccgaa accgaattct cttggaacag   26520
gcggctatta ccaccacacc tcgtaataac cttaatcccc gtagttggcc cgctgccctg   26580
gtgtaccagg aaagtcccgc tcccaccact gtggtacttc ccagagacgc ccaggccgaa   26640
gttcagatga ctaactcagg ggcgcagctt gcgggcggct ttcgtcacag ggtgcggtcg   26700
cccgggcagg gtataactca cctgacaatc agagggcgag gtattcagct caacgacgag   26760
tcggtgagct cctcgcttgg tctccgtccg gacgggacat ttcagatcgg cggcgccggc   26820
cgtccttcat tcacgcctcg tcaggcaatc ctaactctgc agacctcgtc ctctgagccg   26880
cgctctggag gcattggaac tctgcaattt attgaggagt ttgtgccatc ggtctacttt   26940
aaccccttct cgggacctcc cggccactat ccggatcaat ttattcctaa ctttgacgcg   27000
gtaaaggact cggcggacgg ctacgactga atgttaagtg gagaggcaga gcaactgcgc   27060
ctgaaacacc tggtccactg tcgccgccac aagtgctttg cccgcgactc cggtgagttt   27120
tgctactttg aattgcccga ggatcatatc gagggcccgg cgcacggcgt ccggcttacc   27180
gcccagggag agcttgcccg tagcctgatt cgggagttta cccagcgccc cctgctagtt   27240
gagcgggaca ggggacccctg tgttctcact gtgatttgca actgtcctaa ccttggatta   27300
catcaagatc ctctagttaa ttaagatatc tgagtcatta gggactttcc aatgggtttt   27360
gcccagtaca taaggtcaat aggggtgaat caacaggaaa gtcccattgg agccaagtac   27420
actgagtcaa tagggacttt ccattgggtt ttgcccagta caaaaggtca ataggggtg   27480 agtcaatggg ttttttcccat tattggcacg tacataaggt caataggggt gagtcattgg   27540 gttttttccag ccatttaatt aaaacgccat gtactttccc accattgacg tcaatgggct   27600
attgaaacta atgcaacgtg acctttaaac ggtactttcc catagctgat taatgggaaa   27660
gtaccgttct cgagccaata cacgtcaatg ggaagtgaaa gggcagccaa aacgtaacac   27720
cgccccggtt ttcccctgga aattccatat tggcactcat tctattggct gagctgcgtt   27780
ctacgtgggt ataagaggcg cgaccagcgt cggtaccgtc gcagtcttcg gtctgaccac   27840
cgtagaacgc agatcgaatt actagtcagg gaattcggta ccgctagcca tggacgcgtt   27900
aaccggtgat atcgatagat ctcatatgga tccagcttgt cgacttcgag caacttgttt   27960
attgcagctt ataatggtta caaataaagc aatagcatca caaatttcac aaataaagca   28020 ttttttttcac tgcattctag ttgtggtttg tccaaactca tcaatgtatc ttatcatgtc   28080
tggatcgtct agcatcgaag atcctagcaa atttctgtcc agtttattca gcagcacctc   28140
cttgccctcc tcccagctct ggtattgcag cttcctcctg gctgcaaact ttctccacaa   28200
tctaaatgga atgtcagttt cctcctgttc ctgtccatcc gcacccacta tcttcatgtt   28260
gtgcaccatg aagcgcgcaa gaccgtctga agataccttc aaccccgtgt atccatatga   28320
cacggaaacc ggtcctccaa ctgtgccttt tcttactcct cccttttgtat cccccaatgg   28380 gtttcaagag agtccccctg gagttcttac tttaaaatgt ttaaccccac taacaaccac   28440
```

```
aggcggatct ctacagctaa aagtgggagg gggacttaca gtggatgaca ccaacggttt   28500
tttgaaagaa aacataagtg ccaccacacc actcgttaag actggtcact ctataggttt   28560
accactagga gccggattgg gaacgaatga aaataaactt tgtatcaaat taggacaagg   28620
acttacattc aattcaaaca acatttgcat tgatgacaat attaacacct tatggacagg   28680
agtcaacccc accgaagcca actgtcaaat catgaactcc agtgaatcta atgattgcaa   28740
attaattcta acactagtta aaactggagc actagtcact gcatttgttt atgttatagg   28800
agtatctaac aattttaata tgctaactac acacagaaat ataaattta ctgcagagct    28860 gttttcgat tctaactggt aatttaacta actagactct catcccctca aaactccact    28920
taatcataaa tcaggacaaa acatggctac tggtgccatt actaatgcta aaggtttcat   28980
gcccagcacg actgcctatc ctttcaatga taattctaga gaaaagaaa actacattta    29040 cggaacttgt tactacacag ctagtgatcg cactgctttt cccattgaca tatctgtcat   29100
gcttaaccga agagcaataa atgacgagac atcatattgt attcgtataa cttggtcctg   29160
gaacacagga gatgccccag aggtgcaaac ctctgctaca accctagtca cctccccatt   29220
taccttttac tacatcagag aagacgacta aagaatcgtt tgtgttatgt ttcaacgtgt   29280
ttatttttca attgcagaaa atttcaagtc attttttcatt cagtagtata ctctagaccc   29340
agctttcttg tacaaagtgg tcatagctta tacagatcac cgtaccttaa tcaaactcac   29400
agaaccctag tattcaacct gccacctccc tcccaacaca cagagtacac agtcctttct   29460
ccccggctgg ccttaaaaag catcatatca tgggtaacag acatattctt aggtgttata   29520
ttccacacgg tttcctgtcg agccaaacgc tcatcagtga tattaataaa ctccccgggc   29580
agctcactta agttcatgtc gctgtccagc tgctgagcca caggctgctg tccaacttgc   29640
ggttgcttaa cgggcggcga aggagaagtc cacgcctaca tgggggtaga gtcataatcg   29700
tgcatcagga tagggcggtg gtgctgcagc agcgcgcgaa taaactgctg ccgccgccgc   29760
tccgtcctgc aggaatacaa catggcagtg gtctcctcag cgatgattcg caccgcccgc   29820
agcataaggc gccttgtcct ccgggcacag cagcgcaccc tgatctcact taaatcagca   29880
cagtaactgc agcacagcac cacaatattg ttcaaaatcc cacagtgcaa ggcgctgtat   29940
ccaaagctca tggcggggac cacagaaccc acgtggccat cataccacaa gcgcaggtag   30000
attaagtggc gaccccctcat aaacacgctg gacataaaca ttacctcttt tggcatgttg   30060
taattcacca cctcccggta ccatataaac ctctgattaa acatggcgcc atccaccacc   30120
atcctaaacc agctggccaa aacctgcccg ccggctatac actgcaggga accgggactg   30180
gaacaatgac agtggagagc ccaggactcg taaccatgga tcatcatgct cgtcatgata   30240
tcaatgttgg cacaacacag gcacacgtgc atacacttcc tcaggattac aagctcctcc   30300
cgcgttagaa ccatatccca gggaacaacc cattcctgaa tcagcgtaaa tcccacactg   30360
cagggaagac ctcgcacgta actcacgttg tgcattgtca aagtgttaca ttcgggcagc   30420
agcggatgat cctccagtat ggtagcgcgg gtttctgtct caaaaggagg tagacgatcc   30480
ctactgtacg gagtgcgccg agacaaccga gatcgtgttg gtcgtagtgt catgccaaat   30540
ggaacgccgg acgtagtcat atttcctgaa gcaaaaccag gtgcgggcgt gacaaacaga   30600
tctgcgtctc cggtctcgcc gcttagatcg ctctgtgtag tagttgtagt atatccactc   30660
tctcaaagca tccaggcgcc ccctggcttc gggttctatg taaactcctt catgcgccgc   30720
tgccctgata acatccacca ccgcagaata agccacaccc agccaaccta cacattcgtt   30780
```

-continued

| | |
|---|---|
| ctgcgagtca cacacgggag gagcgggaag agctggaaga accatgtttt tttttttatt | 30840 |
| ccaaaagatt atccaaaacc tcaaaatgaa gatctattaa gtgaacgcgc tccctccgg | 30900 |
| tggcgtggtc aaactctaca gccaaagaac agataatggc atttgtaaga tgttgcacaa | 30960 |
| tggcttccaa aaggcaaacg gccctcacgt ccaagtggac gtaaaggcta aacccttcag | 31020 |
| ggtgaatctc ctctataaac attccagcac cttcaaccat gcccaaataa ttctcatctc | 31080 |
| gccaccttct caatatatct ctaagcaaat cccgaatatt aagtccggcc attgtaaaaa | 31140 |
| tctgctccag agcgccctcc accttcagcc tcaagcagcg aatcatgatt gcaaaaattc | 31200 |
| aggttcctca cagacctgta taagattcaa aagcggaaca ttaacaaaaa taccgcgatc | 31260 |
| ccgtaggtcc cttcgcaggg ccagctgaac ataatcgtgc aggtctgcac ggaccagcgc | 31320 |
| ggccacttcc ccgccaggaa ccttgacaaa agaacccaca ctgattatga cacgcatact | 31380 |
| cggagctatg ctaaccagcg tagccccgat gtaagctttg ttgcatgggc ggcgatataa | 31440 |
| aatgcaaggt gctgctcaaa aaatcaggca aagcctcgcg caaaaaagaa agcacatcgt | 31500 |
| agtcatgctc atgcagataa aggcaggtaa gctccggaac caccacagaa aaagacacca | 31560 |
| ttttctctc aaacatgtct gcgggtttct gcataaacac aaaataaaat aacaaaaaaa | 31620 |
| catttaaaca ttagaagcct gtcttacaac aggaaaaaca acccttataa gcataagacg | 31680 |
| gactacggcc atgccggcgt gaccgtaaaa aaactggtca ccgtgattaa aaagcaccac | 31740 |
| cgacagctcc tcggtcatgt ccggagtcat aatgtaagac tcggtaaaca catcaggttg | 31800 |
| attcatcggt cagtgctaaa aagcgaccga atagcccgg gggaatacat acccgcaggc | 31860 |
| gtagagacaa cattacagcc cccataggag gtataacaaa attaatagga gagaaaaaca | 31920 |
| cataaacacc tgaaaaaccc tcctgcctag gcaaaatagc accctcccgc tccagaacaa | 31980 |
| catacagcgc ttcacagcgg cagcctaaca gtcagcctta ccagtaaaaaa agaaaaccta | 32040 |
| ttaaaaaaac accactcgac acggcaccag ctcaatcagt cacagtgtaa aaaagggcca | 32100 |
| agtgcagagc gagtatatat aggactaaaa aatgacgtaa cggttaaagt ccacaaaaaa | 32160 |
| cacccagaaa accgcacgcg aacctacgcc cagaaacgaa agccaaaaaa cccacaactt | 32220 |
| cctcaaatcg tcacttccgt tttcccacgt tacgtaactt cccattttaa gaaaactaca | 32280 |
| attcccaaca catacaagtt actccgccct aaaacctacg tcacccgccc cgttcccacg | 32340 |
| ccccgcgcca cgtcacaaac tccacccct cattatcata ttggcttcaa tccaaaataa | 32400 |
| ggtatattat tgatgat | 32417 |

<210> SEQ ID NO 5
<211> LENGTH: 2844
<212> TYPE: DNA
<213> ORGANISM: Artificial
<220> FEATURE:
<223> OTHER INFORMATION: Ad5H48 chimeric Hexon

<400> SEQUENCE: 5

| | |
|---|---|
| atggctaccc cttcgatgat gccgcagtgg tcttacatgc acatctcggg ccaggacgcc | 60 |
| tcggagtacc tgagccccgg gctggtgcag tttgcccgcg ccaccgagac gtacttcagc | 120 |
| ctgaataaca agtttagaaa ccccacggtg cgcctacgc acgacgtgac cacagaccgg | 180 |
| tcccagcgtt tgacgctgcg gttcatccct gtggaccgtg aggatactgc gtactcgtac | 240 |
| aaggcgcggt tcaccctagc tgtgggtgat aaccgtgtgc tggacatggc ttccacgtac | 300 |
| tttgacatcc gcgcgtgct ggacagggc cctacttta gccctactc tggcactgcc | 360 |
| tacaacgccc tggctcccaa gggtgcccca aatccttgcg aatgggaaga gaaaagaat | 420 |

```
ggaggaggaa gcgatgctaa tcaaatgcaa actcacgtat ttgggcaggc gccttattct    480
ggtataaata ttacaaagga gggtattcaa ataggtattg atgcaaccaa agaggaagat    540
aatggaaagg aaatatatgc cgataaaaca tttcaacctg aacctcaaat aggagaatct    600
cagtggcagg atagtgataa ttactatgga gggagagtcc ttaaaaagac taccccaatg    660
aaaccatgtt acggttcata tgcaaaaccc acaaatgaaa atggagggca agctaaattc    720
aaaacacctg aaaagaagg tgaagaaccc aagaaagtc aagtggaaat gcaattttc     780 gatattccca gtactggcac aggtggtaat ggaacaaatg ttaatttcaa acctaaagtg    840
gtattgtaca gtgaagatgt agatatagaa accccagaca ctcatatttc ttacatgccc    900
ggcaaggaag atgcaagttc acgagaacta atgggccaac aatctatgcc aacaggcct     960 aattacattg cttttaggga caatttattt ggtctaatgt attacaacag cacgggtaat    1020
atgggtgttc tggcgggcca agcatcgcag ttgaatgctg ttgtagattt gcaagacaga    1080
aacacagagc tttcatacca gcttttgctt gattccattg gtgatagaac caggtactt     1140 tctatgtgga atcaggctgt tgacagctat gatccagatg ttagaattat tgaaaatcat    1200
ggaactgaag atgaacttcc aaattactgc tttccactgg atggcgctgg aactaacgca    1260
gtgtaccaag gtgtaaaagt taaaactact aacaatacag aatgggaaaa agacactgca    1320
gtatctgaac acaatcagat aagagttgga aataattttg ccatggaaat caatctaaat    1380
gccaacctgt ggagaaattt cctgtactcc aacatagcgc tgtatttgcc cgacaagcta    1440
aagtacagtc cttccaacgt aaaaatttct gataacccaa acacctacga ctacatgaac    1500
aagcgagtgg tggctcccgg gttagtggac tgctacatta accttggagc acgctggtcc    1560
cttgactata tggacaacgt caacccattt aaccaccacc gcaatgctgg cctgcgctac    1620
cgctcaatgt tgctgggcaa tggtcgctat gtgcccttcc acatccaggt gcctcagaag    1680
ttctttgcca ttaaaaacct ccttctcctg ccgggctcat acacctacga gtggaacttc    1740
aggaaggatg ttaacatggt tctgcagagc tccctaggaa atgacctaag ggttgacgga    1800
gccagcatta agtttgatag catttgcctt tacgccacct tcttccccat ggcccacaac    1860
accgcctcca cgcttgaggc catgcttaga acgacacca acgaccagtc ctttaacgac    1920
tatctctccg ccgccaacat gctctaccct atacccgcca acgctaccaa cgtgcccata    1980
tccatcccct cccgcaactg gcggcttttc cgcggctggg ccttcacgcg ccttaagact    2040
aaggaaaccc catcactggg ctcgggctac gaccttatt acacctactc tggctctata    2100
ccctacctag atggaaacctt ttacctcaac cacacctta agaaggtggc cattaccttt    2160
gactcttctg tcagctggcc tggcaatgac cgcctgctta cccccaacga gtttgaaatt    2220
aagcgctcag ttgacgggga gggttacaac gttgcccagt gtaacatgac caaagactgg    2280
ttcctggtac aaatgctagc taactacaac attggctacc agggcttcta tatcccagag    2340
agctacaagg accgcatgta ctccttcttt agaaacttcc agcccatgag ccgtcaggtg    2400
gtggatgata ctaaatacaa ggactaccaa caggtgggca tcctacacca acacaacaac    2460
tctggatttg ttggctacct tgcccccacc atgcgcgaag gacaggccta ccctgctaac    2520
ttcccctatc cgcttatagg caagaccgca gttgacagca ttacccagaa aaagtttctt    2580
tgcgatcgca cccttttggcg catcccattc tccagtaact ttatgtccat gggcgcactc    2640
acagacctgg gccaaaacct tctctacgcc aactccgccc acgcgctaga catgactttt    2700
gaggtggatc ccatggacga gcccaccctt ctttatgttt tgtttgaagt ctttgacgtg    2760
```

| gtccgtgtgc accggccgca ccgcggcgtc atcgaaaccg tgtacctgcg cacgcccttc | 2820 |
| tcggccggca acgccacaac ataa | 2844 |

<210> SEQ ID NO 6
<211> LENGTH: 984
<212> TYPE: DNA
<213> ORGANISM: Artificial
<220> FEATURE:
<223> OTHER INFORMATION: Ad5F11b chimeric Fiber

<400> SEQUENCE: 6

| atgaagcgcg caagaccgtc tgaagatacc ttcaaccccg tgtatccata tgacacggaa | 60 |
| accggtcctc caactgtgcc ttttcttact cctccctttg tatcccccaa tgggtttcaa | 120 |
| gagagtcccc ctggagttct tactttaaaa tgtttaaccc cactaacaac cacaggcgga | 180 |
| tctctacagc taaaagtggg aggggacttt acagtggatg acaccaacgg tttttttgaaa | 240 |
| gaaaacataa gtgccaccac accactcgtt aagactggtc actctatagg tttaccacta | 300 |
| ggagccggat tgggaacgaa tgaaaataaa ctttgtatca aattaggaca aggacttaca | 360 |
| ttcaattcaa acaacatttg cattgatgac aatattaaca ccttatggac aggagtcaac | 420 |
| cccaccgaag ccaactgtca aatcatgaac tccagtgaat ctaatgattg caaattaatt | 480 |
| ctaacactag ttaaaactgg agcactagtc actgcatttg tttatgttat aggagtatct | 540 |
| aacaatttta atatgctaac tacacacaga aatataaatt ttactgcaga gctgttttttc | 600 |
| gattctaact ggtaatttaa ctaactagac tctcatcccc tcaaaactcc acttaatcat | 660 |
| aaatcaggac aaaacatggc tactggtgcc attactaatg ctaaaggttt catgcccagc | 720 |
| acgactgcct atcctttcaa tgataattct agagaaaaag aaaactacat ttacggaact | 780 |
| tgttactaca cagctagtga tcgcactgct tttcccattg acatatctgt catgcttaac | 840 |
| cgaagagcaa taaatgacga gacatcatat tgtattcgta aacttggtc ctggaacaca | 900 |
| ggagatgccc cagaggtgca aacctctgct acaaccctag tcacctcccc atttacctttt | 960 |
| tactacatca gagaagacga ctaa | 984 |

<210> SEQ ID NO 7
<211> LENGTH: 861
<212> TYPE: DNA
<213> ORGANISM: Artificial
<220> FEATURE:
<223> OTHER INFORMATION: tumor-specific promoter

<400> SEQUENCE: 7

| taataggctg caggacttac tgttggtggg acgccctgct ttgcgaaggg aaaggaggag | 60 |
| tttgccctga gcacaggccc ccaccctcca ctgggctttc cccagctccc ttgtcttctt | 120 |
| atcacggtag tggcccagtc cctggcccct gactccagaa ggtggccctc ctggaaaccc | 180 |
| aggtcgtgca gtcaacgatg tactcgccgg gacagcgatg tctgctgcac tccatccctc | 240 |
| ccctgttcat ttgtccttca tgcccgtctg gagtagatgc ttttttgcaga ggtggcaccc | 300 |
| tgtaaagctc tcctgtctga cttttttttt tttttttagac tgagttttgc tcttgttgcc | 360 |
| taggctggag tgcaatggca caatctcagc tcactgcacc ctctgcctcc cgggttcaag | 420 |
| cgattctcct gcctcagcct cccgagtagt tgggattaca ggcatgcacc accacgccca | 480 |
| gctaattttt gtattttttag tagagacaag gtttcaccgt gatggccagg ctggtcttga | 540 |
| actccaggac tcaagtgatg ctcctgccta ggcctctcaa agtgttggga ttacaggcgt | 600 |
| gagccactgc acccggcctg cacgcgttct ttgaaagcag tcgagggggc gctaggtgtg | 660 |

```
ggcagggacg agctggcgcg gcgtcgctgg gtgcaccgcg accacgggca gagccacgcg    720
gcgggaggac tacaactccc ggcacacccc gcgccgcccc gcctctactc ccagaaggcc    780
gcggggggtg gaccgcctaa gagggcgtgc gctcccgaca tgccccgcgg cgcgccatta    840
accgccagat ttgaatcgcg g                                              861

<210> SEQ ID NO 8
<211> LENGTH: 986
<212> TYPE: DNA
<213> ORGANISM: Artificial
<220> FEATURE:
<223> OTHER INFORMATION: E1a expression cassette

<400> SEQUENCE: 8
atgagacata ttatctgcca cggaggtgtt attaccgaag aaatggccgc cagtcttttg     60
gaccagctga tcgaagaggt actggctgat aatcttccac ctcctagcca ttttgaacca   120
cctacccttc acgaactgta tgatttagac gtgacggccc ccgaagatcc caacgaggag   180
gcggtttcgc agattttttcc cgactctgta atgttggcgg tgcaggaagg gattgactta   240
ctcacttttc cgccggcgcc cggttctccg gagccgcctc acctttcccg gcagcccgag   300
cagccggagc agagagcctt gggtccggtt tctatgccaa accttgtacc ggaggtgatc   360
gatcttacct gccacgaggc tggctttcca cccagtgacg acgaggatga agagggtgag   420
gagtttgtgt tagattatgt ggagcacccc gggcacggtt gcaggtcttg tcattatcac   480
cggaggaata cggggggaccc agatattatg tgttcgcttt gctatatgag gacctgtggc   540
atgtttgtct acagtaagtg aaaattatgg gcagtgggtg atagagtggt gggtttggtg   600
tggtaatttt ttttttaatt tttacagttt tgtggtttaa agaattttgt attgtgattt   660
ttttaaaagg tcctgtgtct gaacctgagc ctgagcccga gccagaaccg gagcctgcaa   720
gacctacccg ccgtcctaaa atggcgcctg ctatcctgag acgcccgaca tcacctgtgt   780
ctagagaatg caatagtagt acggatagct gtgactccgg tccttctaac acacctcctg   840
agatacaccc ggtggtcccg ctgtgcccca ttaaaccagt tgccgtgaga gttggtgggc   900
gtcgccaggc tgtggaatgt atcgaggact tgcttaacga gcctgggcaa cctttggact   960
tgagctgtaa acgccccagg ccataa                                        986
```

FAST AND ACCURATE THREE-PLASMID ONCOLYTIC ADENOVIRUS RECOMBINANT PACKAGING SYSTEM Ad5MixPlus AND APPLICATION THEREOF

RELATED APPLICATION DATA

This application is a National Stage Application under 35 U.S.C. 371 of co-pending PCT application number PCT/CN2020/070125 designating the United States and filed Jan. 2, 2020; which claims the benefit of CN application No. 201910549429.9 and filed Jun. 24, 2019 each of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Nov. 19, 2021, is named 007874.00015_ST25.txt and is 122,544 bytes in size.

TECHNICAL FIELD OF THE INVENTION

The present invention refers to the field of biomedical technology, particularly to a fast and accurate three-plasmid oncolytic adenovirus recombinant packaging system Ad5MixPlus and application thereof.

BACKGROUND OF THE INVENTION

Malignant tumor has become a major disease affecting all human life. In 2000, there were about 10 million new tumor cases and 6.2 million deaths worldwide. By 2018, the number of new cancer cases worldwide had increased to 18.1 million, and the number of deaths had increased to 9.6 million (CA cancer J Clin. 2018 November; 68:394-424). In 2000, there were about 1.8-2 million tumor cases and 1.4-1.5 million tumor deaths in China, but by 2014, the number of new cases was 3.804 million and the number of deaths was 2.296 million, making tumor the leading cause of death (Chin J Cancer Res. 2018 February; 30:1-12). At present, in addition to conventional surgery, radiotherapy, and chemotherapy for malignant tumors, the tumor immunotherapy developed in recent years has made rapid progress, especially immune checkpoint therapy such as PD-1/PD-L1 antibody and immunocyte therapy, such as CAR-T, and has become an indispensable part of comprehensive treatment following radiotherapy, chemotherapy, and surgery. Immunotherapy represented by CAR-T cells and PD-1/PD-L1 antibodies has been used in clinical practice, showing strong curative effect and great market value (Nat Biotechnol. 2018 October; 36:847-856; Cell. 2018 Oct. 4; 175:313-326). In August 2017, Novartis's CAR-T product Kymriah for the treatment of B-cell acute lymphoblastic leukemia was approved by FDA for marketing, with a price of US$475,000. Two months later, Kite's CAR-T drug Yescarta for the treatment of large B-cell lymphoma was approved by FDA for marketing, with a price of US$373,000. Recently, scientists have discovered that a variety of oncolytic virus products that can be used as CAR-T cells and PD-1/PD-L1 antibody immunotherapy synergists can not only enhance the effect of radiotherapy and chemotherapy, but also improve the therapeutic effect of antibodies and immune cells. At the same time, tumor cells infected by these oncolytic viruses release a large amount of cytokines, and the lysed tumor cells release a large amount of tumor-associated antigens which have immune activation effects. Therefore, the combined use of oncolytic virus products with CAR-T cells or PD-1/PD-L1 antibodies is conducive to the amplification of immunotherapy effects, and the application scope of oncolytic virus products can be widened.

Oncolytic virus (OV) is a type of virus that has been artificially genetically modified, which can specifically replicate in tumor cells in large quantities without affecting normal cells. Tumor cells containing a large amount of virus are lysed and destroyed, and virus particles are released to continue to infect and destroy more tumor cells. The oncolytic virus is used as a vector to carry antitumor genes. As the virus replicates and spreads, the number of copies of the antitumor genes it carries increases, which further increases the expression amount of protein products. Therefore, the anti-cancer effect is enhanced under the synergistic effects by the anti-cancer effect of the antitumor genes and the oncolytic effect of oncolytic virus. Oncolytic virus therapy has broader indications than CAR-T and has a lower cost than monoclonal antibody drugs. Due to the high efficiency of killing tumor cells, good targeting, high safety, low side effects and low cost, oncolytic virus-mediated gene therapy for tumors has become an important new tumor treatment method following the three conventional treatment methods (surgery, radiotherapy and chemotherapy) and immunotherapy, and may become an important auxiliary method to assist comprehensive treatment of tumors to improve curative effect. In September 2017, the top medical journal "Cell" reported a breakthrough study. In this study, the efficacy of oncolytic virus therapy combined with PD-1 monoclonal antibody immunotherapy was studied in a phase Ib clinical trial of 21 melanoma patients by researchers from the U.S., Switzerland, Spain, and Australia. The results suggest that the efficacy of immunotherapy is effectively improved by oncolytic viruses with an overall response rate of up to 62%, and combination therapy is significantly better than single treatment, which proved that oncolytic virus has a very bright future as one of the methods of comprehensive tumor treatment (Cell. 2017 Sep. 7; 170:1109-1119.e10). The milestone of the oncolytic virus is that Amgen's oncolytic virus Talimogene laherparepvec (T-Vec) was approved for marketing in the United States and the European Union in 2015. T-Vec, expressing granulocyte-macrophage colony stimulating factor (GM-CSF), can be directly injected into tumors, and replicate in tumor cells until cell lysis (oncolysis) occurs. Then, GM-CSF is released to the tumor tissue to activate the systemic immune response. In general, T-Vec works in two important and synergistic ways by inducing tumor cell lysis and stimulating the systemic anti-tumor immune response (Lancet Oncol. 2016 November; 17:1485-1486). Thomson Reuters estimates that T-Vec sales for melanoma treatment will be $388 million/year by 2020.

OV has always been a hot spot in the research and development of antitumor drugs, as well as the capital market and pharmaceutical groups. At the beginning of 2018, MSD and Viralytics announced that MSD acquired Viralytics at a price of $394 million which is equivalent to a 160% premium of the weighted average price of Viralytics stock in one month. MSD acquired all rights about the oncolytic virus immunotherapy product CAVATAK® (CVA21) developed by Viralytics through the acquisition. CAVATAK®, a preparation based on Viralytics' proprietary oncolytic virus Coxsackievirus Type A21, has been proven to infect and kill cancer cells preferentially. CAVATAK® is currently in multiple phase I and phase II clinical trials as an intra-tumor intravenous injection. Taking into account MSD's ongoing PD-1 drug KEYTRUDA® trial, CAV- ATAK® may be used in the next step with PD-1 drug KEYTRUDA® for the treatment of melanoma, prostate cancer, lung cancer and bladder cancer. The OV drug T-Vec, developed by BioVex and acquired by biotech giant Amgen at a price of $425 million in 2011, was approved by the FDA for marketing in 2015 and obtained EU CHMP approval in December of the same year, becoming a milestone in OV treatment for tumors. At present, T-Vec has been widely used in the United States, Europe and Australia to treat relapsed melanoma at an average cost of $65,000. Thomson Reuters estimates that T-Vec's sales will be $388 million per year by 2020. The OV products that have entered phase III clinical include Oncolytics' Reolysin for the treatment of head and neck tumors, ColdGenesys's CG0070 for the treatment of bladder cancer, Advantagene's Prost Atak™ for the treatment of prostate cancer, and Jennerex's PexaVec for the treatment of liver cancer. OV is a broad-spectrum anti-tumor drug. The tumors treated by OV currently entering clinical trials include melanoma, head and neck cancer, prostate cancer, bladder cancer, glioblastoma, liver cancer, breast cancer, non-small cell lung cancer, colon cancer, ovarian cancer, etc., among them, the first six types of tumors will be the most important on the market in recent years. According to Beijing OLXOZ Information Consulting Co., Ltd., the upcoming OV products for head and neck cancer, prostate cancer, bladder cancer, glioma and liver cancer will have annual sales of 1.17, 7.15, 2.925, 2.275, and 4.864 billion U.S. dollars, respectively. The greater value of OV is to be used in combination with radiotherapy or chemotherapy. Oncolytics' Reolysin combined with paclitaxel or carboplatin in the treatment of advanced head and neck cancer has a response rate of 42%, while chemotherapy alone is only 3%-10%. Therefore, the OV market space is even greater if it is combined with other drugs.

China has also made a lot of achievements in the field of OV drugs. OV research and development has been supported by the major special fund for new drug creation of the Ministry of Science and Technology for many consecutive years. In 2005, the oncolytic adenovirus "H101" (trade name: Oncorine) developed by Shanghai Sunway Biotechnology Co., Ltd. was first approved by China Food and Drug Administration (CFDA) as a first-class new drug and became the world's first OV drug to be marketed. At the end of 2016, reaching an agreement with Japan's Oncolys Bio-Pharma, China's Hengrui pharmaceutical company obtained an exclusive license for $102 million to develop, produce and commercialize Oncolys' oncolytic adenovirus product Telomelysin™ (OBP-301) in mainland China, Hong Kong and Macao.

OV was developed to solve the shortcomings of low expression of anti-cancer genes and the inability of the vector to target tumor cells in gene therapy. Cancer gene therapy mediated by oncolytic viruses can target tumor cells, produce oncolytic effects, and produce synergistic anti-cancer effects with gene therapy, which has obvious application value. In theory, many types of viruses can be transformed into oncolytic viruses. For example, T-Vec is transformed from herpes simplex virus, ProstAtak and G0070 are transformed from adenovirus, Reolysin is transformed from reovirus, and JX-594 is transformed from the vaccinia virus. Among them, adenovirus is the most extensively studied type, and the types of oncolytic viruses transformed from adenoviruses are also the most. There are many types of adenoviruses and their structures are complex. At present, more than 100 serotypes of adenoviruses have been found. Their genomes are linear double-stranded DNA molecules, about 35-36 kb. Compared with other types of viruses, adenovirus has the following advantages: it can infect almost all types of cells and can replicate in large numbers in host cells; the viral genome does not integrate into the host cell chromosome, and there is no risk of insertional mutagenicity; the titer is high so it is easy to prepare and purify, etc. Adenovirus is most suitable for developing safe OV products. However, the use of adenovirus as an oncolytic virus also has some disadvantages: such as strong autoimmunity, poor specificity, and easy accumulation in the liver by intravenous injection, so it needs to be further modified. These complex characteristics of adenovirus provide us the best opportunity for targeted and effective modification, which is more conducive to the development of a multi-mechanism synergistic anti-cancer efficient oncolytic adenovirus (OAV) product through a comprehensive modification, and the design and construction of personalized OAV suitable for different tumor types. The main purpose of the modification of adenovirus is to improve the specificity of targeting, the efficiency of infection, the expression of loaded anti-cancer genes, and to avoid the elimination of the virus by the body's immune system (Mol Cancer Ther. 2016 July; 15:1436-51).

The construction of OAV based on the least virulent human adenovirus C subgenus type 5 (Ad5) mainly includes the modification of the E1 region of the left arm of the genome and the modification of the capsid protein, fiber protein, and E3 region of the right arm of the genome.

1. Modification of Left Arm Functional Region of Adenovirus Genome

To construct OAV, it is necessary to retain the expression of E1a protein and make it regulated by tumor-specific promoters, so that the virus can specifically replicate in the tumor. E1a has 3 functional areas, CR1, CR2, and CR3. The CR1 region inhibits the expression of Her-2/neu gene by binding to the transcription regulator P300/CBP, the CR2 region binds to the Rb protein family, and the CR3 region is the transcription activation region. Therefore, E1a protein can not only inhibit the transcription of Her-2/neu gene, block the activity of NF-κB, increase the expression of p53, but also inhibit the expression of protease genes such as type IV collagenase and plasminogen activator, thereby exerting resistance tumor effect. E1a can also cause non-specific immune responses, improve the killing effect of CTL cells, NK cells, and macrophages, induce tumor cell apoptosis, inhibit tumor invasion and metastasis, and improve tumor cell sensitivity to chemotherapy and radiotherapy. The introduction of deletion mutations in the CR2 region of E1a can prevent E1a from binding to the Rb protein, ensuring that the dephosphorylated Rb protein forms a complex with the transcription factor E2F to block the transcriptional activity of E2F and ultimately enhances the anti-cancer activity. There are still many questions that need to be studied in depth, such as how to modify E1a to make it have anti-cancer activity, and what are the molecular mechanisms and signaling pathways involved in E1a. In addition, a large number of cytokines released when OAV infects cancer cells and a large number of tumor-associated antigens released when OAV lyses cancer cells can play an immune activation effect. Therefore, the greatest application value of OAV is its combined application with immunotherapy.

The E1b transcription unit encodes E1b-55 kDa and E1b-19 kDa. E1b-55 kDa is a protein necessary for adenovirus replication in normal cells but not necessary in tumor cells. The selective deletion of the E1b-55 kDa coding gene can enable adenovirus to maintain the ability of replication in tumor cells, and lost the ability to replicate in normal cells. Because the E1b-55 kDa protein can inactivate and degrade the P53 protein, the E1b-55 kDa deletion helps cells maintain the anti-tumor activity of P53. The E1b-19 kDa gene is homologous to the apoptosis-inhibiting gene Bcl-2. The E1b-19 kDa protein can bind to Bax or/and Bak to initiate the downstream apoptosis-inhibiting program and protect infected cells from TNF-α-mediated killing. The deletion of E1b-19 kDa increases the specificity of the virus mutant's replication in tumor cells, while the replication activity in normal cells is weakened. The deletion of E1b-19 kDa can promote the recovery of apoptosis pathway in cancer cells, and is conducive to the rapid elimination of viruses in normal cells and the rapid release and dissemination of viruses in tumor cells, so that OAV has better specificity and stronger efficacy. However, whether the double deletion of E1b-55 kDa and E1b-19 kDa affects the replication of OAV, and whether the modification of the two can produce immune enhancement effect needs further study.

2. Modification of the Right Arm Functional Region of Adenovirus Genome

The E3 transcription unit on the right arm of the adenovirus genome has 9 open reading frames, which encode proteins that protect infected cells from the host's immune response. E3-gp19k can attenuate the killing effect of CTL-mediated infected cells. RID can block apoptosis mediated by "death" ligands including TNF, Fas ligand and TRAIL. RID can also inhibit the activation of NF-κB necessary for cell survival mediated by IL-1 and TNF. In addition to down-regulating the TRAIL receptor, E3-6.7k can individually inhibit cell apoptosis induced by external and internal signaling pathways. E3-14.7k is a broad inhibitor of TNF-mediated apoptosis. It can also bind to and inhibit Caspases-8 to prevent apoptosis initiated by the Fas signaling pathway. E3-14.7k interacts with FIP protein (for 14.7K-interacting protein, FIP-1, -2, -3) in infected cells, making E3-14.7k protein play an important role in signal transduction pathways such as apoptosis and survival, inflammatory response, maintaining membrane stability, and nuclear and plasma transport. The molecular mechanism of this multi-functional E3 protein still needs to be studied in depth. Adenovirus death protein (ADP) can promote cell lysis and virus release, but the molecular mechanism is unknown. It can be seen that the deletion of the E3 region during the OAV construction process can not only expand the vector capacity, but also promote the apoptosis of infected cancer cells. The immune resistance of the virus to the body is also relieved by the loss of E3, and the virus can be quickly eliminated. Therefore, increasing the understanding of the function of the protein encoded by the E3 region and avoiding deleting all the E3 regions blindly in the construction of OAV may be more conducive to the long-term expression of the target gene.

The human adenovirus family has 52 serotypes, divided into 6 subgenres (A to F). Except for group B, all subgenres of adenoviruses use coxsackievirus-adenovirus receptor (CAR) as their main recognition receptor, and the infection efficiency for CAR-deficient cells such as hematopoietic cells, hematopoietic stem cells, dendritic cells, some tumor cells, especially tumor stem cells is very low. Adenoviruses subgenres B (Ad3, Ad11b, Ad14, Ad16, Ad21, Ad35, Ad50) mainly recognize CD46, a widely expressed complement regulatory protein. Using fiber knob of adenoviruses subgenres B instead of fiber knob of Ad5 to construct a chimeric virus will help improve the infection efficiency of the virus to tumor cells, especially the ability to infect tumor stem cells, and may more completely prevent tumor recurrence. Ad5 exists widely in nature, and most people have been infected and have produced neutralizing antibodies that can block the virus. Ad5 is hepatotropic and can be adsorbed by hepatocytes. The hypervariable region (HVR) of the adenovirus capsid protein Hexon is exposed to the surface of the adenovirus, which is the key part that causes the difference in liver infection ability and immunogenicity between different serotypes of adenovirus. An effective way to help Ad5 avoid pre-existing immunity and liver uptake is to selectively chimerize the 7 HVRs in the Hexon molecule of Ad5 with the corresponding regions of Hexon of rare serotypes such as subgenres D (Ad37, Ad43) and subgenres B (Ad48). However, modification of Hexon, the main structural protein of adenovirus, often results in structural instability of the adenovirus vector, which makes it impossible to effectively package the virus. Therefore, this is a very challenging study.

3. Technology for Recombination and Packaging of Adenovirus

At present, the most commonly used system for packaging adenoviruses is from Microbix Biosystems. The adenovirus left arm plasmid pDC series (such as pDC315, pDC316, pDC312, etc.) and the left arm backbone plasmid (pBHGloxdelE13cre) with complete deletion of E1/E3 region are recombined. This technology has been used on the market for nearly 20 years, and is still in use now. The produced virus lacks all the E3 area. Both E1a gene for specific replication in tumor and exogenous antitumor genes must be carried by pDC plasmids before they are further recombined into the adenovirus E1 region. As a result, the size of the inserted fragment in the left arm is limited, and since the E1a promoter and the anti-cancer gene promoter are both in the E1 region, they are too close to each other and interfere with each other, the expression efficiency of them are all reduced. We tried to separate them with insulator sequences in the early stage. Although there are improvements, the effect is not obvious. There have been attempts to insert exogenous anti-cancer genes into the E3 region. The expression efficiency of exogenous genes is ideal, but the right arm plasmid is large, taking pBHGloxdelE13cre as an example, the size is 34.707 kb. The transformation of a large vector is difficult, and the success rate is not high. It often requires repeated attempts to screen the correct vector.

When a new type of OAV is constructed, in order to improve the targeting efficiency of tumor cells, the transfection rate, the expression of the loaded anti-cancer genes, and to avoid the elimination of the virus by the body's immune system, the right arm backbone plasmid needs to be greatly modified, including screening Fiber molecules that can enhance the efficiency of adenovirus infection, Hexon molecules that can make the virus evade the body's immune interception and liver uptake, and a variety of exogenous genes with different mechanisms and functions, and inserting the expression sequence of the above molecules into the E3 region. For the screening and modification of each molecule, the large right arm backbone vector must be reconstructed, and the genome spanning from Hexon and E3 region to Fiber is up to 14 kb, therefore, the modification is a lot of work, difficult, time-consuming and labor-intensive. For example, replacing the original Hexon gene with a chimeric Hexon gene to construct an adenovirus backbone plasmid vector containing chimeric Hexon with hypervariable region, reported by a doctoral dissertation titled "Fiber-modified Hexon-chimeric Oncolytic Adenoviral Vectors Targeting Gastric Cancer-Associated Fibroblasts" published in 2013, has the disadvantage of large workload mentioned above. In order to solve the technical difficulties of OAV construction and packaging, we have developed a fast and accurate three-plasmid oncolytic adenovirus recombinant system Ad5MixPlus, which has been confirmed in practical applications. The ideal new OAV product can be packaged accurately and quickly, saving time and effort.

SUMMARY OF THE INVENTION

Adenovirus has to be modified on a large scale, involving almost the whole genome, mainly to improve the specificity of targeting tumor cells, and the transfection rate, increase the expression level of loaded anti-cancer genes, and avoid the elimination of the virus by the body's immune system. In the past, the modification and recombination of OAV were mostly concentrated in the E1 region of the left arm of the adenovirus genome. Exogenous anti-cancer genes were also inserted in the E1 region. Since the E1a promoter and the anti-cancer gene promoter are both in the E1 region, they are too close to each other and interfere with each other, the expression efficiency of them are all reduced. If you want to further optimize and increase the transfection rate of OAV, the expression level of loaded anti-cancer genes, and avoid the elimination of the virus by the body's immune system, it is necessary to screen useful molecules from different serotypes of adenovirus to construct Fiber chimeric and Hexon chimeric hybrid OAV, and variety of anti-cancer genes to load them into the E3 region of OAV according to tumor type and treatment needs. Therefore, the structural proteins of the adenovirus right arm backbone plasmid, including Hexon, Fiber, E3 region, etc., need to be modified in a wide range. But the right arm plasmid is very large. Take the most commonly used Microbix Biosystems right arm backbone plasmid pBHGloxdelE13cre as an example, the size is 34.707 kb. Thus, a large vector construction is required for each modification of each protein molecule. Because the modification of large vectors is difficult, the error rate is high, and the selection is difficult, the modification of OVA is time-consuming, laborious and costly, and screening the correct vector often requires repeated attempts.

In order to solve the above technical problems, the present invention provides a fast and accurate three-plasmid oncolytic adenovirus recombinant packaging system, which involving the following 3 adenovirus recombinant plasmids:
  a) adenovirus right arm backbone plasmid: the said adenovirus right arm backbone plasmid is loaded with two sets of recombinant sequences at different sites, one set of attL/attR in the Fiber/Hexon/E3 region, and the other set of Cre/loxP in the E1 region; the E3 region is also inserted the ccdB lethal gene of DB3.1 *E. coli* strain and competent cells;
  b) adenovirus right arm shuttle plasmid: the said adenovirus right arm shuttle plasmid contains the reconstructed chimeric Hexon sequence and chimeric Fiber sequence; the E3 region is preset with multiple cloning sites for exogenous gene insertion; Hexon/E3/Fiber sequence contains attL1/attL2 recombination sites at both ends;
  c) adenovirus left arm shuttle plasmid: the said adenovirus left arm shuttle plasmid is inserted tumor-specific promoter-controlled adenovirus early replication gene and loxP recombination site at its multiple cloning sites;
  wherein, the first round of attL/attR site-specific recombination is performed between the adenovirus right arm shuttle plasmid and the adenovirus right arm backbone plasmid based on attL1/attL2 at both ends of the Hexon/E3/Fiber sequence, resulting that the sequence between attL1/attL2 in the adenovirus right arm shuttle plasmid replaces the sequence between attR1/attR2 in the adenovirus right arm backbone plasmid; the second round of Cre/loxP site-specific recombination is performed between the adenovirus left arm shuttle plasmid and the adenovirus right arm backbone plasmid, resulting that the E1a expression cassette controlled by the tumor-specific promoter in the adenovirus left arm shuttle plasmid is inserted into the E1 region of the adenovirus right arm backbone plasmid; the required oncolytic adenovirus is packaged after the above two rounds of site-specific recombination.

As a preferred example of the present invention, the chimeric Hexon sequence is a chimeric sequence formed by Hexon of Ad5 and Hexon or its mutant sequence of Ad48, Ad9, Ad37, Ad43 or any other serotype adenovirus.

As another preferred example of the present invention, the sequence of the said chimeric Hexon is SEQ ID NO: 5.

As another preferred example of the present invention, the chimeric Fiber sequence is a chimeric sequence formed by Fiber of Ad5 and Fiber or its mutant sequence of Ad11b, Ad3, Ad14, Ad16, Ad21, Ad35, Ad50, Ad55 or any other serotype adenovirus.

As another preferred example of the present invention, the sequence of the said chimeric Fiber is SEQ ID NO: 6.

As another preferred example of the present invention, the tumor-specific promoter is selected from: (a) promoter, enhancer and mutant sequence of carcinoembryonic antigen; (b) promoter, enhancer and mutant sequence of alpha fetoprotein; (c) promoters, enhancers and mutant sequences of receptor tyrosine kinases (including EGFR, Her-2, Her-3 and Her-4) of the human epidermal growth factor receptor family (EGFRs); (d) promoter, enhancer and mutant sequence of breast cancer related antigen DF3/MUC1; (e) promoter, enhancer and mutant sequence of vascular endothelial growth factor (VEGF) receptor KDR; (f) promoter, enhancer and mutant sequence of L-plastin; (g) promoters, enhancers and mutant sequences of members of the inhibitor of apoptosis protein family (IAP); (h) promoters, enhancers and mutant sequences of prostaglandin-specific antigens; (i) conserved sequences of hypoxia response elements regulated by hypoxia inducible factor-1 (HIF-1); (j) promoter, enhancer and mutant sequence of transcription factor E2F; (k) promoter, enhancer and mutant sequence of hTERT.

As another preferred example of the present invention, the sequence of the said tumor-specific promoter is SEQ ID NO:7.

As another preferred example of the present invention, the said adenovirus early replication gene is E1a or E1b, wherein E1a is wild or mutant, and the E1b is E1b-55 kDa, E1b-19 kDa or mutants thereof.

As another preferred example of the present invention, the sequence of the said E1a expression cassette is SEQ ID NO:8.

As another preferred example of the present invention, the sequence of the said adenovirus right arm backbone plasmid is SEQ ID NO: 1, the sequence of the said adenovirus right arm shuttle plasmid is SEQ ID NO: 2, and the sequence of the said adenovirus left arm shuttle plasmid is SEQ ID NO:3.

As another preferred example of the present invention, the sequence of the oncolytic adenovirus is SEQ ID NO: 4.

The present invention also provides the application of the three-plasmid oncolytic adenovirus recombinant packaging system in the preparation of oncolytic adenovirus or antitumor drugs.

As a preferred example of the present invention, the tumor is selected from a digestive system tumor such as esophageal cancer, gastric cancer, colorectal cancer, liver cancer, pancreatic cancer, bile duct and gallbladder cancer; respiratory system tumor such as lung cancer and pleuromas; blood system tumor such as leukemia, lymphoma and multiple myeloma; gynecological and reproductive system tumor such as breast cancer, ovarian cancer, cervical cancer, vulvar cancer, testicular cancer, prostate cancer and penile cancer; nervous system tumor such as glioma, neuroblastoma and meningioma; head and neck tumor such as oral cancer, tongue cancer, laryngeal cancer and nasopharyngeal cancer; urinary system tumor such as kidney cancer and bladder cancer, and skin and other system tumor such as skin cancer, melanoma, osteosarcoma, liposarcoma and thyroid cancer.

The advantages of the present invention are listed as follows:

This invention provides a fast and accurate three-plasmid oncolytic adenovirus recombinant packaging system Ad5MixPlus consisting of 3 adenovirus recombinant plasmids and the application thereof. The core technology of the present invention is to cleverly load two sets of different sites for recombination on the first adenovirus recombinant plasmid, type 5 adenovirus right arm backbone plasmid pAd5MixPlus, one set of attL/attR in the Fiber/Hexon/E3 region, the other set of Cre/loxP in the E1 area. The second adenovirus recombinant plasmid, adenovirus right arm shuttle plasmid pAdH548F511LR, contains the modified Fiber/Hexon/E3 sequence, and the E3 region is preset with multiple cloning sites for exogenous gene insertion. Basing on attL1/attL2 at both ends of the Hexon/E3/Fiber sequence, the adenovirus right arm shuttle plasmid undergoes the first round of specific recombination at attL/attR site with adenovirus right arm backbone plasmid pAd5MixPlus in bacteria, and the sequence between attR1/attR2 in pAd5MixPlus is replaced by the sequence between attL1/attL2 in pAdH548F511LR. Then the bacteria carrying the recombinant plasmid are accurately screened with the help of ccdB gene in the E3 region of pAd5MixPlus. The third adenovirus recombinant plasmid, the adenovirus left arm shuttle plasmid pAdSVPcreLoxP, contains an E1a expression cassette controlled by a tumor-specific promoter and a loxP recombination site. The adenovirus left arm shuttle plasmid undergoes the second round of specific recombination at Cre/loxP site with pAd5MixPlus in eukaryotic cells, and the E1a expression cassette controlled by the tumor-specific promoter in pAdSVPcreLoxP is inserted into the E1 region of pAd5MixPlus. Finally, the ideal oncolytic adenovirus is packaged accurately and quickly after the above two rounds of site-specific recombination. All sequence modifications are carried out on two small shuttle plasmids. The modification of the E1 region for tumor-specific replication of virus is carried out on the said adenovirus left arm shuttle plasmid, while the modification of the protein structure of the virus Hexon, Fiber, E3 region and the insertion of exogenous genes in the E3 region are all carried out on the said adenovirus right arm shuttle plasmid. Therefore, the difficulty of modification of the large adenovirus backbone plasmid vector is solved. The exogenous gene can be loaded into any shuttle plasmid to be inserted into the E1 or E3 region of the oncolytic adenovirus genome according to actual needs. Basing on our Ad5MixPlus recombination system, the viral recombination and packaging process is simplified, fast and accurate, which solves the challenging problem of the large adenovirus backbone plasmid vector modification. The required oncolytic adenovirus can be quickly recombined and screened, which is very suitable for industrialization needs.

Further experiments showed that the oncolytic adenovirus packaged in the present invention had strong specific replication activity in tumor cells, strong killing activity on tumor cells, and significantly inhibited the increase of tumor volume.

DETAILED DESCRIPTION OF THE PREFERRED EMBODIMENT

The specific embodiments of the present invention are described in detail with reference to drawings.

Example 1 Fast and Accurate Three-Plasmid Oncolytic Adenovirus Recombinant Packaging System Ad5MixPlus of the Present Invention The fast and accurate three-plasmid oncolytic adenovirus recombinant packaging system of the present invention involves 3 adenovirus recombinant plasmids, adenovirus right arm backbone plasmid of Ad5MixPlus system, adenovirus right arm shuttle plasmid of Ad5MixPlus system, and adenovirus left arm shuttle plasmid of Ad5MixPlus system. The recombination and packaging process of these 3 adenovirus recombinant plasmids and Ad5MixPlus is as follows.

1. Adenovirus Right Arm Backbone Plasmid of Ad5MixPlus System

Figure 1:
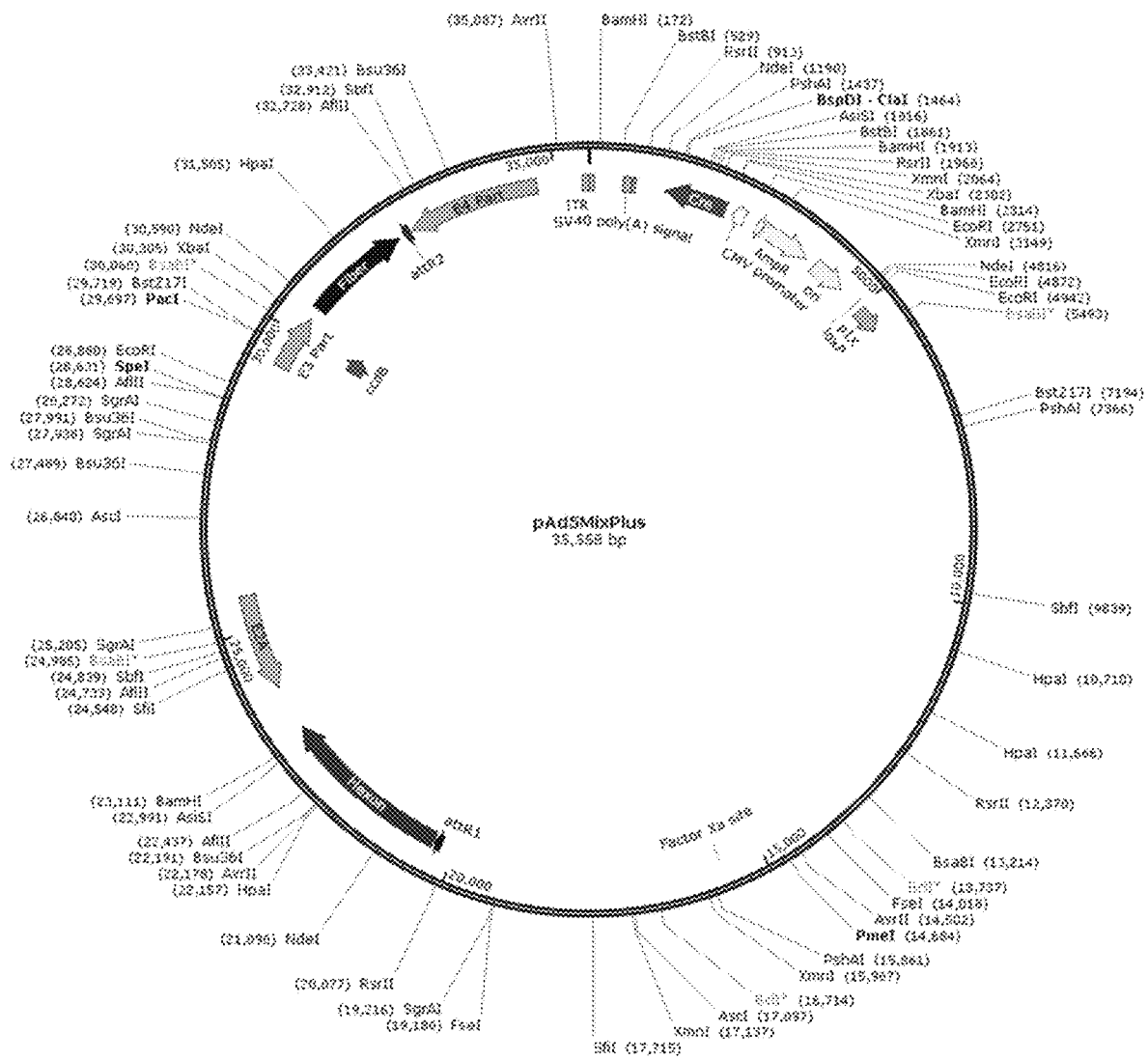
FIG. 1 shows the structure of the adenovirus right arm backbone plasmid pAd5MixPlus.

The first adenovirus recombinant plasmid, adenovirus right arm backbone plasmid pAd5MixPlus, was constructed based on adenovirus type 5 and was loaded with two sets of recombinant sites, one attL/attR in Fiber/Hexon/E3 region and the other Cre/loxP in E1 region (FIG. 1). The ccdB lethal gene that causes the death of the DB3.1 *E. coli* strain and competent cells was inserted in the E3 region to screen successful recombinant clones. The principle is that the successful recombinant vector lost the ccdB lethal gene between attR1 and attR2 sites, and there was no ccdB lethal gene expression, so the competent bacteria survived and formed clones, while the unsuccessful recombinant vector expressed the original ccdB gene and resulted in bacterial death.

The full-length sequence of adenovirus right arm backbone plasmid pAd5MixPlus is SEQ ID NO: 1.

2. Adenovirus Right Arm Shuttle Plasmid of Ad5MixPlus System

Figure 2:
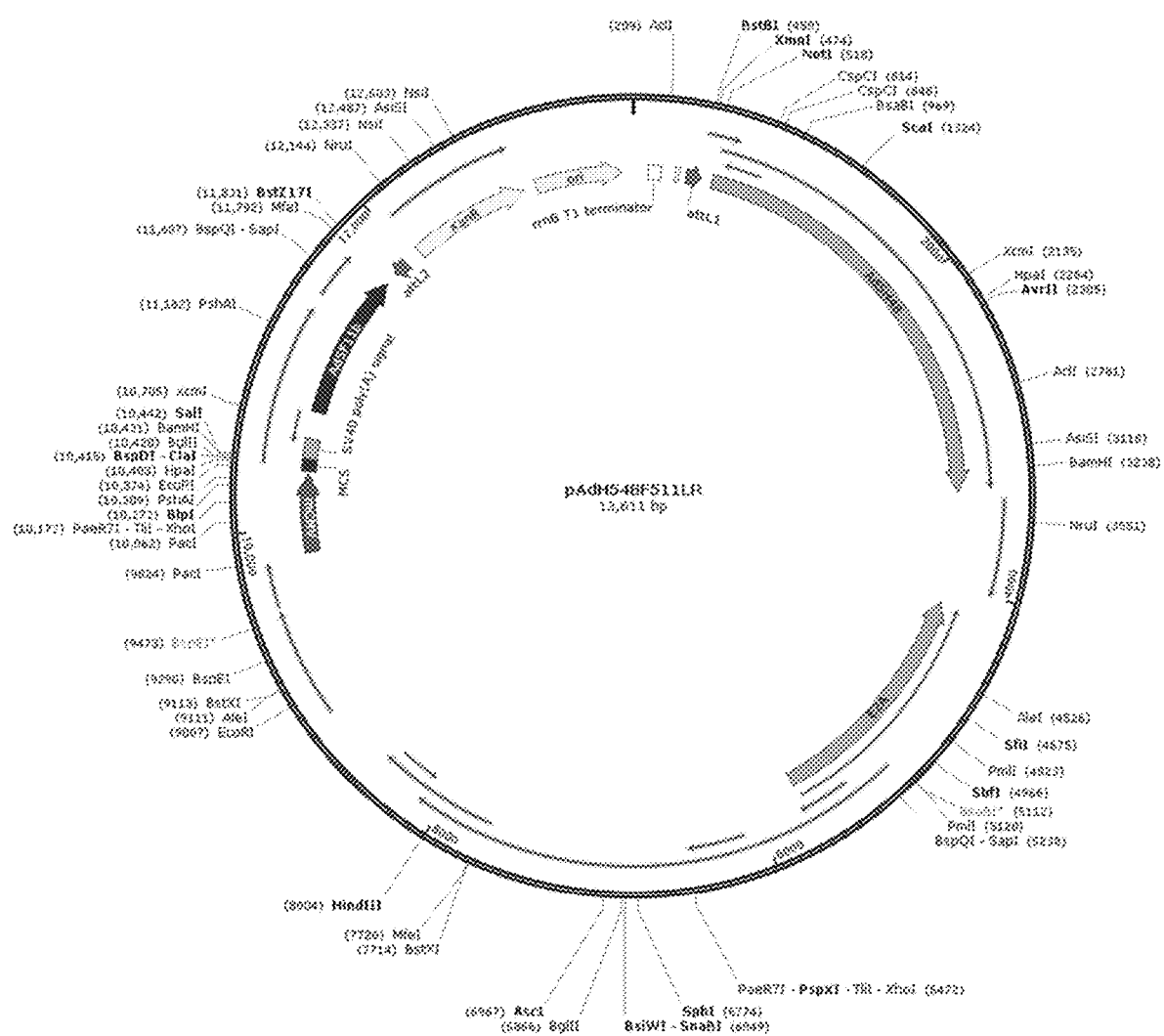
FIG. 2 shows the structure of the adenovirus right arm shuttle plasmid pAdH548F511LR.

The second adenovirus recombinant plasmid, adenovirus right arm shuttle plasmid pAdH548F511LR, contains the modified Ad5H48 chimeric Hexon sequence and Ad5F11b chimeric Fiber sequence. Multiple cloning sites for exogenous genes insertion were preset in the E3 region. Hexon/E3/Fiber sequence contains attL1/attL2 recombination sites at both ends (FIG. 2).

The full-length sequence of adenovirus right arm shuttle plasmid pAdH548F511LR is SEQ ID NO: 2.

3. Adenovirus Left Arm Shuttle Plasmid of Ad5MixPlus System

Figure 3:
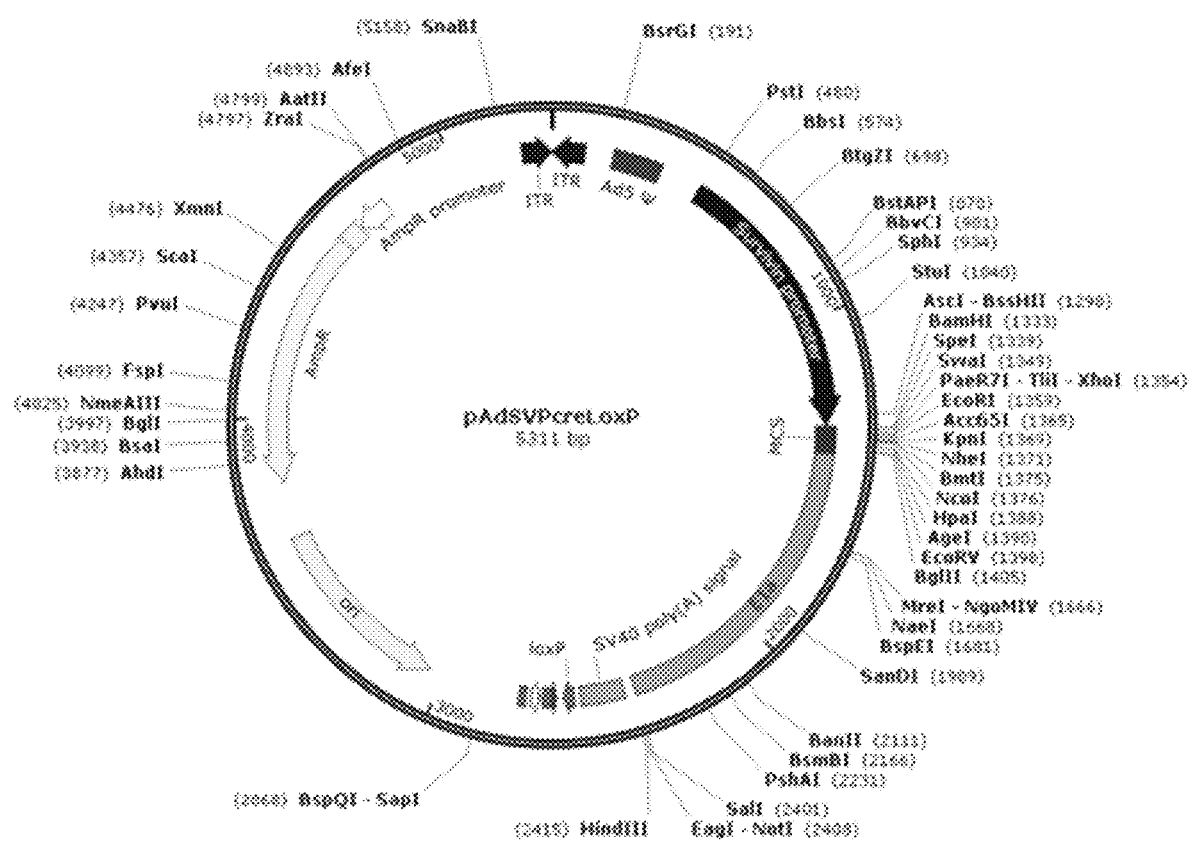
FIG. 3 shows the structure of the adenovirus left arm shuttle plasmid pAdSVPcreLoxP.

The third adenovirus recombinant plasmid, adenovirus left arm shuttle plasmid pAdSVPcreLoxP, contains an E1a expression cassette controlled by tumor-specific promoter Survivin and a loxP recombination site (FIG. 3).

4. Recombinant Packaging Procedure for Ad5MixPlus System

Figure 4:
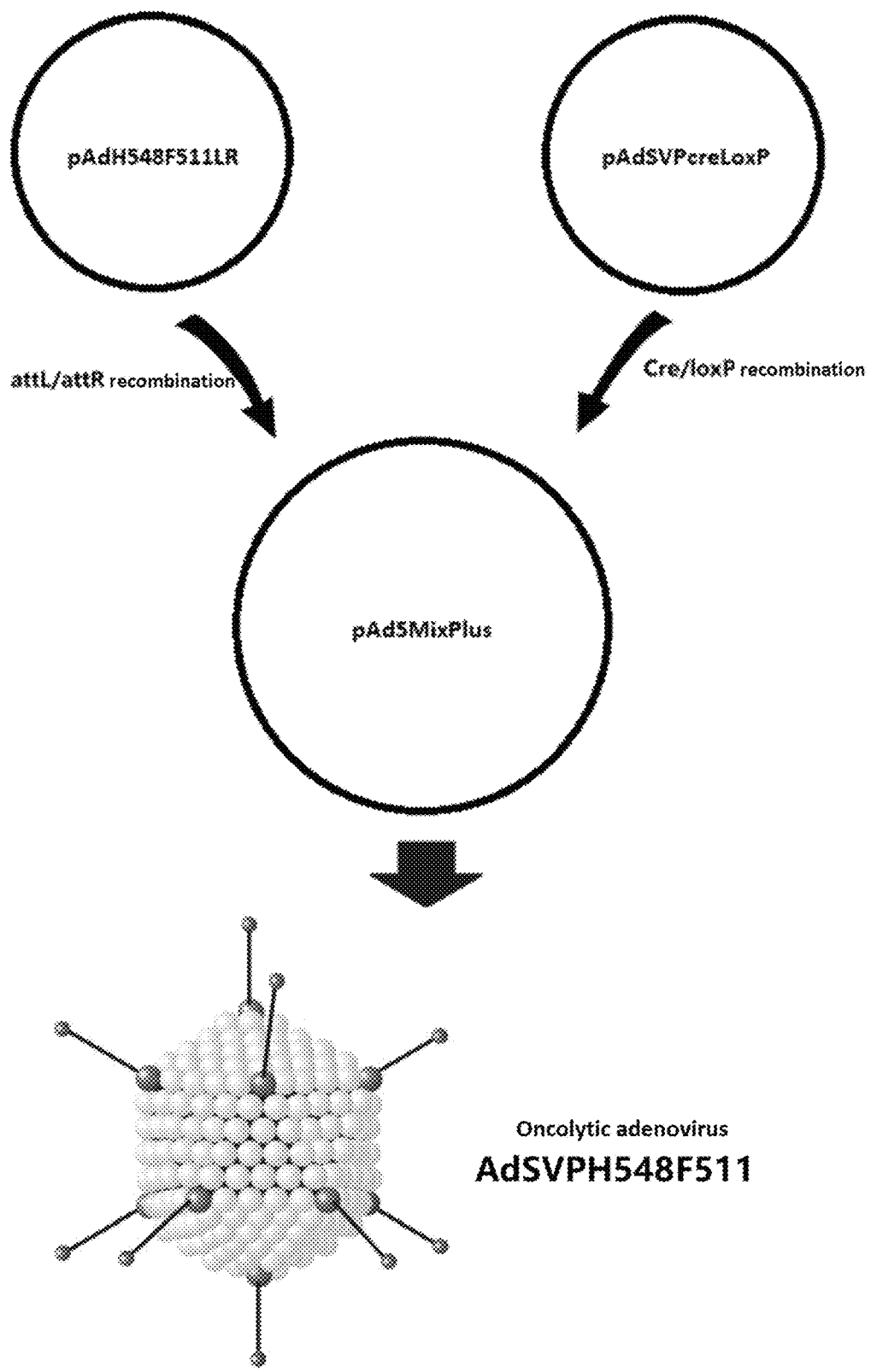
FIG. 4 shows the recombinant packaging process of oncolytic adenovirus AdSVPH548F511 based on the Ad5MixPlus system.
Figure 5:
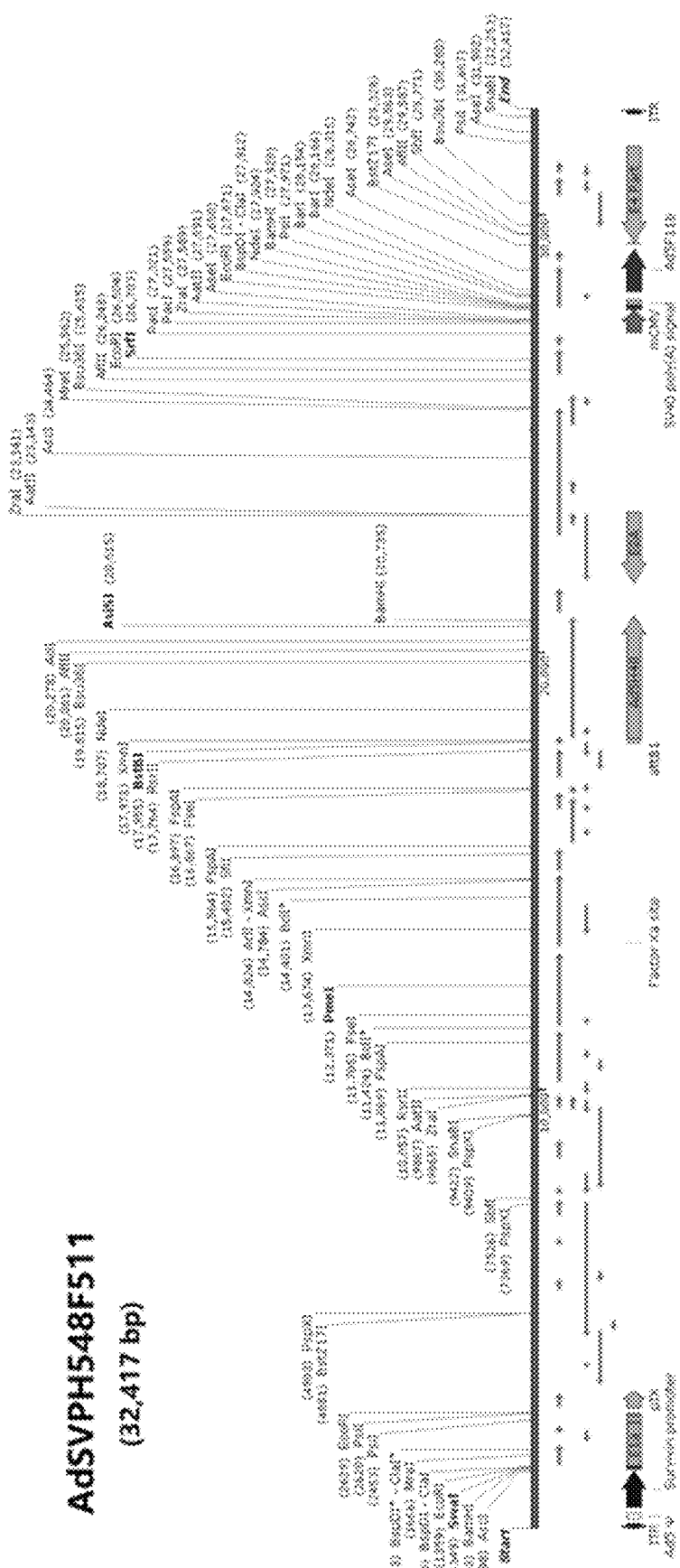
FIG. 5 shows the structure of the oncolytic adenovirus AdSVPH548F511.

Adenovirus right arm shuttle plasmid pAdH548F511LR was recombined with adenovirus right arm backbone plasmid pAd5MixPlus at attL1/attL2 located at both ends of the Hexon/E3/Fiber sequence in DB3.1 E. coli competent cells. After the first round of recombination mentioned above, the sequence between attR1/attR2 in pAd5MixPlus was replaced by the sequence between attL1/attL2 in pAdH548F511LR. Then, the adenovirus left arm shuttle plasmid pAdSVPcreLoxP was recombined with pAd5MixPlus in eukaryotic cells, which is the second round of recombination, leading to that the E1a expression cassette controlled by the tumor-specific promoter in pAdSVPcreLoxP was inserted into the E1 region of pAd5MixPlus. The ideal oncolytic adenovirus was packaged accurately and quickly after the above two rounds of site-specific recombination. The recombinant packaging procedure for Ad5MixPlus system was shown in FIG. 4. The structure of the oncolytic adenovirus AdSVPH548F511 was shown in FIG. 5.

The complete genome sequence of the oncolytic adenovirus AdSVPH548F511 of the present invention is: SEQ ID NO: 4.

The contents that need special explanation are as follows.

1. Modification of Chimeric Hexon Sequence

The second adenovirus recombinant plasmid, adenovirus right arm shuttle plasmid pAdH548F511LR, contains the modified Ad5H48 chimeric Hexon sequence. Due to exposure to the surface of adenovirus, the hypervariable region (HVR) of Hexon is the key site for the difference of liver infection ability and immunogenicity between different serotypes of adenovirus. Using genetic engineering to modify the adenovirus vector, seven HVRs of Hexon on the surface of Ad5 are selectively chimeric with the corresponding regions of Hexon of rare serotype viruses, which is an effective method to help adenovirus evade pre-existing immunity and avoid liver adsorption.

The modified Ad5H48 chimeric Hexon of the present invention was prepared by replacing the corresponding sequence of Ad5 with the HVR of type 48 adenovirus of subgroup D. The population generally lacks neutralizing antibodies against Ad48, and Ad48 has weak liver affinity. Therefore, interception from neutralizing antibodies and uptake by the liver can be avoided and virus survivability is improved by replacing the corresponding part of Ad5 with the HVR of Ad48 to construct Ad5 and Ad48 chimeric Hexon adenovirus. The chimeric Hexon sequence described in this present invention also can be a chimeric sequence constructed by Hexon of Ad5 and Hexon of any other serotype adenovirus, such as Ad9, Ad37, Ad43, or a mutant sequence thereof.

The complete sequence of Ad5H48 chimeric Hexon is SEQ ID No: 5.

2. Modification of Chimeric Fiber Sequence

The second adenovirus recombinant plasmid, adenovirus right arm shuttle plasmid pAdH548F511LR, contains the modified Ad5F11b chimeric Fiber sequence. The human adenovirus family has 51 known serotypes and is divided into 6 subgenus (A to F). CAR is the main recognition receptor of each subgenus adenovirus except B (Ad5 belongs to Subgenus C). Adenoviruses of subgenus B are further divided into subgroups B1 and B2. Ad11b, Ad14, and Ad35 are group B2 adenoviruses; Ad3, Ad16, Ad21, and Ad50 are group B1 adenoviruses. In recent years, subgenus B adenovirus derivatives have attracted much attention as attractive gene therapy vectors because they can infect target cells such as hematopoietic cells, hematopoietic stem cells, dendritic cells (DCs) and malignant tumor cells, which are often not easily infected by commonly used adenovirus vectors such as Ad5. Different from many adenoviruses that infect cells through CAR receptors, subgenus B adenoviruses use CD46 as recognition receptor. CD46 is a widely expressed complement regulatory protein that is present on the surface of almost all human cells. The chimeric Fiber of Ad5F11b is prepared by replacing the corresponding sequence of adenovirus type 5 Fiber with the Fiber knob of Ad11b, so that the chimeric virus has high infection characteristics to hematopoietic cells, stem cells and tumor cells. The chimeric Fiber sequence described in the invention also can be a chimeric sequence constructed by the Fiber of Ad5 and Fiber of any other serotype adenovirus, such as Ad3, Ad14, Ad16, Ad21, Ad35, Ad50, Ad55, or a mutant sequence thereof.

The complete sequence of Ad5F11b chimeric Fiber is SEQ ID No: 6.

3. Tumor Specific Promoter

The third adenovirus recombinant plasmid, adenovirus left arm shuttle plasmid pAdSVPcreLoxP, contains an E1a expression cassette controlled by tumor-specific promoter Survivin inserted at multiple cloning sites of pAdSVPcreLoxP. Survivin promoter has attracted much attention due to its high specificity and wide tumor spectrum. Survivin is rarely expressed in normal tissues, but highly selectively expressed in malignant tumors. It is highly expressed in most tumors such as lung cancer, liver cancer, colon cancer, pancreatic cancer, prostate cancer and breast cancer, and is closely related to tumor recurrence and metastasis and poor prognosis of patients, making it a broad-spectrum molecular target for tumor gene therapy. The oncolytic adenovirus regulated by the Survivin promoter can target cancer cells, replicate in cancer cells, and lyse cancer cells, and at the same time mediate the high-efficiency expression of anti-tumor target genes. Therefore, oncolytic adenovirus regulated by Survivin promoter is expected to be used to obtain broad-spectrum and safe anti-cancer effect against most human tumors. In addition to being a Survivin promoter, the tumor specific promoter of the invention can also be any of the following: (a) promoter, enhancer and mutant sequence of carcinoembryonic antigen; (b) promoter, enhancer and mutant sequence of alpha fetoprotein; (c) promoters, enhancers and mutant sequences of receptor tyrosine kinases (including EGFR, Her-2, Her-3 and Her-4) of the human epidermal growth factor receptor family (EGFRs); (d) promoter, enhancer and mutant sequence of breast cancer related antigen DF3/MUC1; (e) promoter, enhancer and mutant sequence of vascular endothelial growth factor (VEGF) receptor KDR; (f) promoter, enhancer and mutant sequence of L-plastin; (g) promoters, enhancers and mutant sequences of members of the inhibitor of apoptosis protein family (IAP); (h) promoters, enhancers and mutant sequences of prostaglandin-specific antigens; (i) conserved sequences of hypoxia response elements regulated by hypoxia inducible factor-1 (HIF-1); (j) promoter, enhancer and mutant sequence of transcription factor E2F; (k) promoter, enhancer and mutant sequence of hTERT.

The nucleotide sequence of the tumor-specific promoter Survivin in this invention is SEQID NO: 7.

4. Adenovirus Early Replication Gene E1a

The third adenovirus recombinant plasmid, adenovirus left arm shuttle plasmid pAdSVPcreLoxP, contains an E1a expression cassette controlled by tumor-specific promoter Survivin. Adenovirus early replication gene E1a is placed under the regulation of tumor-specific promoter to achieve the purpose of tumor-specific replication and oncolysis of the virus. The sequence of the early replication gene of adenovirus described in this invention can be a wild sequence of E1a, a mutant sequence of E1a, or E1b-55 kDa, E1b-19 kDa or their mutant sequences.

The nucleotide sequence of E1a in the E1a expression cassette controlled by the tumor-specific promoter in this invention is SEQ ID NO: 8.

Example 2 Specific Replication Activity of Oncolytic Adenovirus AdSVPH548F511

Figure 6:
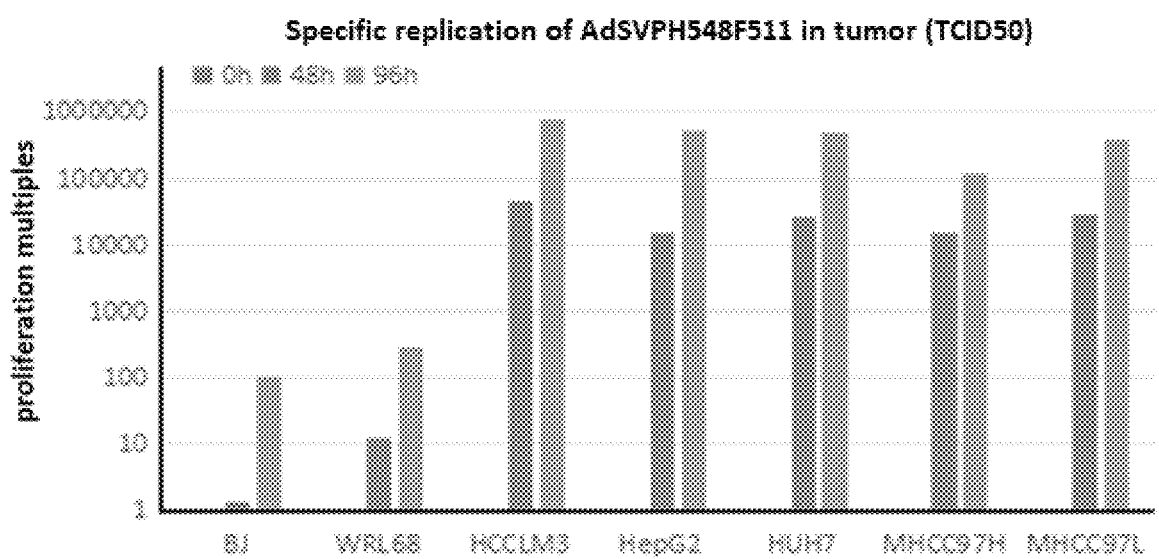
FIG. 6 shows the replication activity of the oncolytic adenovirus AdSVPH548F511 detected by the TCID50 method.

Hepatocellular carcinoma cells (HCCLM3, HepG2, Huh-7, MHCC97H, MHCC97L), normal hepatocytes (WRL-68) or normal fibroblasts (BJ) in logarithmic phase were collected and counted. The cells were seeded on 96-well plates at $1\times10^4$ cells/well, changing to serum-free culture medium after cell adherence. The oncolytic adenovirus AdSVPH548F511 was added to the culture medium at MOI=1. After 2 h of viral infection, the medium was changed to 5% serum medium (This is the starting time of infection 0 h), and the cells were further cultured for 48 h and 96 h. The cells were collected at these three time points, and the virus titer was detected by TCID50 method. The results showed that AdSVPH548F511 had a very strong ability of specific replication in liver cancer cells, and the replication multiples were all above 10,000 times at 48 h, with the maximum was above 50,000 times. After 96 h, it reached 100,000 to 800,000 times. The replication ability of AdSVPH548F51 in normal cells WRL-68 or BJ was very low, and the highest replication multiple at 96 h was below 200 times (FIG. 6).

Example 3 Killing Activity of Oncolytic Adenovirus AdSVPH548F511 on Tumor Cells

Figure 7:
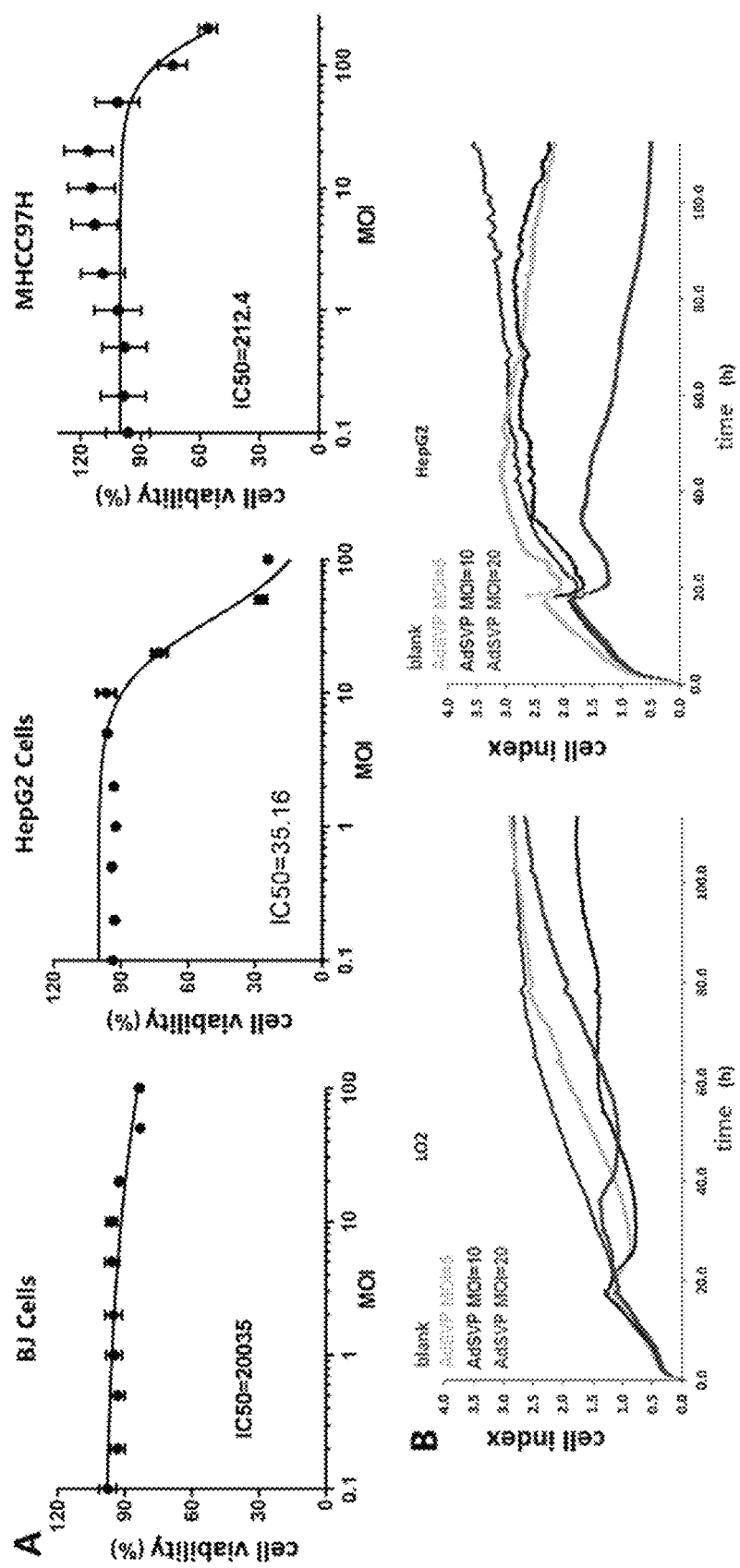
FIG. 7 shows the killing activity of the oncolytic adenovirus AdSVPH548F511 on tumor cells. (A) MTT method, (B) RTCA method.

Hepatocellular carcinoma cells (HepG2, MHCC97H), normal hepatocytes (L02) and normal fibroblasts (BJ) in logarithmic phase were collected and counted. The cells were seeded on 96-well plates at $1\times10^4$ cells/well, changing to serum-free culture medium after cell adherence. The effect of AdSVPH548F511 on cell viability was detected by MTT assay. Cell Proliferation Kit I (MTT) was purchased from Roche Diagnostics GmbH. The viruses were added into culture wells with a gradient of MOIs, with 8 replicates per treatment. Then the cells were cultured in the incubator. After 2 h, the medium was replaced with serum medium for further culture, with the addition amount of 100 μl/well. After 48 hours, the culture medium was discarded, 0.1 mol/L PBS solution was added to the culture well with the dosage 100 μl/hole. Then MTT labeling reagent was added to the culture well to the final concentration of 0.5 mg/ml, and the culture plates were placed in incubator. After 4 h, 100 μl/well of Solubilization solution (10% SDS in 0.01 mol/L HCl) was added to the culture well, and the cells were cultured overnight in an incubator. The Model 550 Microplate Reader (BIO-RAD) was used to measure the light absorption value at 570 nm wavelength, and the corrected wavelength was 655 nm. The survival curve was drawn, and the IC50 value was calculated. The results showed that AdSVPH548F511 had strong killing activity against HepG2 and MHCC97H with IC50 values of 35.16 and 212.4, respectively, while AdSVPH548F511 had no significant effect on normal BJ cells with IC50 value of 20035. It can be seen that oncolytic adenovirus AdSVPH548F511 has the ability to specifically kill and destroy cancer cells (FIG. 7A). At the same time, the killing activity of AdSVPH548F511 on cells was detected in real time, dynamically and quantitatively by Real Time Cellular Analysis (RTCA). E-Plate plate was added with culture medium and background impedance was measured. Hepatocellular carcinoma cells (HepG2) or normal liver cells (L02) in logarithmic growth phase were collected, counted and added to the E-Plate detection plate, and placed in the ultra-clean worktable at room temperature for 30 min. The virus was diluted in serum-free medium and added to E-Plate at MOI=5, 10 or 20. The E-Plate detection plate was placed on the detection platform pre-placed in the incubator for real-time dynamic cell proliferation detection, and the real-time dynamic cell growth curves were plotted. The results showed that the killing activity of AdSVPH548F511 on HepG2 cells increased with the increase of MOIs and time. However, the killing activity of AdSVPH548F511 on normal liver cell L02 was not high. L02 cells were inhibited to some extent only when given high-MOI virus infection (FIG. 7 B).

Example 4 Antitumor Animal Experiment of Oncolytic Adenovirus AdSVPH548F511

Figure 8:
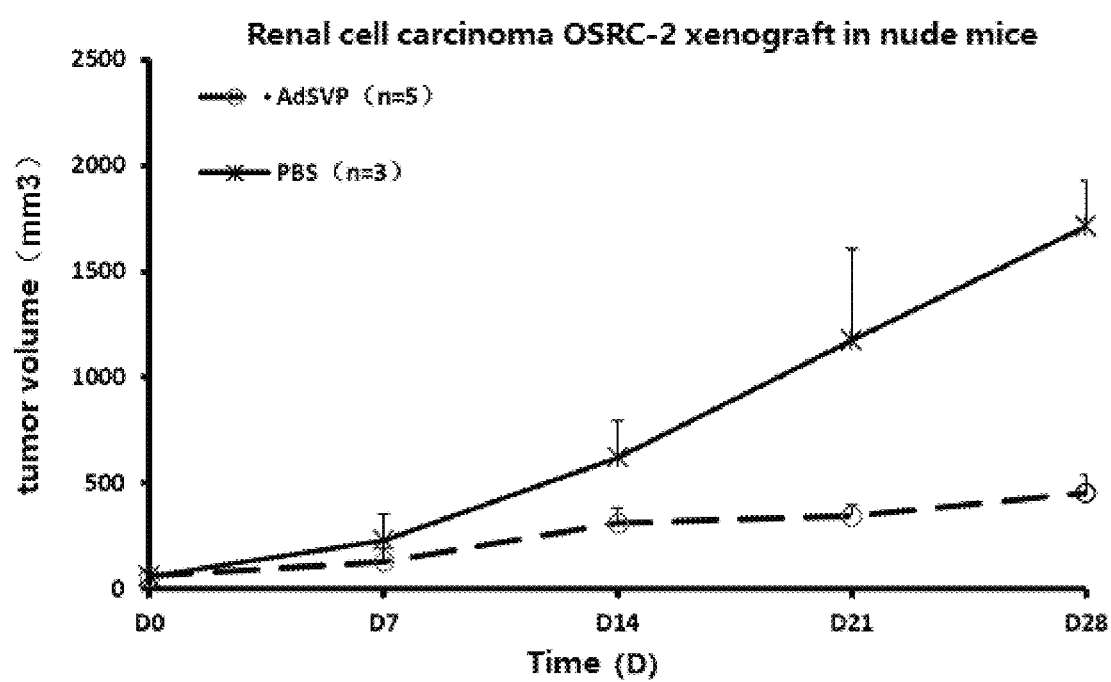
FIG. 8 shows the inhibitory effect of the oncolytic adenovirus AdSVPH548F511 on renal cell carcinoma xenograft.

Eight healthy purebred male BALB/c nude mice aged 6-8 weeks were provided by the Shanghai Experimental Animal Center of the Chinese Academy of Sciences and kept in a clean animal laboratory. Renal carcinoma OSRC-2 cells in logarithmic growth phase were adjusted to $1\times10^7$ cells/ml with PBS. Near-axillary skin on the abdominal side of nude mice was disinfected and subcutaneously injected with 100 μL cell suspension. Then the nude mice were raised under the condition of constant temperature, ventilation and sterility. Tumor growth was regularly observed daily and the presence of a rice-size tumor underneath the inoculation site was considered a success. Model animals were randomly divided into two groups, virus group (AdSVP) n=5, control group (PBS) n=3. Animals were numbered and vernier caliper was used to measure the tumor size. Then treatment was started. The virus AdSVPH548F511 with a concentration of $2\times10^8$ pfu/100 μl was injected directly into the tumor at multiple sites, once every other day, 5 times in total. Control animals were injected with PBS instead of virus, 100 μl×5 times. The tumor size was measured regularly, and the tumor volume was calculated with the formula of 'a×b2×0.5' (a: maximum diameter, b: minimum diameter). The growth curve of transplanted tumor was plotted (FIG. 8). The results showed that AdSVPH548F511 could significantly inhibit the growth of renal cell carcinoma OSRC-2 xenograft.

The above are only the preferred embodiments of the present invention. It will be apparent to one skilled in the art that various changes and modifications can be made therein without departing from the spirit and scope thereof. Such changes and modifications are intended to be encompassed by the scope of the following claims.

The invention claimed is:

1. A recombinant oncolytic adenovirus packaging system comprising the following 3 recombinant adenovirus plasmids:
   a) an adenovirus right arm backbone plasmid comprising two sets of recombinant sequences at different sites, one set of attL/attR in the Fiber/Hexon/E3 region of the plasmid, and the other set of Cre/loxP in the E1 region of the plasmid; the E3 region of the plasmid further comprises the ccdB lethal gene from the DB3.1 strain of *E. coli*;
   b) an adenovirus right arm shuttle plasmid comprising a reconstructed chimeric Hexon sequence wherein the sequence of the reconstructed chimeric Hexon consists of SEQ ID NO: 5 and a reconstructed chimeric Fiber sequence; the E3 region of the plasmid is preset with multiple cloning sites for exogenous gene insertion; Hexon/E3/Fiber sequence contains attL1/attL2 recombination sites at both ends; and
   c) an adenovirus left arm shuttle plasmid comprising a tumor-specific promoter-controlled adenovirus early replication gene and a loxP recombination site inserted at its multiple cloning sites;
   wherein, the first round of attL/attR site-specific recombination is performed between the adenovirus right arm shuttle plasmid and the adenovirus right arm backbone plasmid based on attL1/attL2 at both ends of the Hexon/E3/Fiber sequence, resulting that the sequence between attL1/attL2 in the adenovirus right arm shuttle plasmid replaces the sequence between attR1/attR2 in the adenovirus right arm backbone plasmid; the second round of Cre/loxP site-specific recombination is performed between the adenovirus left arm shuttle plasmid and the adenovirus right arm backbone plasmid, resulting that the in an E1a expression cassette controlled by the tumor-specific promoter in the adenovirus left arm shuttle plasmid is inserted into the E1 region of the adenovirus right arm backbone plasmid; a resulting oncolytic adenovirus is packaged after the above two rounds of site-specific recombination.

2. The recombinant oncolytic adenovirus packaging system of claim 1, wherein the reconstructed chimeric Fiber sequence is a chimeric sequence formed by Fiber of Ad5 and Fiber of Ad11b serotype adenovirus.

3. The recombinant oncolytic adenovirus packaging system of claim 1, wherein the sequence of the reconstructed chimeric Fiber sequence consists of SEQ ID NO: 6.

4. The recombinant oncolytic adenovirus packaging system of claim 1, wherein the tumor-specific promoter is selected from promoters, enhancers and mutant sequences of members of the inhibitor of apoptosis protein family (IAP).

5. The recombinant oncolytic adenovirus packaging system of claim 1, wherein the sequence of the tumor-specific promoter consists of SEQ ID NO: 7.

6. The recombinant oncolytic adenovirus packaging system of claim 1, wherein the adenovirus early replication gene is either wildtype or mutant E1a.

7. The recombinant oncolytic adenovirus packaging system of claim 1, wherein the sequence of the E1a expression cassette consists of SEQ ID NO: 8.

8. A recombinant oncolytic adenovirus packaging system comprising the following 3 recombinant adenovirus plasmids:
   a) an adenovirus right arm backbone plasmid comprising two sets of recombinant sequences at different sites, one set of attL/attR in the Fiber/Hexon/E3 region of the plasmid, and the other set of Cre/loxP in the E1 region of the plasmid; the E3 region of the plasmid further comprises the ccdB lethal gene from the DB3.1 strain of *E. coli;*
   b) an adenovirus right arm shuttle plasmid comprising a reconstructed chimeric Hexon sequence and a reconstructed chimeric Fiber sequence wherein the reconstructed chimeric Fiber sequence consists of SEQ ID NO: 6; the E3 region of the plasmid is preset with multiple cloning sites for exogenous gene insertion; Hexon/E3/Fiber sequence contains attL1/attL2 recombination sites at both ends;
   c) an adenovirus left arm shuttle plasmid comprising a tumor-specific promoter-controlled adenovirus early replication gene and loxP recombination site inserted at its multiple cloning sites; and wherein, the first round of attL/attR site-specific recombination is performed between the adenovirus right arm shuttle plasmid and the adenovirus right arm backbone plasmid based on attL1/attL2 at both ends of the Hexon/E3/Fiber sequence, resulting that the sequence between attL1/attL2 in the adenovirus right arm shuttle plasmid replaces the sequence between attR1/attR2 in the adenovirus right arm backbone plasmid; the second round of Cre/loxP site-specific recombination is performed between the adenovirus left arm shuttle plasmid and the adenovirus right arm backbone plasmid, resulting in an E1a expression cassette controlled by the tumor-specific promoter in the adenovirus left arm shuttle plasmid is inserted into the E1 region of the adenovirus right arm backbone plasmid; a resulting oncolytic adenovirus is packaged after the above two rounds of site-specific recombination.

9. The recombinant oncolytic adenovirus packaging system of claim 8, wherein the reconstructed chimeric Hexon sequence is a chimeric sequence formed by Hexon of Ad5 and Hexon of Ad48 serotype adenovirus.

10. The recombinant oncolytic adenovirus packaging system of claim 8, wherein the sequence of the reconstructed chimeric Hexon sequence consists of SEQ ID NO: 5.

11. The recombinant oncolytic adenovirus packaging system of claim 8, wherein the tumor-specific promoter is selected from promoters, enhancers and mutant sequences of members of the inhibitor of apoptosis protein family (IAP).

12. The recombinant oncolytic adenovirus packaging system of claim 8, wherein the sequence of the tumor-specific promoter consists of SEQ ID NO: 7.

13. The recombinant oncolytic adenovirus packaging system of claim 8, wherein the adenovirus early replication gene is either wildtype or mutant E1a.

14. The recombinant oncolytic adenovirus packaging system of claim 8, wherein the sequence of the E1a expression cassette consists of SEQ ID NO: 8.

* * * * *